US009828641B2

(12) United States Patent
Schiestl et al.

(10) Patent No.: US 9,828,641 B2
(45) Date of Patent: Nov. 28, 2017

(54) SYSTEMIC GENOTOXICITY AS BLOOD MARKER FOR ALLERGIC INFLAMMATION

(71) Applicant: The Regents of the University of California, Oakland, CA (US)

(72) Inventors: Robert H. Schiestl, Encino, CA (US); Aaron Chapman, Los Angeles, CA (US); Daniel Malkin, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 232 days.

(21) Appl. No.: 14/255,906

(22) Filed: Apr. 17, 2014

(65) Prior Publication Data

US 2015/0037789 A1    Feb. 5, 2015

Related U.S. Application Data

(60) Provisional application No. 61/861,380, filed on Aug. 1, 2013.

(51) Int. Cl.
*C12Q 1/68* (2006.01)
*G01N 33/68* (2006.01)

(52) U.S. Cl.
CPC ....... *C12Q 1/6883* (2013.01); *G01N 33/6893* (2013.01); *C12Q 2600/142* (2013.01); *C12Q 2600/156* (2013.01); *C12Q 2600/158* (2013.01); *G01N 2800/122* (2013.01); *G01N 2800/24* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| 8,445,200 | B2 * | 5/2013 | Westbrook | ........... | C12Q 1/6883 |
| | | | | | 435/6.1 |
| 2010/0267037 | A1 * | 10/2010 | Westbrook | ........... | C12Q 1/6883 |
| | | | | | 435/6.16 |
| 2013/0323746 | A1 | 12/2013 | Westbrook et al. | ......... | 435/6.19 |

FOREIGN PATENT DOCUMENTS

| WO | WO 98/09526 | 3/1998 |
| WO | WO 98/41648 | 9/1998 |
| WO | WO 03/008643 | 1/2003 |
| WO | WO 2008/033432 | 3/2008 |
| WO | WO 2009/099679 | 8/2009 |
| WO | WO 2010/053539 | 5/2010 |

OTHER PUBLICATIONS

Muslimovic et al. 'An optimized method for measurement of gamma-H2AX in blood mononuclear and cultured cells.' Nature Protocols. 3(7):1187-1193, 2008.*
Di Pietro et al. 'Biomonitoring of DNA damage in peripheral blood lymphocytes of subjects with dental restorative fillings.' Mutation Research. 650:115-122, 2008.*
U.S. Appl. No. 14/255,882, dated Apr. 17, 2014, Westbrook, et al.
Altindag, O., et al., "Increased DNA damage and oxidative stress in patients with rheumatoid arthritis", Clinical Biochemistry, 2007, 40: 167-171.
Bashir, S. et al., "Oxidative DNA damage and cellular sensitivity to oxidative stress in human immune diseases", Annals Rheumat. Diseases, 1993, 52: 659-666.
Battershill, J. et al., "Factors affecting the incidence of genotoxicity biomarkers in peripheral blood lymphocytes . . . studies", Mutagenesis, 2008, 23: 423-437.
D'Odorico, A. et al., "Reduced plasma antioxidant concentrations and INCR", Scand. J. Gastroenterol, 2001, 36: 1289-1294.
Emery, P. et al., "Evidence-based review of biologic markers as indicators of disease progression and remission in rheumatoid arthritis", 2007, 27: 793-806.
Gur, M. et al., "Relationship between left ventricle geometric patterns and lymphocyte DNA damage in patients with untreated . . . hypertension", Clinical Biochemistry, 2007, 40: 454-459.
Kopjar, N. et al., "Assessment of chemotherapy-induced DNA Damage in peripheral blood . . . Assay", 2002, Teratogenesis, Carcinogenesis, and Mutagenesis, 2002, 22: 13-30.s.
Langhorst, J., "Noninvasive Markers in the Assessment of Intestinal Inflammation in Inflammatory . . . Indices", American J. Of Gastroenterology, 2008, 103(1):162-169.
Majone, F. et al., "Unstabilized DNA breaks in lymphocytes of patients with different subsets of systemic sclerosis", Ann. N.Y. Acad. Sci., 2007, 1108: 240-248.
Vermeire, S., "Laboratory Markers in IBD: Useful, Magic, or Unnecessary Toys?", Gut., 2006, 55(3):426-431.
Westbrook, A., "ATM Deficient Mice Demonstrate an Exacerbated Response to DSS-Induced . . . Response", 2008, AACR Special Conference, Oct. 14-17, 2008, Ko Olina, Oahu, Hawaii, Chemical and Biological Aspects of Inflammation and Cancer, 1pp.

* cited by examiner

*Primary Examiner* — Nora Rooney
(74) *Attorney, Agent, or Firm* — Karen S Canady; canady +lortz LLP

(57) ABSTRACT

The invention provides a method for detection of allergic inflammation in a subject that comprises assaying a test sample of peripheral blood from the subject for a marker of DNA damage. An elevated amount of marker present in the test sample compared to control sample is indicative of inflammation. The method can be adapted for quantitatively monitoring the efficacy of treatment of allergic inflammation in a subject. Markers of DNA damage include single- and/or double-stranded breaks in leukocytes, oxidative DNA damage in leukocytes, or a marker of nitric oxide oxidative activity (protein nitrosylation in leukocytes). This unexpected discovery of markers of systemic genotoxicity present in circulating leukocytes enables detection of allergic inflammation with a relatively simple and minimally invasive assay using peripheral blood.

17 Claims, 37 Drawing Sheets

FIG. 3A
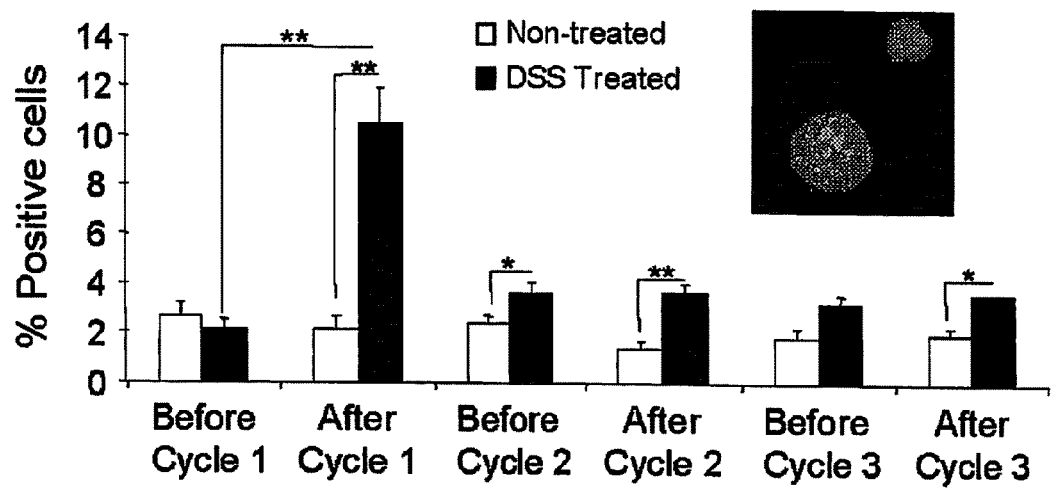
FIG. 3B
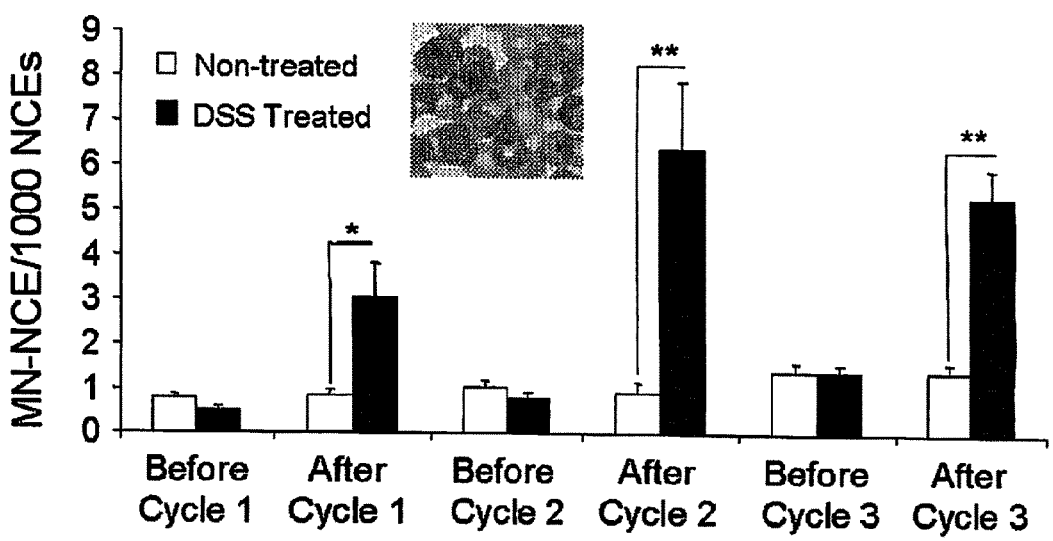
FIGS. 3A - 3B

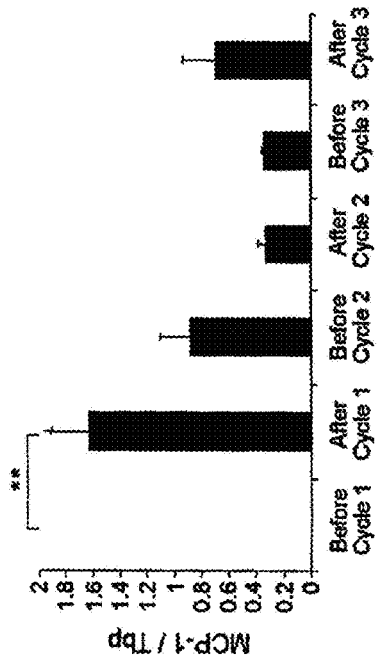
FIG. 4A
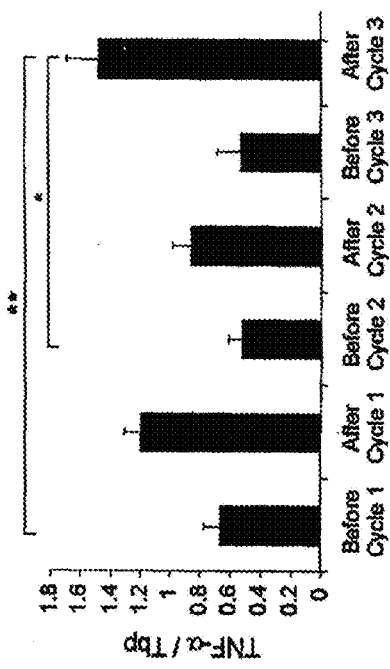
FIG. 4C
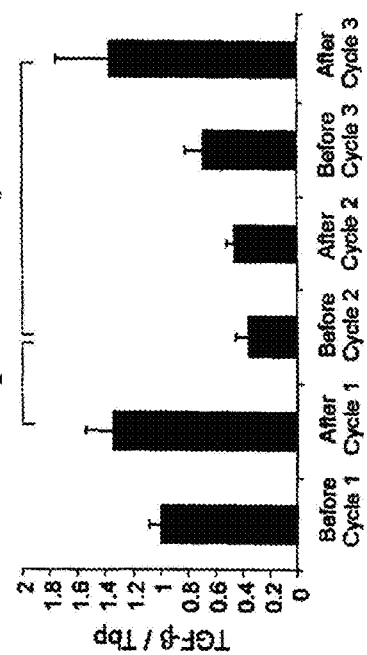
FIG. 4B
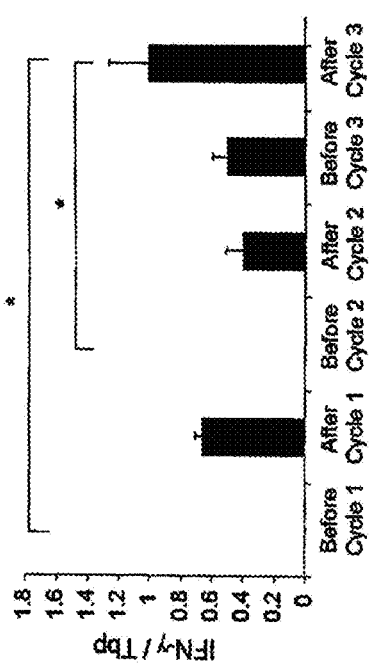
FIG. 4D
FIGS. 4A - 4D FIG. 6A
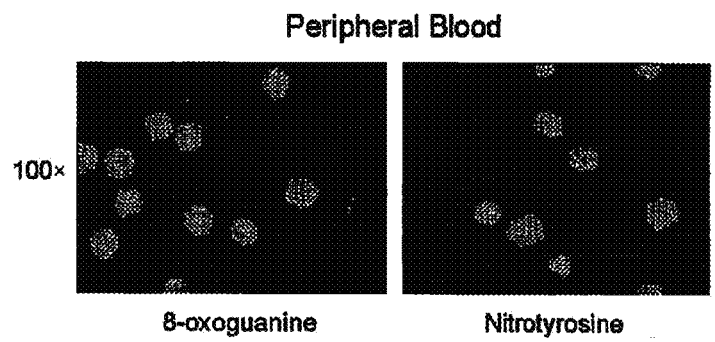
FIG. 6B
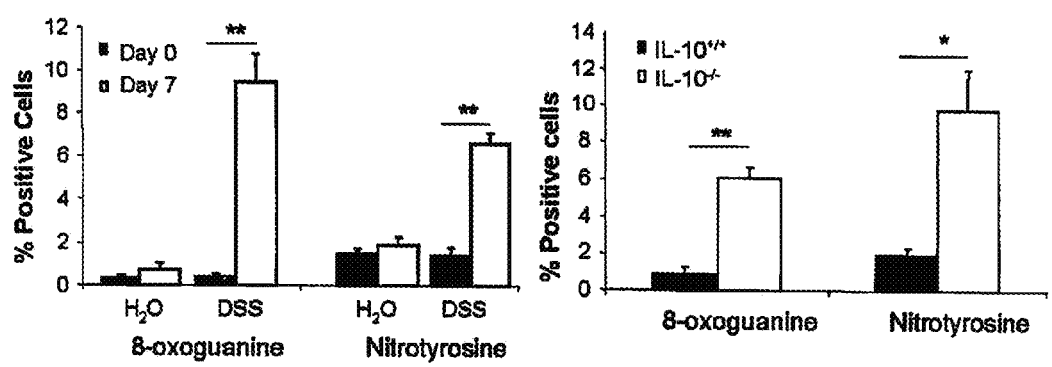
FIG. 6C
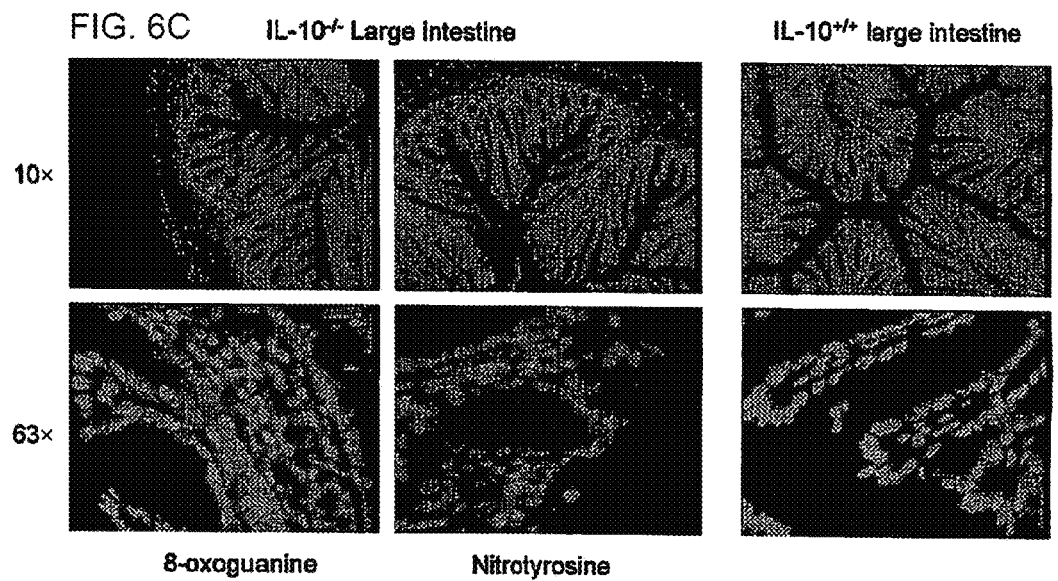
FIGS. 6A - 6C

A,B,E,F,G,H

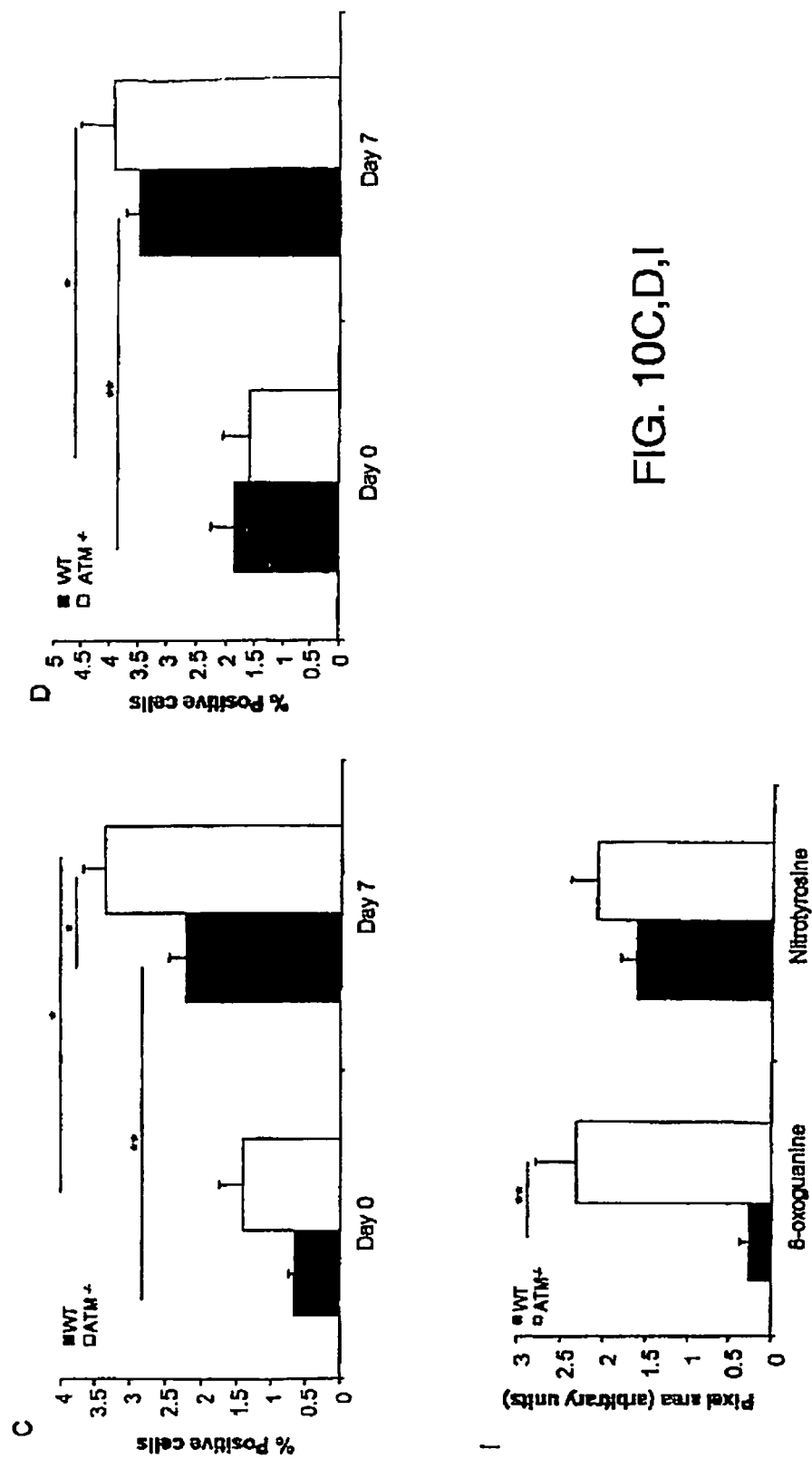
FIG. 10C,D,I

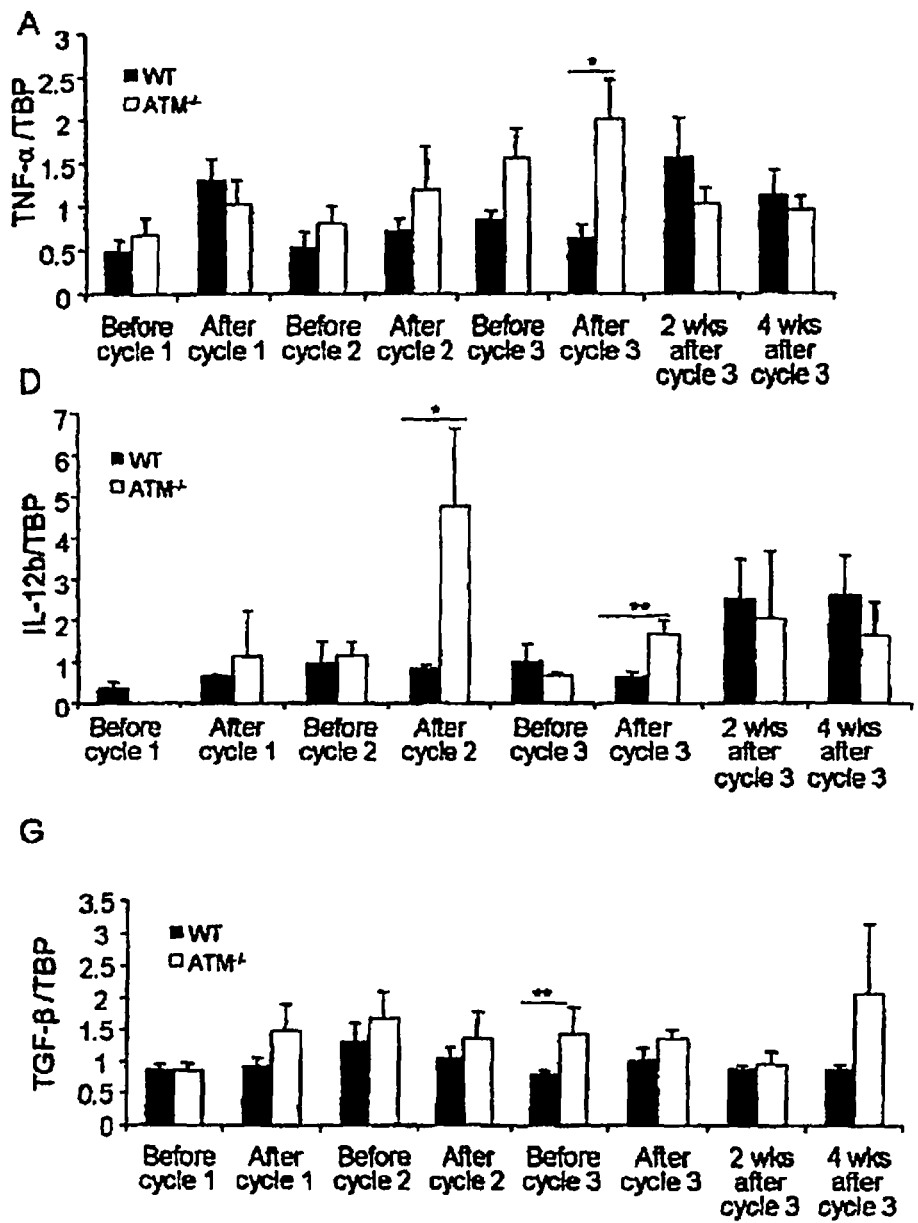
FIG. 11A,D,G

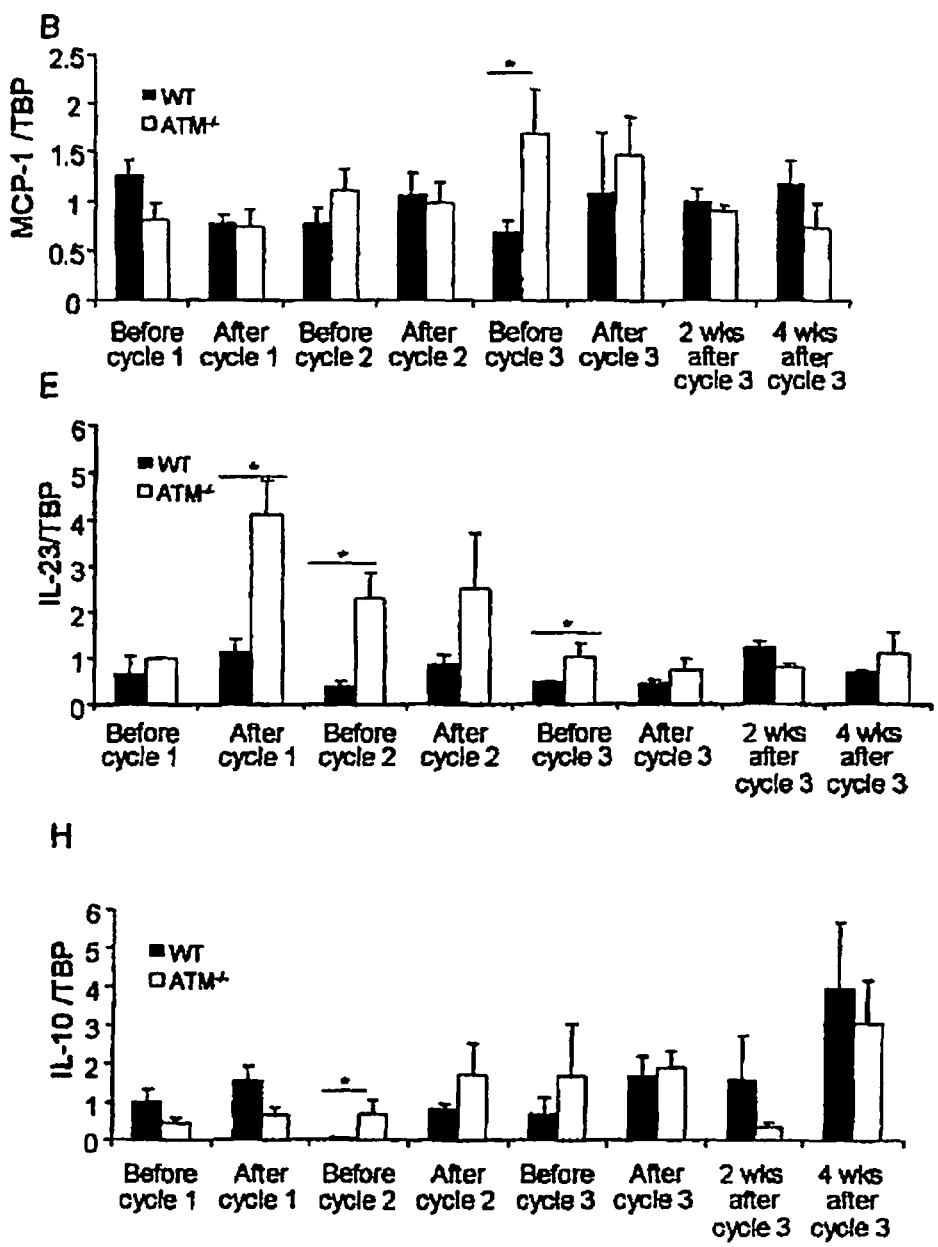
FIG. 11B,E,H

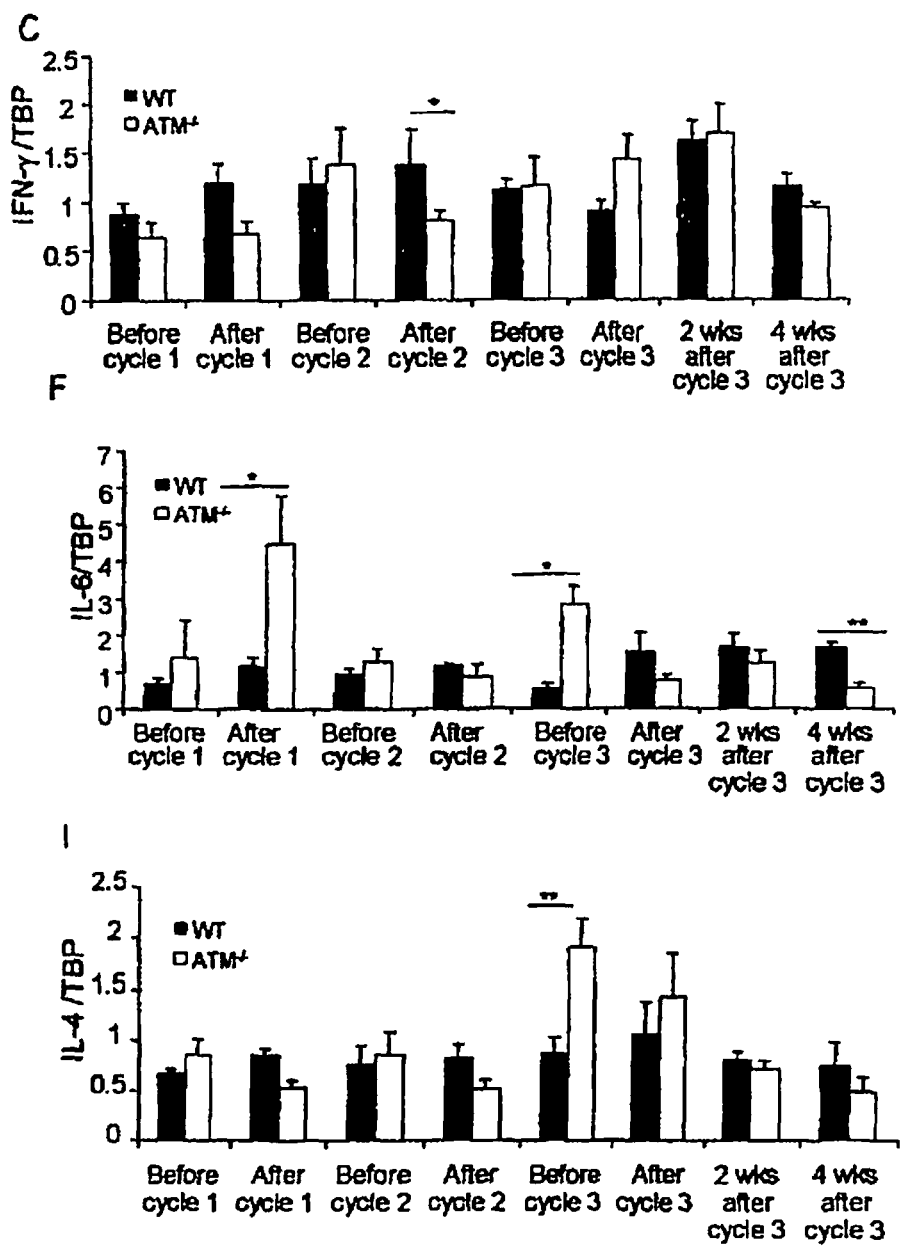
FIG. 11C,F,I

FIG. 12A,B
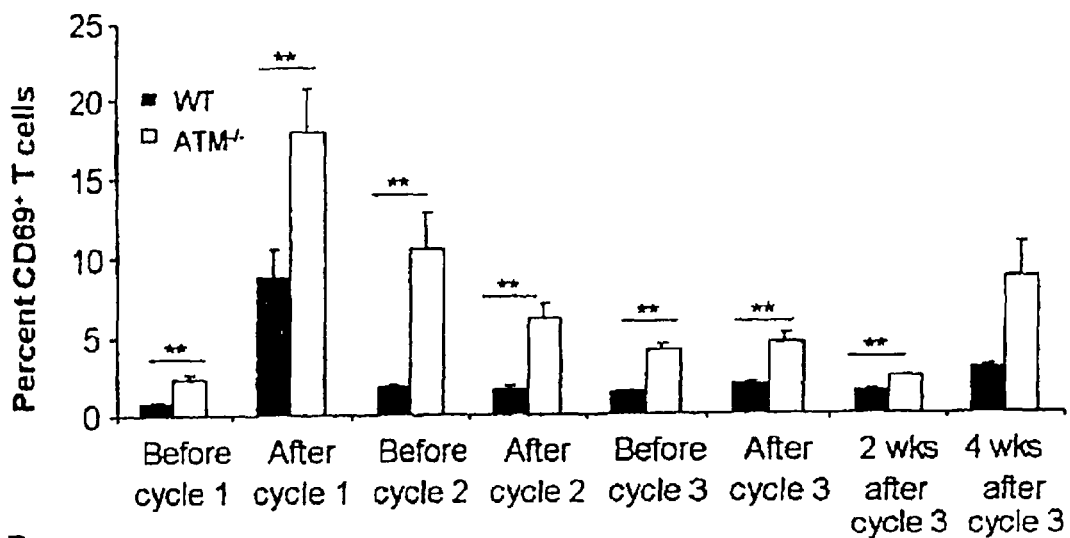
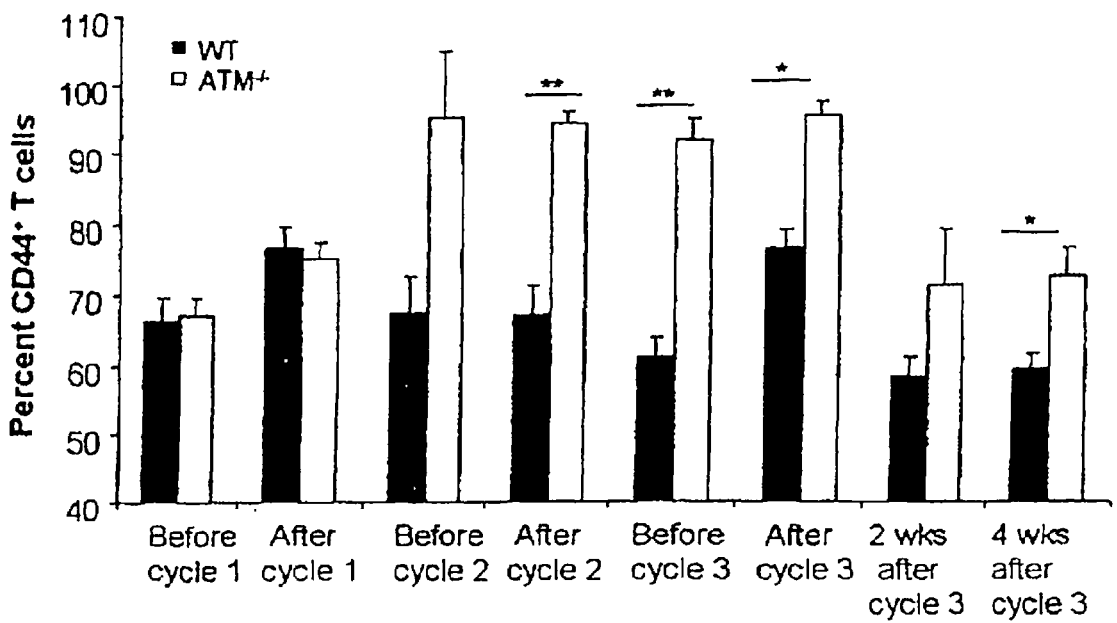

FIG. 13A  Comet Assay
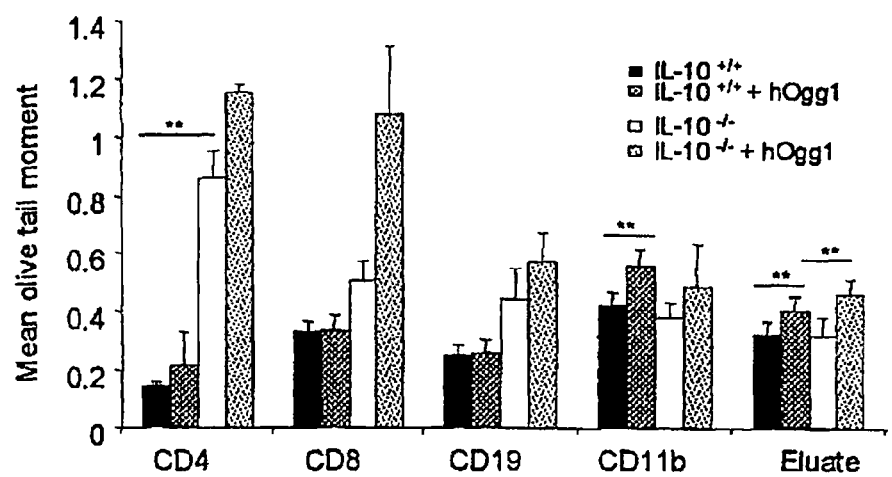
FIG. 13C
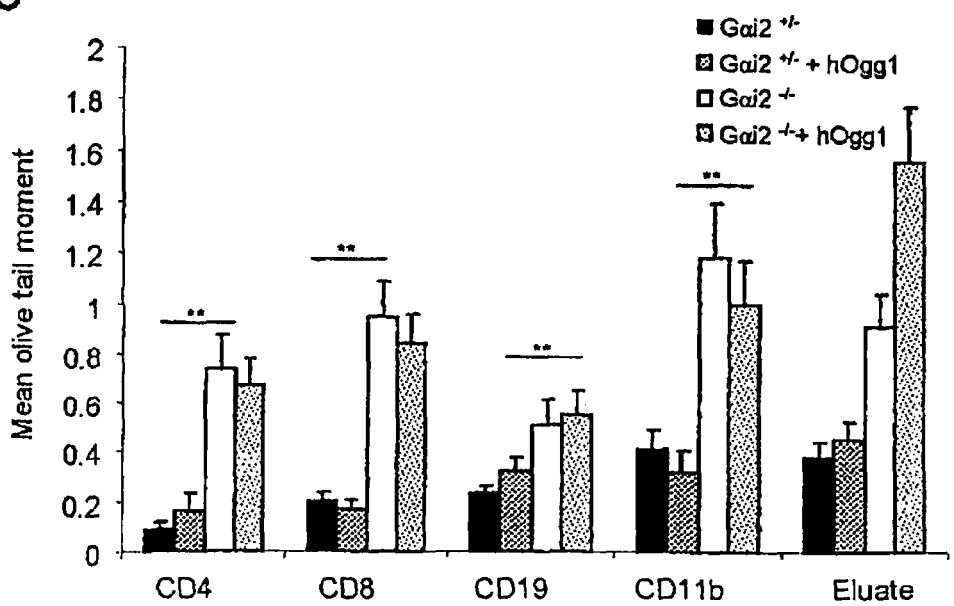

γH2AX

A

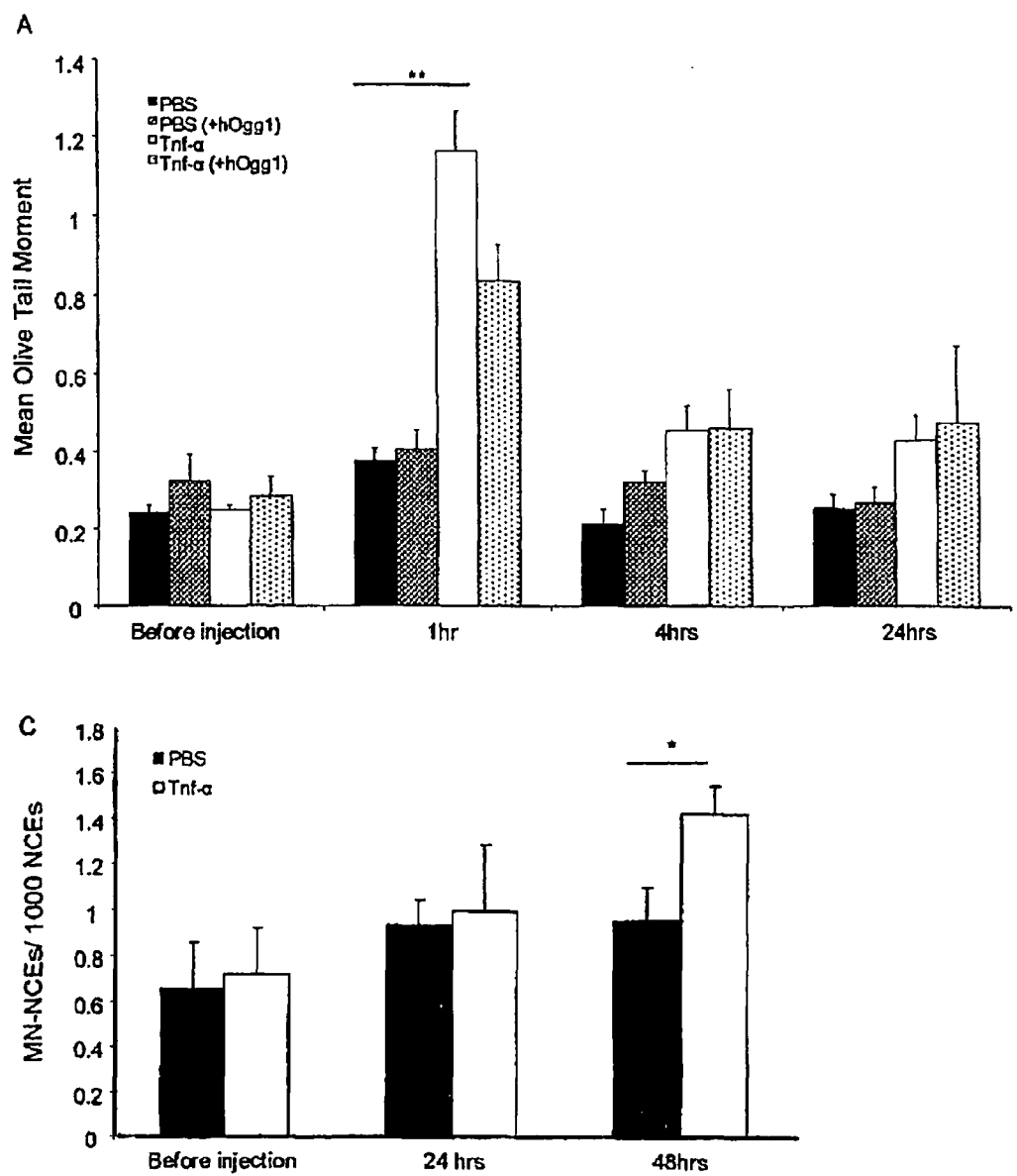
FIG. 16A,C

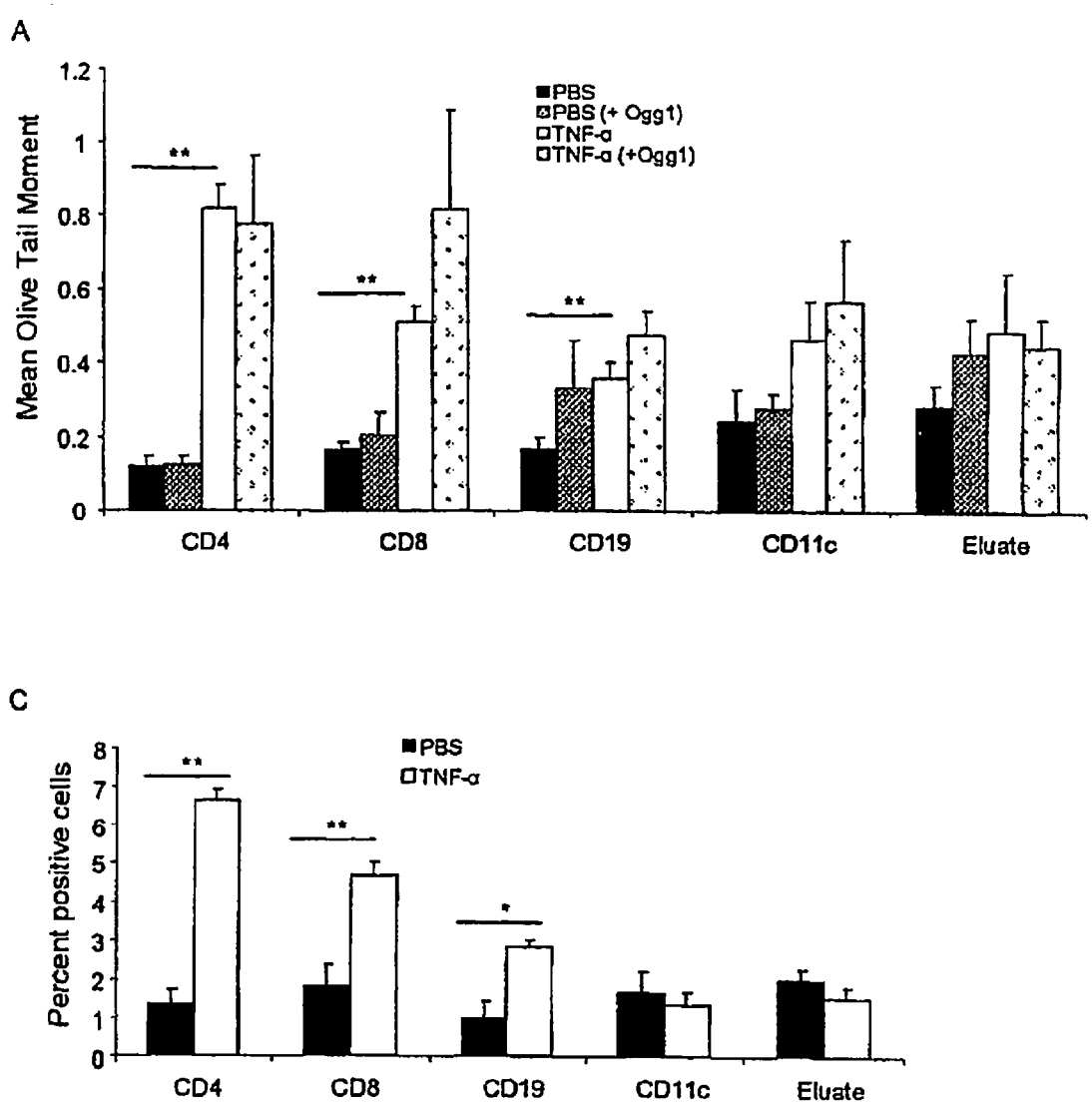
FIG. 17A,C

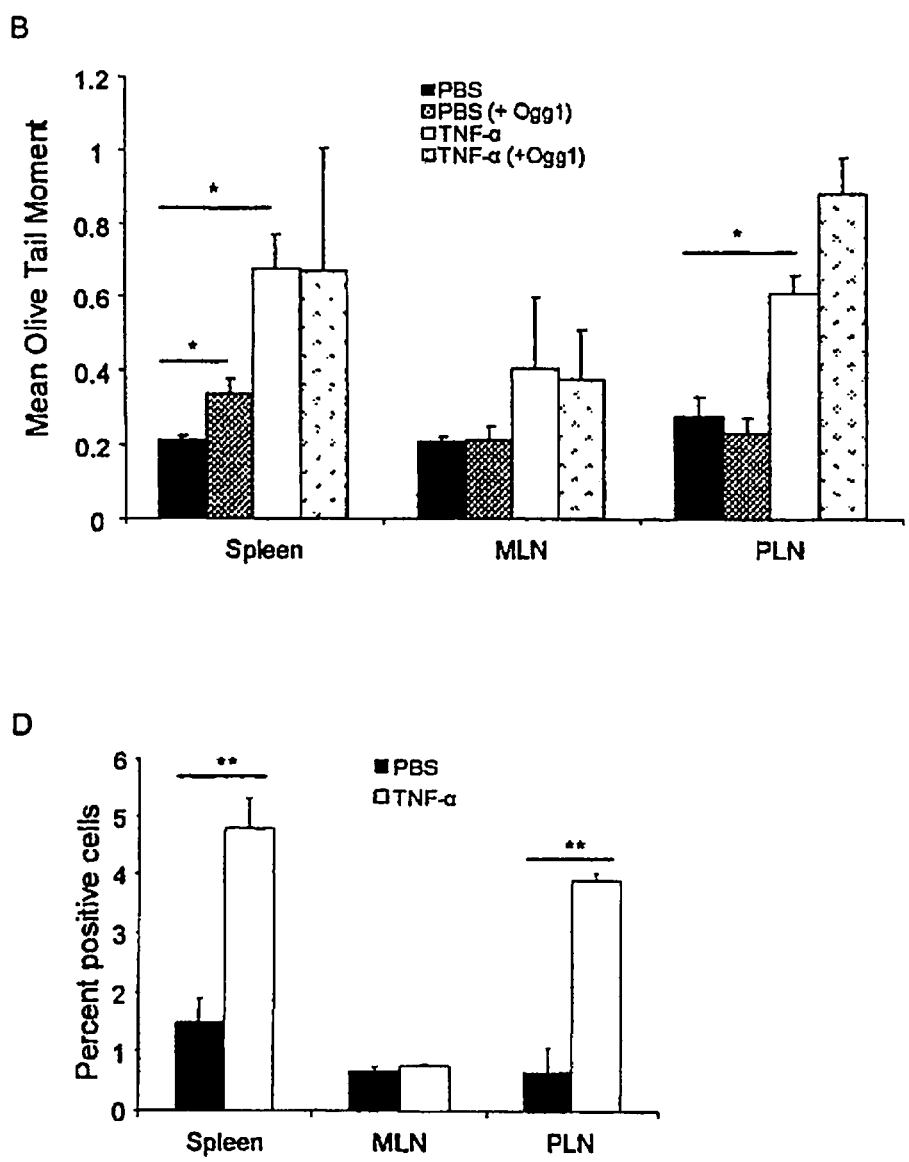
FIG. 17B,D

Fig. 18A,C
A
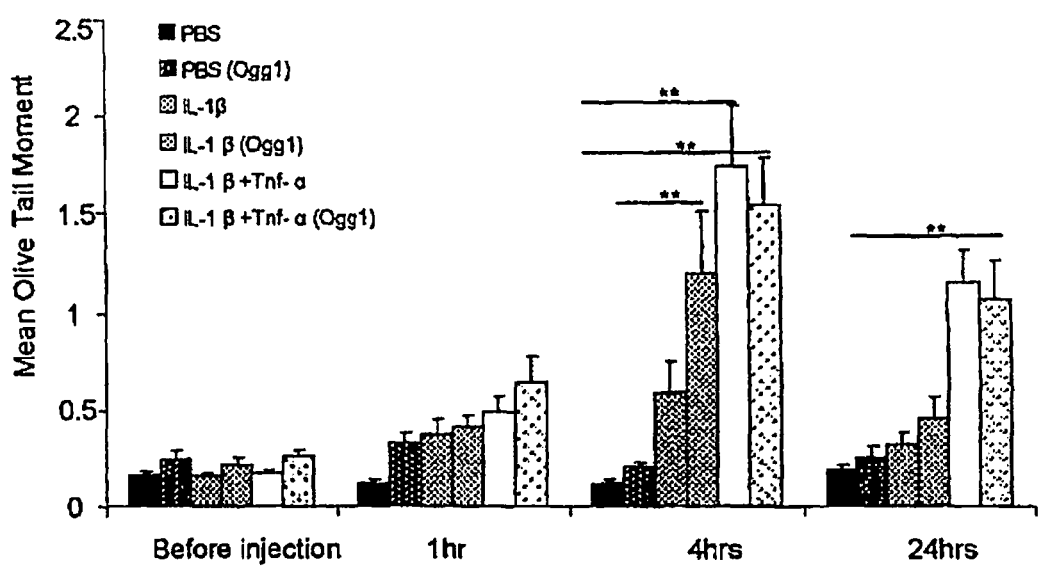
C
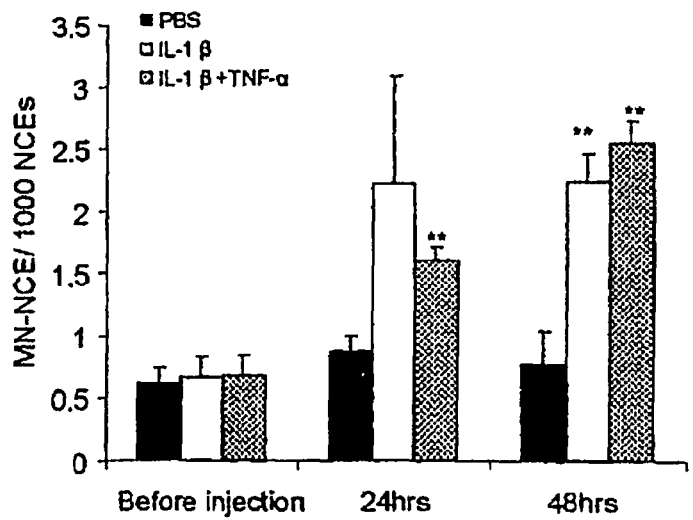

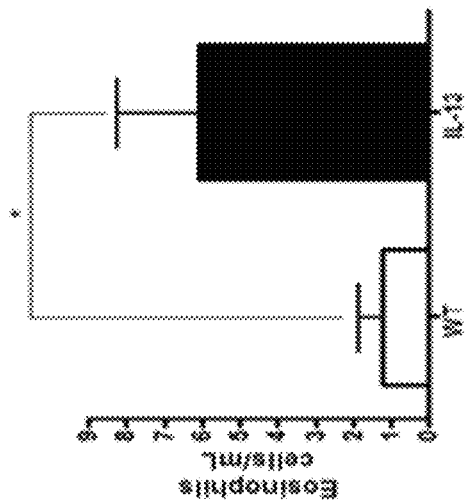
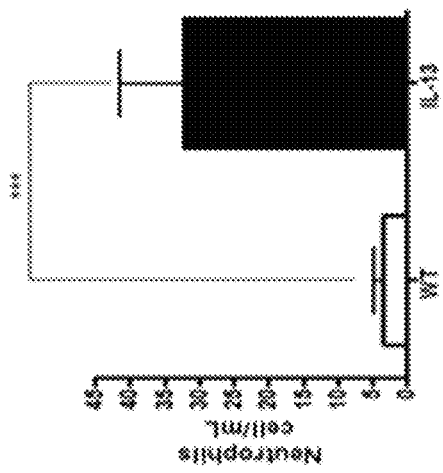
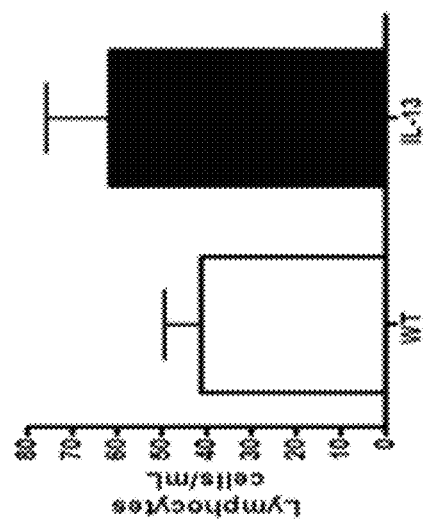
Fig. 23

SYSTEMIC GENOTOXICITY AS BLOOD MARKER FOR ALLERGIC INFLAMMATION

This application claims the benefit of U.S. provisional patent application No. 61/861,380, filed Aug. 1, 2013. This application makes reference to U.S. patent application Ser. No. 13/865,798, filed Apr. 18, 2013, which application is a continuation of U.S. patent application Ser. No. 12/761,330, filed Apr. 15, 2010, which application claims the benefit of U.S. provisional patent application No. 61/169,528, filed Apr. 15, 2009. The entire contents of each of these applications are incorporated herein by reference.

STATEMENT REGARDING FEDERALLY SPONSORED RESEARCH

This invention was made with Government support of Grant No. ES009519, awarded by the National Institutes of Health. The Government has certain rights in the invention.

TECHNICAL FIELD OF THE INVENTION

The present invention relates generally to detection, diagnosis, and monitoring of allergic inflammation, such as occurs with asthma and other respiratory conditions. The invention more specifically pertains to use of systemic genotoxicity as a marker for lung inflammation.

BACKGROUND OF THE INVENTION

Asthma affects over 150 million individuals and is clinically diagnosed by a barrage of symptoms, which include wheezing, coughing, and shortness of breath (Akinbami 2011; Miller 2001). Asthma can be subcategorized into two classes: allergic, and non-allergic asthma, which constitute roughly 70% and 30% of cases, respectively. Although there are almost no observable differences in the types of physiological changes that occur between the two subcategories, non-allergic asthmatics incur more severe and more frequent symptoms (Romanet-Manent 2002).

Airways of asthmatic individuals are distinguished through structural modifications, collectively called airway remodeling that includes bronchiolar inflammation, epithelial sloughing, goblet cell metaplasia, multiplied mucus glands, thickening of the lamina reticularis, increased airway smooth muscle mass, angiogenesis, and alterations in the extracellular matrix components (Fireman 2003; Hyde 2006). Additionally, B lymphocytes, T lymphocytes, eosinophils, neutrophils, and macrophages also migrate to the airways, triggering the release of immunoglobulin E, leukotrienes, prostaglandins, histamines, and other chemical mediators leading to airway inflammation (Bradley 1991; Henderson 1996).

In asthmatic individuals, T cells differentiate preferentially towards type 2 helper T cells (Th2) (Harrington 2005). Th2 cells are thought to induce asthma through the secretion of many cytokines that activate inflammatory pathways both directly and indirectly (Zimmermann 2003). Notably, Th2 cells secrete IL-13 which triggers STATE activation through activation of surface receptors present on eosinophils, mast cells, B lymphocytes, fibroblasts, and airway smooth muscle cells IIs (Chatila 2004, Akdis 2011, Jiang 2000, Cohn 2004, Medoff 2008). This activation leads to IgE synthesis, mucus hypersecretion, airway hyperreactivity, and tissue fibrosis (Munitz 2008). Overexpression of IL-13 is necessary and sufficient to induce non-allergic asthma (Munitz 2008; Akdis 2011; Wills-Karp 1998).

There is a need to identify improved markers for lung inflammation. There is also a need for methods of detecting asthma and differentiating between allergic and non-allergic asthma.

SUMMARY OF THE INVENTION

The invention provides a method for detection of allergic inflammation in a subject. In one embodiment, the method comprises assaying a test sample of peripheral blood from the subject for a marker of DNA damage. The amount of marker present in the test sample is then compared to that present in a control sample. The method can be adapted for quantitatively monitoring the efficacy of treatment of inflammatory disease in a subject. An elevated amount of marker present in the test sample compared to the control sample is indicative of inflammatory disease activity, including sub-clinical inflammation. In some embodiments, the method further comprises prescribing treatment for inflammatory symptoms and/or associated disease or modifying an ongoing treatment strategy on the basis of the assay results.

In one embodiment, the marker of DNA damage is single- and/or double-stranded breaks in leukocytes. Such strand breaks can be detected by immunoassay for $\gamma$-H2AX and/or an alkaline comet assay. In another embodiment, the marker of DNA damage is oxidative DNA damage in leukocytes, or a marker of nitric oxide oxidative activity (protein nitrosylation in leukocytes). Oxidative DNA damage can be assayed via an enzyme hOgg1-modified comet assay or by immunoassay for 8-oxoguanine. An underlying oxidative process (nitric oxide-mediated oxidation) can be assayed by immunoassay for protein nitrotyrosine. In a further embodiment, the marker of DNA damage is micronuclei formation in mature, normochromatic erythrocytes.

The inflammatory disease can be lung inflammation, or inflammation of the airway. In one embodiment, the inflammatory disease is a disease associated with interleukin 13 (IL-13) activity, such as allergic inflammation. In one embodiment, the allergic inflammation is allergic asthma. The invention may also be used for detection of other types of inflammatory disease, such as inflammatory bowel disease, non-immune intestinal inflammatory disease (diverticulitis, pseudomembranous colitis), autoimmune diseases (rheumatoid arthritis, lupus, multiple sclerosis, psoriasis, uveitis, vasculitis), or non-immune lung diseases (asthma, chronic obstructive lung disease, and interstitial pneumonitis). In one embodiment, the method can be used to distinguish between allergic asthma and non-allergic asthma.

Also provided is a method for monitoring the efficacy of treatment of inflammatory disease in a subject. The method comprises assaying a test sample of peripheral blood obtained from the subject at a first time point for a marker of DNA damage, and again at a second time point, and comparing the amount of marker present in the test samples obtained at the first and second time points. A decreased amount of marker present in the test sample obtained at the second time point compared to the test sample obtained at the first time point is indicative effective treatment of inflammatory disease.

BRIEF DESCRIPTION OF THE DRAWINGS

FIGS. 3A-3B. γ-H2AX foci and Micronucleus Induction. FIG. 3A. Percent positive cells for γ-H2AX foci in peripheral leukocytes. Presence of double strand breaks was confirmed by immunofluorescence of γ-H2AX. Positive cells contained >4 distinct nuclear foci. Image caption: Positive and negative cell for nuclear foci, 100× magnification. At least 125 cells were analyzed per sample. Data are represented as mean±SEM, n=10 per treatment group. **: p<0.01, *: p<0.05 FIG. 3B. Micronucleus induction in peripheral normochromatic erythrocytes. At least 4000 normochromatic erythrocytes were counted and scored for presence of micronuclei. Data are represented as mean±SEM of micronucleated normochromatic erythrocytes (MN-NCE) per 1000 NCEs. Image caption: MN-NCEs and NCEs, 100× magnification. **: p<0.01, *: p<0.05, by nonparametric one way ANOVA with Dunn's multiple comparison test. ANOVA of normal linear regression showed effect of treatment, cycle of treatment and interaction of effect of treatment and cycle of treatment to be significant (p<0.01).

FIGS. 4A-4D. Quantitative Real Time-PCR of Cytokines in Peripheral Blood. Expression levels of cytokines were determined only in DSS treated mice (n=10). Data are represented as mean±SEM of gene expression divided by Tbp expression. FIG. 4A. Transcript levels of TNF-α divided by Tbp. FIG. 4B. Transcript levels of MCP-1 divided by Tbp. FIG. 4C. Transcript levels of IFN-γ divided by Tbp. FIG. 4D. Transcript levels of TGF-β divided by Tbp. Statistical significance was determined by non-parametric one-way ANOVAs with Dunn's multiple comparison test. *: p<0.05, **: p<0.01

FIG. 5A. Representative colon histology (hematoxylin and eosin staining at indicated magnifications) from Gαi2 and IL-10 mice, both at age 3 months. FIG. 5B. Alkaline comet assay with and without hOgg1 incubation was carried out in peripheral leukocytes. Error bars are SEM, n=6 per group. *: p<0.05, **: p<0.01 by Student's unpaired t-test. FIG. 5C. Percent positive cells for γ-H2AX foci in peripheral leukocytes. Error bars are SEM. *:p<0.05 by Student's unpaired t-test. FIG. 5D. MN-NCEs per 1000 NCEs in peripheral blood. Error bars are SEM. **: p<0.01 by Student's unpaired t-test.

FIGS. 6A-6C. 8-oxoguanine and Nitrotyrosine Formation in Peripheral Leukocytes and the Colon. FIG. 6A. Representative images of positive staining for 8-oxoguanine (green, left) and nitrotyrosine (red, right) in leukocytes of DSS-treated wildtype (7 days) and IL-10$^{-/-}$ mice (6 months). FIG. 6B. Percent positive cells for 8-oxoguanine and nitrotyrosine staining before and after DSS treated mice (7 days), n=6 per group (LEFT) and in IL-10$^{-/-}$ mice (6 months), n=4 per group (RIGHT). *: p<0.05, **: p<0.01 by Student's unpaired t-test. FIG. 6C. Representative images of 8-oxoguanine (green) and nitrotyrosine (red) in colon sections of IL-10$^{-/-}$ mice (6 months) and wildtype mice.

FIGS. 10A-10B. 8-oxoguanine (green) and nitrotyrosine (red) staining in peripheral leukocytes, respectively (×100). FIGS. 10C-10D. Percent positive cells for 8-oxoguanine and nitrotyrosine, respectively, in peripheral leukocytes of Atm$^{-/-}$ and wildtype mice. *: p<0.05, : p<0.01 by Student's unpaired t-test. FIGS. 10E-10F. Staining in the distal colon of wildtype mice for 8-oxoguanine and nitrotyrosine, respectively, treated with DSS for 7 days. (×10) FIGS. 10G-10H. Staining in the distal colon of Atm$^{-/-}$ mice for 8-oxoguanine and nitrotyrosine, respectively, treated with DSS for 7 days. (×10) FIG. 10I. Quantification of 8-oxoguanine and nitrotyrosine staining in wildtype and Atm$^{-/-}$ mice expressed in pixel area with brightness value above a set threshold (arbitraty units). : p<0.01 by Student's unpaired t-test.

FIGS. 11A-11I. Cytokine panel in peripheral blood by quantitative real-time PCR. FIGS. 11A-11C. Th1 cytokine panel of TNF-α, MCP-1, and IFN-γ, respectively. FIGS. 11D-11F. IL-12, IL-23, and IL-6, respectively. FIGS. 11G-11I. Th2 cytokine panel of TGF-β, IL-10, and IL-4, respectively. Data are mean expression of gene over expression of TBP, the internal control gene. *: p<0.05, **: p<0.01 by two-way ANOVA for genotype comparisons.

FIGS. 12A-12D. Flow cytometric analysis of peripheral leukocytes. FIGS. 12A-12B. Percent gated CD69$^+$ T-cells (CD4 or CD8α positive) and CD44$^+$ T-cells, respectively, in peripheral blood. 15,000 cells were counted per mouse. *: p<0.05, **: p<0.01 by Student's unpaired t-test with Welch correction for genotype comparisons. FIG. 12C. Baseline CD4$^+$ and CD8α$^+$ peripheral blood T-cells of Atm$^{-/-}$, Atm$^{+/-}$, and wildtype mice. Scale along both X and Y axes ranges from $10^0$ to $10^4$. FIG. 12D. Mean fluorescent intensities of CD44$^+$ T-cells in Atm$^{-/-}$, Atm$^{+/-}$, and wildtype mice after cycle 2 (upper panel) and before cycle 3 (lower panel). Filled line represents isotype control. Y axes display counts on a scale from 0 to 100. X axes range from $10^0$ to $10^4$.

FIGS. 13A-13D. Genotoxicity to peripheral leukocyte subpopulations. FIGS. 13A-13B. DNA damage as measured by alkaline comet assay with or without hOgg1 incubation and γH2AX immunostaining, respectively, in IL-10$^{-/-}$ versus wildtype mice. FIGS. 13C-13D. DNA damage as measured by alkaline comet assay with or without hOgg1 incubation and γH2AX immunostaining, respectively, in Gαi2$^{-/-}$ versus wildtype mice. *: p<0.05, **: p<0.01 by two way ANOVA with Dunn's multiple comparison test. Error bars represent standard error of the mean (SEM).

FIGS. 16A-16C. Induction of DNA damage by TNF-α injection. DNA damage to peripheral leukocytes measured by alkaline comet assay with and without hOgg1 incubation, γH2AX immunostaining, and micronuclei formation measured in normochromatic erythrocytes, respectively, in wildtype mice before and after a single injection of TNF-α or saline. *: p<0.05, **: p<0.01 by one way ANOVA with Dunn's multiple comparison test. Error bars represent SEM.

FIGS. 17A-17D. Characterization of cell types with DNA damage after TNF-α injection. FIGS. 17A-17B. DNA damage measured 1.5 hrs post-injection of TNF-α or saline by alkaline comet assay with and without hOgg1 incubation, in peripheral blood subpopulations and in peripheral lymphoid organs, respectively. FIGS. 17C-17D. DNA damage by γH2AX immunostaining in peripheral blood subpopulations and in peripheral lymphoid organs, respectively. *: p<0.05, **: p<0.01 by one way ANOVA with Dunn's multiple comparison test. Error bars represent SEM.

FIGS. 18A-18C. DNA damage after injection of TNF-α and IL-β. DNA damage to peripheral leukocytes measured by alkaline comet assay with and without hOgg1 incubation, γH2AX immunostaining, and micronuclei formation measured in normochromatic erythrocytes, respectively, in wildtype mice before and after a single injection of IL-β, TNF-α+IL-β, or saline. *: p<0.05, **: p<0.01 by one way ANOVA with Dunn's multiple comparison test. Error bars represent SEM.

FIG. 19A. Transcript levels of ATM and XPC relative to the internal control TBP in IL-10$^{-/-}$ versus wildtype mice. FIG. 19B. Protein expression of pATM in CD4 and CD8 T-cells in IL-10$^{-/-}$ versus wildtype mice. *: p<0.05, **: p<0.01 by unpaired Student's t-test. Error bars represent SEM.

FIG. 23. Bar graphs showing inflammatory cell composition of bronchial alveolar lavage fluid (BALF). Differential cell analysis were determined by light microscopic evaluation n=9 for WT, and n=10 for IL-13 animals, * indicates p<0.05, *** indicates p<0.0004 respectively analysis were conducted using two tailed Student's unpaired T-test with Mann-Whitney determination.

DETAILED DESCRIPTION OF THE INVENTION

Figure 1:
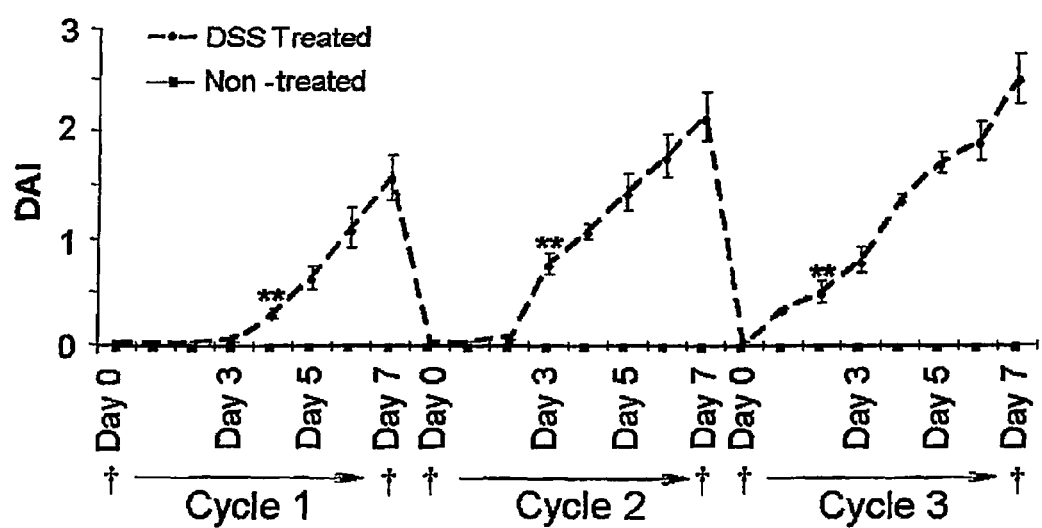
FIG. 1. Disease Activity Index (DAI) of DSS Treated vs. Non-Treated Mice. DSS treated mice (n=10) demonstrated significantly higher disease activity indices everyday after Day 4 of Cycle 1 (p<0.001), Day 3 of Cycle 2 (p<0.001), and Day 2 of Cycle 3 (p<0.001) compared to non-treated mice (n=10). Data are represented as mean±standard error of the mean (SEM). †: Blood collection points.

The invention described herein is based on the discovery that assays that detect systemic genotoxicity can be used to detect, diagnose and monitor inflammation and inflammatory disease, as well as to guide in the prognosis and selection of treatment. Assays that detect a variety of endpoints for genotoxicity in peripheral leukocytes have been found to correlate quantitatively with intestinal inflammation and disease severity. These assays include immunostaining for γ-H2AX, which measures DNA double strand breaks, and the alkaline comet assay, which measures levels of DNA single and double strand breaks, as well as oxidative DNA base damage. DNA damage can also be measured by assaying micronucleus formation in normochromatic erythrocytes. This unexpected discovery of markers of genotoxicity present in circulating leukocytes enables detection of inflammation occurring at a localized site with a relatively simple and minimally invasive assay using peripheral blood.

In particular, these assays have been found to be useful in the detection and monitoring of different types of inflammatory activity. In addition to intestinal inflammation, the methods described herein can be used to detect lung inflammation and inflammatory activity associated with IL-13 activity, including allergic inflammation and asthma. In one embodiment, the invention provides methods for the detection, monitoring, and treatment of allergic asthma.

Definitions

All scientific and technical terms used in this application have meanings commonly used in the art unless otherwise specified. As used in this application, the following words or phrases have the meanings specified.

As used herein, "inflammatory disease" means a clinical disorder in which activation of the innate or adaptive immune response is a prominent contributor to the clinical condition.

As used herein, a "sample" from a subject means a specimen obtained from the subject that contains blood or blood-derived cells. In a typical embodiment, the sample is peripheral blood or other sample containing peripheral leucocytes. For example a sample of peripheral leukocytes can be obtained from fluid of a body cavity, such as pleural, peritoneal, cerebrospinal, mediastinal, or synovial fluid.

As used herein, the term "subject" includes any human or non-human animal. The term "non-human animal" includes all vertebrates, e.g., mammals and non-mammals, such as non-human primates, horses, sheep, dogs, cows, pigs, chickens, amphibians, reptiles, etc.

As used herein, "a" or "an" means at least one, unless clearly indicated otherwise.

Methods of Detecting Inflammatory Activity

The invention provides a method for detection of inflammatory disease activity in a subject. In one embodiment, the method comprises assaying a test sample of peripheral leukocytes from the subject for a marker of DNA damage. The amount of marker present in the test sample is then compared to that present in a control sample. An elevated amount of marker present in the test sample compared to the control sample is indicative of inflammatory disease.

A control sample is a sample that is representative of a normal or disease-free condition. In some embodiments, a control is a sample obtained from a subject known to be normal or free of disease that would alter the measured parameters.

The test sample is typically peripheral blood. Alternatively, the test sample can be bone marrow or body cavity fluids (such as peritoneal, pleural, synovial, or cerebrospinal fluids). DNA damage detected in peripheral blood leucocytes correlates with disease activity and with DNA damage in lymphoid organs, such as spleen, mesenteric lymph nodes and peripheral lymph nodes, and in intestinal epithelial cells. Test samples can be obtained from subjects using conventional means, such as venipuncture or capillary puncture. Normally the most desirable site for obtaining a blood sample for laboratory testing is from the veins of the antecubital fossa area, i.e. the bend of the elbow of the arm. A capillary puncture may be used when venipuncture would be too invasive or not possible. In general, capillary punctures may be done on earlobes, fingertips, heels, or toes, however, heels and toes are not a site of choice, especially in adults. Heel areas are typically used with neonates and younger infants. The site of choice in older children as well as adults is the distal lateral aspect of the fingertip; usually the second or third finger.

One can also assay DNA damage in subpopulations of leukocytes. In some embodiments, the leukocytes are lymphocytes, including subsets of lymphocytes, such as T cells, B cells, and/or NK cells. Also contemplated are monocytes, including subsets of monocytes, such as classical and pro-inflammatory monocytes. As one example, CD4+ and CD8+ T-cells, CD19+ B-cells, and CD11b+ macrophages can be separated, such as by magnetic bead separation, for analysis. An increase in the diversity of cell types exhibiting DNA damage can be indicative of more severe or advanced disease.

In one embodiment, the marker of DNA damage is single- and/or double-stranded breaks in the cells to be analyzed. DNA strand breaks can be detected by immunoassay for γ-H2AX and/or an alkaline comet assay. One example of an immunoassay for γ-H2AX is an immune-fluorescence assay using an antibody directed against γ-H2AX that is directly labeled, or that is used in conjunction with a labeled secondary antibody. Immunoreactive cells can be imaged using FISH analysis, wherein cells having at least four distinct foci in the nucleus are considered positive. Apoptotic cells can be distinguished and excluded from the analysis. An example of an alkaline comet assay for measuring DNA damage in cells has been described by Olive et al. (*Nat. Protocols* 2006; 1(1):23-9). Comet images can be visualized, for example, using fluorescence microscopy, and analyzed using a CASP image analysis program. Tail length and fraction of DNA in the tail is represented in this assay by the olive tail moment.

In another embodiment, the marker of DNA damage is oxidative DNA damage in the cells to be analyzed. Oxidative DNA damage can be assayed via an enzyme hOgg1-modified comet assay. An example of an hOgg1 comet assay has been described by Smith et al. (*Mutagenesis* 2006; 21(3):185-90). In a further embodiment, the marker of DNA damage is micronuclei formation in mature, normochromatic erythrocytes, as described in the examples below and in *Cancer Res.* 2009; 69(11):4827-34; and *Cancer Res.* 2010; 70(5):1875-84.

The inflammatory diseases that can be detected include diseases associated with IL-13 and inflammation of the airway, including lung disease. Examples of lung inflammation that can be detected and monitored include, but are not limited to, asthma, chronic obstructive lung disease, and interstitial pneumonitis. In one embodiment, the method can be used to differentiate between allergic and non-allergic asthma. The markers of genotoxicity described herein can be used to detect the presence of allergic asthma, which can present with similar symptoms as non-allergic asthma. Thus, the invention provides a simple blood test for detection of asthma. Likewise, the invention provides a simple blood test for allergic inflammation.

Those skilled in the art will appreciate additional variations suitable for the method of detecting inflammation through detection of DNA damage in a specimen, as it provides remote monitoring (peripheral blood genotoxicity) to assess disease activity and response to treatment. This method can also be used to monitor levels of these markers in a sample from a patient undergoing treatment. The suitability of a therapeutic regimen for initial or continued treatment can be determined by monitoring marker levels using this method. The extent of genotoxicity present in a given patient or test sample can provide a prognostic indicator to guide treatment strategy. Accordingly, one can use information about the number and/or quantity of indicators present in a subject to assist in selecting an appropriate treatment protocol. For example, treatment of asthma could be monitored by systemic genotoxicity as a surrogate biomarker to quantitatively measure the level of persisting disease activity. If disease activity persists above an acceptable level, the clinician would consider increasing the treatment dose, or changing to a different therapeutic agent.

Kits

For use in the diagnostic applications described herein, kits are also within the scope of the invention. Such kits can comprise a carrier, package or container that is compartmentalized to receive one or more containers such as vials, tubes, and the like, each of the container(s) comprising one of the separate elements to be used in the method. The antibodies of the kit may be provided in any suitable form, including frozen, lyophilized, or in a pharmaceutically acceptable buffer such as TBS or PBS. The kit may also include other reagents required for utilization of the reagents in vitro or in vivo such as buffers (i.e., TBS, PBS), blocking agents (solutions including nonfat dry milk, normal sera, Tween-20 Detergent, BSA, or casein), and/or detection reagents (i.e., goat anti-mouse IgG biotin, streptavidin-HRP conjugates, allophycocyanin, B-phycoerythrin, R-phycoerythrin, peroxidase, fluors (i.e., DyLight, Cy3, Cy5, FITC, HiLyte Fluor 555, HiLyte Fluor 647), and/or staining kits (i.e., ABC Staining Kit, Pierce)). The kits may also include other reagents and/or instructions for using antibodies and other reagents in commonly utilized assays described above such as, for example, flow cytometric analysis, ELISA, immunoblotting (i.e., western blot), in situ detection, immunocytochemistry, immunohistochemistry.

In one embodiment, the kit provides the reagent in purified form. In another embodiment, the reagents are immunoreagents that are provided in biotinylated form either alone or along with an avidin-conjugated detection reagent (i.e., antibody). In another embodiment, the kit includes a fluorescently labeled immunoreagent which may be used to directly detect antigen. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific application, and can also indicate directions for use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1: Intestinal Mucosal Inflammation Leads to Systemic Genotoxicity in Mice This example demonstrates that genotoxicity is elicited systemically by acute and chronic intestinal inflammation. In this study, genotoxic endpoints were assessed in peripheral leukocytes (DNA single and double strand breaks and oxidative DNA damage) and normochromatic erythrocytes (micronuclei) during chemical or immune-mediated colitis. During three consecutive cycles of intestinal inflammation induced by dextran sulfate sodium (DSS) administration, genotoxicity to peripheral leukocytes and erythroblasts was detected in both acute and chronic phases of DSS-induced inflammation. Reactive oxygen species mediated oxidative stress and DNA damage was confirmed with positive 8-oxoguanine and nitrotyrosine staining in peripheral leukocytes. Levels of DNA damage generally decreased during remission and increased during treatment, correlating with clinical symptoms and systemic inflammatory cytokine levels. In $G\alpha i2^{-/-}$ and $IL-10^{-/-}$ transgenic mice susceptible to immune-mediated colitis and inflammation-associated adenocarcinoma, similar levels of peripheral leukocyte and erythroblast genotoxicity were also observed. Moreover, this systemic genotoxicity was observed in mice with subclinical inflammation, which was further elevated in those with severe mucosal inflammation. We propose that mucosal inflammation, by eliciting substantial and ongoing systemic DNA damage, contributes early on to genetic instability necessary for progression to IBD-associated dysplasia and the development of cancer.

Methods

Animals.

C57BL/6Jp$^{un}$/p$^{un}$ (3 to 4 months), $G\alpha i2^{-/-}$ (B6/129Sv background, 3 months) (9) and $IL-10^{-/-}$ (C3H/HeJBir background, 3 or 6 months) were housed in the UCLA Department of Laboratory and Animal Medicine under specific pathogen free conditions, autoclaved bedding and food, with standard rodent chow diet, acidified drinking water, and 12:12 light:dark cycle. All mice were bred at UCLA except $IL-10^{-/-}$ and C3H/HeJ which were purchased from Jackson Laboratory (Bar Harbor, Me.).

Induction of Chemical Colitis.

Experimental colitis was induced with 3% (w/v) DSS (Fisher Scientific, MW 40,000) dissolved in acidified drinking water (changed daily) ad libitum for 3 cycles. One cycle consisted of 7 days of treated water followed by 14 days of normal drinking water. Acute colitis was defined as a 7 day treatment, and chronic colitis as any further treatment including remission periods. Control animals received sterile acidified water only. Symptoms (weight loss, stool consistency, gross bleeding) were recorded daily for calculation of disease activity index (23).

Blood Collection.

Peripheral blood was collected from experimental mice via the facial/mandibular vein with a 5 mm lancet (Braintree Scientific, Braintree, Mass.) into EDTA coated collection tubes (Braintree Scientific). For the comet assay, blood was immediately diluted 1:1 in PBS/10% DMSO and frozen at −80° C. until further analysis. Freshly collected blood was immediately processed for all other assays. Identical blood samples were used for genotoxic endpoints as well as for cytokine expression.

Alkaline Comet Assay.

To detect single and double strand breaks, as well as alkali labile sites in DNA, the alkaline comet assay was performed as described previously (24). Frozen blood was further diluted 1:15 in PBS before further preparation. After lysis and electrophoresis, gels were stained with SYBR Gold (Molecular Probes) and visualized under a fluorescent microscope (Olympus Ax70, Tokyo, Japan) at 10× magnification. Comet images were analyzed with the CASP image analysis program (http://casp.sourceforge.net). The olive tail moment, which represents both tail length and fraction of DNA in the tail, was used for data collection and analysis, in which apoptotic cells were excluded under previously proposed criteria (24).

Determination of Oxidative DNA Damage.

The enzyme hOgg1-modified comet assay was used for determination of oxidative DNA damage (25). Following lysis, samples were washed in an enzyme wash buffer (40 mM HEPES, 0.1M KCl, 0.5 mM EDTA, 0.2 mg/ml BSA, pH 8.0) then incubated at 37° C. for 10 min in either control (buffer with no hOGG1) or enzyme treated (buffer with hOGG1) solutions according to the manufacturer's recommendations. (New England Biolabs, Ipswich, Mass.). Both control and enzyme treated gels were then placed in electrophoresis buffer and processed identically to the alkaline comet assay.

Immunofluorescence.

Peripheral blood was incubated in Buffer EL (Qiagen, Valencia, Calif.) on ice to remove erythrocytes. Samples were then processed on coverslips essentially as described elsewhere (26). Briefly, after fixation, permeabilization, and blocking, cells were incubated with mouse anti-phospho-Histone H2A.X 5139(P) at 1:400, mouse anti-8-oxoguanine clone 413.5 at 1:250, or rabbit anti-nitrotyrosine at 1:200 (all from Upstate, Temecula, Calif.) followed by FITC-conjugated anti-mouse IgG or Rhodamine-conjugated anti-rabbit IgG (Jackson ImmunoResearch, West Grove, Pa.) at 1:200. Coverslips were mounted with VECTASHIELD with 4,6-diamidino-2-phenylindole (Vector Laboratories, Burlingame, Calif.). Images were captured with CytoVision® (Applied Imaging Corporation, San Jose, Calif.) connected to a Zeiss Axioplan 2 microscope. At least 125 cells were counted and cells with more than four distinct foci in the nucleus were considered positive for γ-H2AX (26). Apoptotic cells, which are distinguishable due to presence of 10-fold the number of nuclear foci in damaged cells (27), were not included in analyses.

Paraffin sections (5 μm) of colons from IL-10$^{-/-}$ and wildtype controls were microwaved in 10 mM citrate buffer (pH 6) for 10 min for antigen retrieval, blocked, then incubated with anti-8-oxoguanine or anti-nitrotyrosine followed by secondary antibodies identical to the procedures described above.

In Vivo Micronucleus Assay.

Micronuclei (MN) formation was determined in peripheral blood erythrocytes to assess chromosomal instability. Similar to a previously proposed method (28), 3 μl of whole blood was spread on a microscope slide and stained in Modified Wright-Giemsa solution (Sigma-Aldrich, St. Louis, Mo.). MN were counted and scored with an Olympus Ax70 (Tokyo, Japan) at 100× following previously proposed criteria (29). At least 4000 mature erythrocytes were counted per mouse, and the frequency of MN formation was calculated as number of micronucleated erythrocytes per 1000 normochromatic erythrocytes.

RNA Isolation and Quantitative Real-Time PCR.

Total RNA was isolated using QiaAmp RNA Blood Mini Kit (Qiagen) according to manufacturer's instructions. 25 ng/μl of total RNA was used for reverse transcription using OligodT (Invitrogen) and Superscript III Reverse Transcriptase (Invitrogen). 10 ng/μl of cDNA was used for quantitative real time PCR using Taqman Gene Expression Assays (Applied Biosystems, Foster City, Calif. p/n 4331182) for Tbp (TATA binding protein), TNF-α (tumor necrosis factor α), MCP-1 (monocyte chemoattractant protein 1, also known as CC chemokine ligand 2, CCL2), IFN-γ (interferon γ), TGF-β (tumor growth factor β) and Taqman Gene Expression Master Mix according to manufacturer's instructions on the ABI Prism 7500 sequence detection system (Applied Biosystems). Tbp was chosen as the endogenous control due to its low variability and low to medium relative abundance in terms of expression in blood (30). Each measurement was performed in triplicate and results were analyzed using SDS 2.2.1 software (Applied Biosystems). Gene expression was determined using the relative standard curve method normalized to Tbp expression.

Statistical Analyses.

Results are expressed as mean±standard error of the mean. Statistical significance was determined by nonparametric one way ANOVAs with Dunn's multiple comparison post test or a paired Student's t-tests with log-transformed data for time point comparisons, and defined as $p<0.05$. ANOVAs of linear regression models were used as appropriate. Calculations were performed with the statistical analysis software GraphPad Instat version 3.00 (GraphPad Software, San Diego, Calif.) or R: A language and environment for statistical computing. (R Development Core Team (2007). R Foundation for Statistical Computing, Vienna, Austria. ISBN 3-900051-07-0, URL http://www.R-project.org).

Results

Evaluation of Experimental Colitis.

The disease activity index (DAI) is the average combined score of weight loss (0-4), stool consistency (0-4), and bleeding (0-4), used to score clinical symptoms (23). DSS-treated mice demonstrated rectal bleeding starting day 4 in cycle 1, represented by the increase in the DAI compared to non-treated animals (FIG. 1). However, the onset of severe symptoms came earlier in the second and third cycles of treatment due to chronic inflammation, even after 14 day remission periods. Bleeding and diarrhea ceased as soon as treatment was stopped during remission and no mortalities were observed after three cycles of treatment. Food intake was also not affected throughout the study and significant weight loss was only apparent during the end of the second and third cycle.

DSS Treatment Causes DNA Single and Double Strand Breaks in Peripheral Leukocytes.

Figure 2:
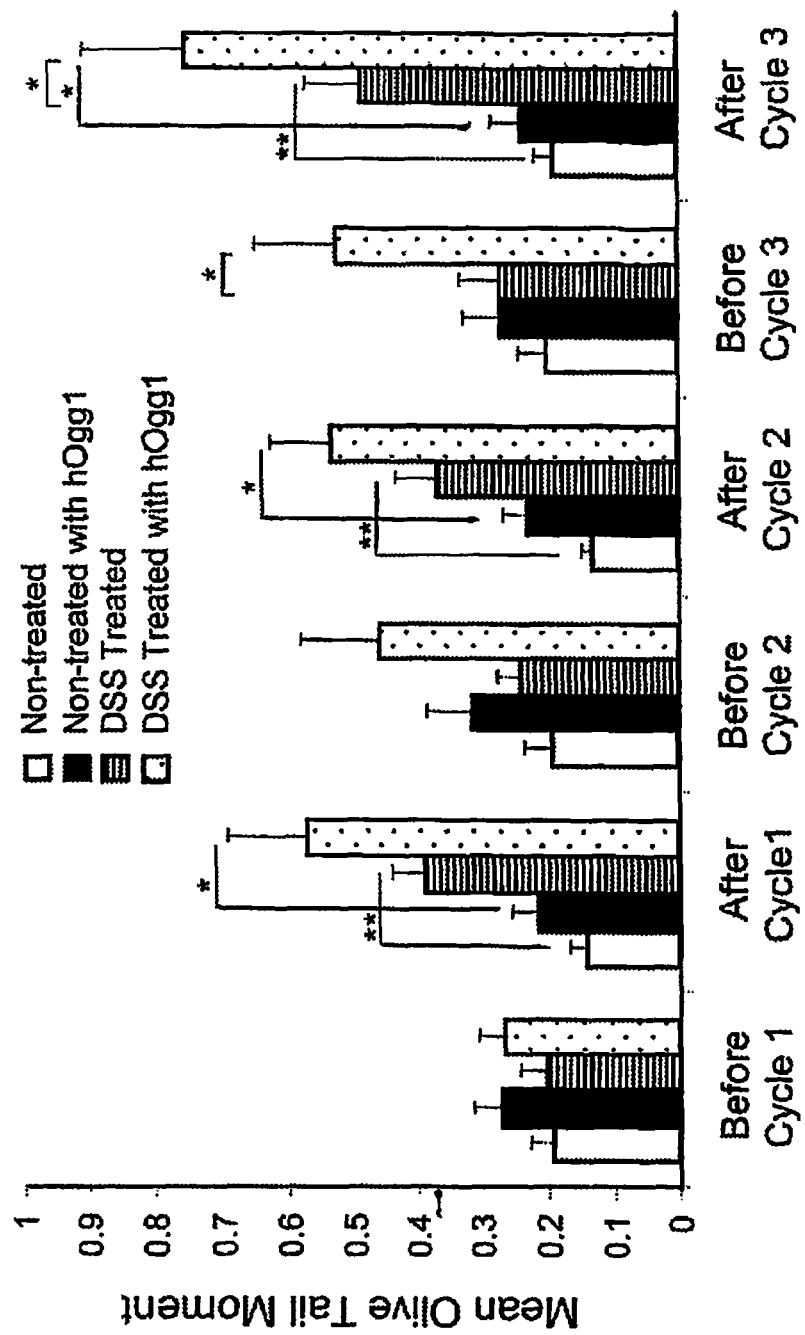
FIG. 2. Mean Olive Tail Moments. At least 150 "comets" were scored per mouse in the DSS treated group (n=10) and in the non-treated group (n=10). Data were log transformed before applying statistical tests, and are represented as mean±SEM. *: p<0.05, **: p<0.01.

Single and double strand breaks as well as alkali-labile sites in DNA of peripheral leukocytes were measured in terms of the mean olive tail moment with the alkaline comet assay (FIG. 2). While mean olive tail moments of non-treated mice remained low throughout each cycle of treatment, DSS treated mice demonstrated significantly higher olive tail moments at the end of each cycle ($p<0.01$). After each remission period of 14 days, levels of DNA damage decreased most likely due to DNA repair. The hOgg1 modified alkaline comet assay was also used to detect oxidative base damage. Ogg1 primarily recognizes and removes 8-oxoguanine through a base excision repair pathway, as well as 8-oxoadenine, fapy-guanine, and methyl-fapy-guanine (31). Mean olive tail moments were higher when incubated with hOgg1 after treatment cycles in treated mice compared to hOgg1 incubated non-treated mice ($p<0.05$), indicating presence of oxidized base damage. When compared to levels before cycle 1, hOgg1 incubated DNA from DSS-treated mice were significantly higher at every following time point ($p<0.01$). Levels of DNA damage increased with each treatment cycle especially when including oxidative base damage, indicating damaging effects of acute and more significantly, chronic inflammation. A small number of apoptotic cells with extensive DNA fragmentation were apparent after treatment cycles, however were not included in calculation of mean olive tail moments.

Presence of DNA double strand breaks alone was confirmed with immunofluorescence of γ-H2AX (FIG. 3A). In response to double strand breaks, histone 2AX is phosphorylated (γ-H2AX) in a 2-Mbp region flanking the double strand break within 15 minutes (27). Percentage of cells positive for nuclear foci increased dramatically in the DSS treated group after the first 7 day acute treatment ($p<0.01$) compared to non-treated animals. Although not as dramatic, percent positive cells remained elevated over non-treated animals until end of treatment ($p<0.05$). Efficient DNA double strand break repair may be activated, decreasing the presence of foci in chronic inflammation due to the severely damaging nature of double strand breaks compared to oxidative base damage or single strand breaks.

DSS-Induced Inflammation is Clastogenic to Erythroblasts.

The in vivo micronucleus (MN) assay was carried out in mature normochromatic erythrocytes circulating in the peripheral blood to determine chromosomal damage to erythroblasts (FIG. 3B). The incidence of micronuclei is commonly used as an index of cytogenetic damage, including chromosome breaks, spindle abnormalities, or structurally abnormal chromosomes; most frequently in erythroblasts/erythrocytes from peripheral blood or bone marrow (29). Mature micronucleated normochromatic erythrocytes represent the final developmental stage of erythroblasts containing micronuclei stemming in the bone marrow, and thus permit the study of both the generation and elimination of micronucleated erythrocytes (32).

Micronucleus formation was significantly induced after the first cycle of treatment in DSS treated animals ($p<0.01$) compared to non-treated animals, and was further induced after the second and third cycles compared to both non-treated animals, and levels before cycle 1 ($p<0.01$). Similar to patterns seen in the results of the alkaline comet assay, micronuclei formation decreased after remission periods, and increased after each cycle of treatment. This indicates clearance of micronucleated erythrocytes by the spleen followed by induction during treatment periods. Starting at the before cycle 3 time point, micronucleated erythrocyte levels were slightly elevated even in non-treated animals, most likely due to the effects of repeated blood draws and consequentially high rate of erythropoiesis.

DSS Treatment Modulates mRNA Expression of Cytokines in Peripheral Blood.

Systemic inflammation due to DSS treatment was demonstrated by cytokine gene expression in the peripheral blood of treated animals. Leukocytes circulating in the periphery mounted a strong Th1 response characterized by up-regulation of TNF-α, MCP-1 (CCL2), and IFN-γ particularly after the first cycle of treatment (FIG. 4). TNF-α transcript levels followed DNA damage patterns of increasing after each 7 day treatment cycle, then decreasing after each 14 day remission period. MCP-1 and IFN-γ transcript levels increased after the first cycle, then decreased after the remission period, where they remained low until rising once again in the third cycle; demonstrating a delayed secondary induction compared to TNF-α. TGF-β, an anti-inflammatory cytokine, was also modulated similarly to MCP-1 and IFN-γ. DSS treatment induces both a Th1 response as well as an anti-inflammatory response over the acute and chronic phases of treatment in the peripheral blood.

DNA Damage is Observed in Genetic Models of Mucosal Inflammation.

Figure 5A:
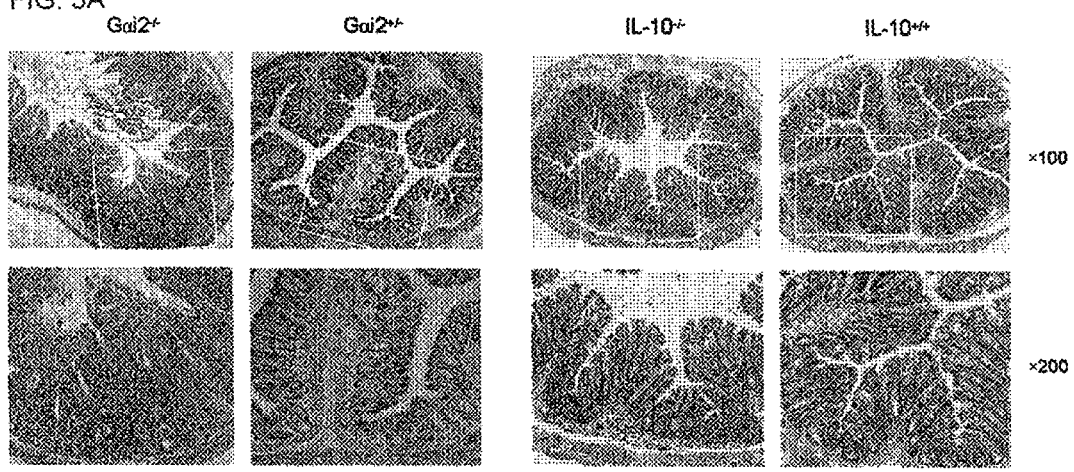
FIGS. 5A-5D. Systemic Genotoxicity in Mouse Models of Mucosal Inflammation. Blood was sampled from Gαi2$^{-/-}$, IL-10$^{-/-}$, and control IL-10$^{+/+}$ mice for genotoxicity assays at age 3 months; in addition, IL-10$^{-/-}$ mice were sampled at age 6 months, when colitis in this genetic background has progressed to greater clinical activity.
Figure 5B:
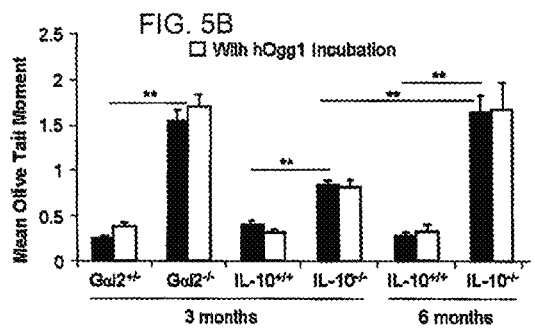
Figure 5C:
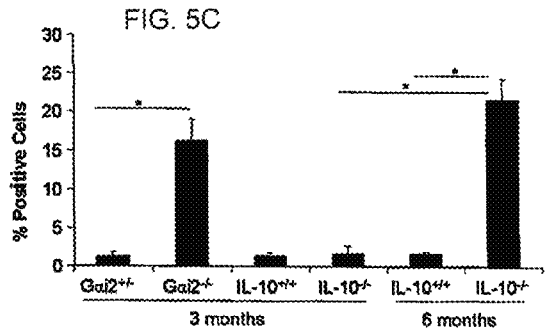
Figure 5D:
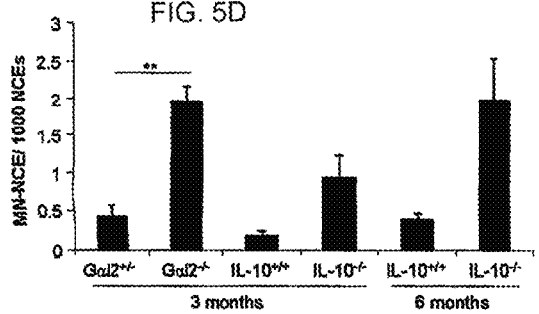

In order to further determine whether systemic genotoxicity is a general consequence of colitis, we measured DNA damage in two genetic models of mucosal inflammation without the use of DSS. We examined $G\alpha i2^{-/-}$ mice at age 3 months (chronic active inflammation with neoplastic changes in colon), and IL-10$^{-/-}$ at age 3 and 6 months (in which mice have subclinical disease with minimal histologic inflammation, and active disease and inflammation with mild epithelial hyperplasia, respectively) (FIG. 5A). Single and double DNA strand breaks were significantly higher ($p<0.01$) in both $G\alpha i2^{-/-}$ mice compared to age-matched $G\alpha i2^{+/-}$ mice without clinical symptoms and in IL-10$^{-/-}$ mice with sub-clinical inflammation compared to age-matched IL-10$^{+/+}$ mice using the comet assay (FIG. 5B). We then hypothesized that IL-10$^{-/-}$ mice with severe mucosal inflammation would have greater DNA damage than those with sub-clinical inflammation. These mice indeed demonstrated higher levels of strand breaks than IL-10$^{-/-}$ mice with sub-clinical inflammation ($p<0.01$), comparable to those seen in $G\alpha i2^{-/-}$ mice. Oxidative base damage, however, seemed only apparent in $G\alpha i2$ mice as measured by hOgg1 incubation. DNA double strand breaks measured by γ-H2AX immunofluorescence (FIG. 5C) were also elevated in both $G\alpha i2^{-/-}$ and IL-10$^{-/-}$ compared to $G\alpha i2^{+/-}$ and IL-10$^{+/+}$ mice, respectively, though only statistically significant in $G\alpha i2^{-/-}$ mice ($p<0.05$), and in IL-10$^{-/-}$ mice with severe mucosal inflammation ($p<0.05$). Finally, micronucleus induction in erythroblasts were also significantly elevated in $G\alpha i2^{-/-}$ mice compared to $G\alpha i2^{+/-}$ mice ($p<0.01$), and elevated but not statistically significantly elevated in IL-10$^{-/-}$ versus IL-10$^{+/+}$ mice (FIG. 5D). Systemic genotoxicity can therefore be incurred by several modes of inflammation, independent of DSS administration.

Intestinal Inflammation Induces ROS Mediated Oxidative Stress and DNA Damage.

To determine potentially causative species of oxidative stress due to intestinal inflammation, peripheral leukocytes from DSS treated mice (7 days, 3% w/v) and IL-10$^{-/-}$ mice (6 months) were isolated and stained for 8-oxoguanine or nitrotyrosine (FIGS. 6A and B). 8-oxoguanine is an oxidative DNA lesion formed by reaction of hydroxyl radicals, metal hyrdroperoxides, or peroxynitrite with DNA, causing G:C to T:A transversions during replication (33). Nitrotyrosine is a biochemical marker for NO-induced peroxynitrite formation involving reactions with reactive oxygen and nitrogen species resulting in nitrative damage to proteins (34). DSS-induced inflammation caused a significant increase in both 8-oxoguanine and nitrotyrosine ($p<0.01$) in peripheral leukocytes, as did those isolated from IL-10$^{-/-}$ mice ($p<0.05$). Colon sections from IL-10$^{-/-}$ mice also demonstrated 8-oxoguanine residues mostly in the nuclei of the surface epithelial cells as well as in infiltrating inflammatory cells within or near the lamina propria as "focus" like or pan-nuclear staining (FIG. 6C). Nitrotyrosine residues were also present in the cytoplasm of epithelial cells and inflammatory cells, whereas no immunoreactivity was observed in wildtype mice.

Discussion

Previous studies have established the role of inflammation-derived oxidative DNA damage to inflammatory and surrounding epithelial cells only at the localized sites of inflammation in the colon. Our study demonstrates for the first time that this damage extends beyond the site of inflammation to circulating leukocytes and erythroblasts in the bone marrow, manifesting a systemic effect, and correlating to oxidative damage found in inflammatory tissue. Genotoxicity to peripheral leukocytes was evident in terms of both single and double strand breaks to DNA accompanied by oxidative base damage while chromosomal aberrations took place in erythroblasts. Such findings were observed both in acute and chronic phases of chemical colitis induced by DSS administration, and in untreated G$\alpha$i2$^{-/-}$ and IL-10$^{-/-}$ mice undergoing spontaneous immune colitis. Moreover, in IL-10$^{-/-}$ mice, which are notable for a delayed onset of colitis, genotoxicity was further elevated in mice which had proceeded to a state of clinically active colitis versus those with sub-clinical inflammation. Markers of reactive oxygen species (ROS) derived oxidative stress demonstrated presence of 8-oxoguanine and nitrotyrosine in peripheral leukocytes of DSS treated mice and IL-10$^{-/-}$ mice, representing possible mechanisms of genotoxicity and correlating to oxidative damage seen in the colon. Accordingly, the present study reveals that systemic genotoxicity is a prevalent feature of subclinical, acute, and chronic colitis.

In DSS-treated mice, repair of DNA damage was observed during remission periods, represented by a decrease in damage markers. However, the extent of repair appeared slightly less in the last remission due to increasing severity of chronic inflammation. Despite increasing severity of inflammation, double strand breaks remained only slightly elevated over non-treated animals, which may imply efficient repair in comparison to single strand breaks and oxidative damage. DSS administration also induced systemic distribution of cytokines, as evidenced by modulation of transcript levels in peripheral blood. Interestingly, TNF-$\alpha$ was up-regulated during treatment, and down-regulated during remission, mirroring patterns seen in genotoxicity to leukocytes. Similar to previous cytokine studies in the colons of DSS treated mice (20), features of both Th1 and Th2 activity were observed systemically in the peripheral blood, leading to chronic activation of immune cells. The decrease in MCP-1 and IFN-$\gamma$ expression after the first cycle of treatment may be explained by a shift towards higher expression of Th2 cytokines and a decrease in selective Th1 cytokines, as recently documented (35) in DSS treated mice. Chronic DSS treatment mimics IBD with similar cytokine profiles demonstrating dysregulated and imbalanced immunologic responses to commensal bacterial antigens. Dysregulated and polarized cytokine production play key roles in enhancing chronic inflammation and tumorigenesis through signaling release of pro-tumor mediators (36).

The present study shows that both chemical and genetic/immune models of inflammation-mediated carcinogenesis not only parallel the inflammation to dysplasia to cancer sequence of human IBD, but also manifest inflammation-associated oxidative stress in the colon as seen in UC and Crohn's disease. Unlike other colitis-associated neoplasia models utilizing genotoxic colon carcinogens as initiators of neoplasia (azoxymethane or 1,2-dimethylhydrazine), DSS itself is not a mutagen nor genotoxic (37). However, it has been shown to both directly and indirectly activate macrophages and other inflammatory cells (16, 38), a central feature of genetic models of immune colitis (8-11). Thus, carcinogenesis arising in these settings is solely a manifestation of chronic inflammation. The prominent mucosal and systemic activation of macrophages, neutrophils, eosinophils, and other effectors in DSS-induced colitis, genetic immune colitis (and in active disease of patients with IBD) is a potential source of oxidative stress. This may cause oxidative and nitrative damage locally through oxidative burst, and through release of cytokines that induce receptor-mediated reactive oxidative species production by target cells. Microsatellite instability was identified in tumors in colons of DSS-treated wildtype mice, and more so in Msh2$^{-/-}$ mice (39). DSS treatment also induced 8-oxoguanine residues in mouse colonic mucosa (22), suggesting oxidative damage directly at the site of inflammation. Notably, this observed systemic genotoxicity is a secondary effect of DSS treatment, namely the consequence of systemic inflammation and inflammation-associated oxidative stress. In agreement with these findings, we have demonstrated 8-oxoguanine and nitrotyrosine formation in the surface epithelium and inflammatory infiltrate of IL-10$^{-/-}$ colons as well as in peripheral blood of IL-10$^{-/-}$ and DSS treated wildtype mice, indicating systemic presence of peroxynitrite and reactive oxygen and nitrogen species.

We envision two, non-exclusive processes linking local inflammation and systemic genotoxicity. First, locally activated innate immune cells may release reactive species inducing formation of other reactive species such as hydroxyl radicals and NO-derived peroxynitrite, damaging emigrating resident leukocytes, that then circulate into the periphery. Alternatively, inflammatory cytokines achieve biologically significant systemic levels, upon which they induce autonomous, cytokine-receptor mediated production of free radicals (and genotoxic damage) in remote leukocyte populations. Both scenarios are possible, as we observed pro-inflammatory cytokines throughout DSS treatment in the peripheral blood, and oxidative DNA damage and nitrotyrosine formation in circulating leukocytes. Similarly, micronucleus formation in the erythroblasts of the bone marrow in our study may have been a result of activated T-cells that are part of the normal recirculating lymphocyte pool circulating into the bone marrow, and leading to oxidative damage. Accumulation of single and double strand breaks can sequentially lead to chromosome breaks and micronuclei formation (40).

In addition, biologic processes affected by inflammation may also determine the fate of cells bearing genotoxic damage. Since inflammatory mediators elicit both epithelial cell proliferation and anti-apoptotic signals, epithelial cells in chronic inflammation are at particular risk to DNA damage leading to fixation of mutations that may not be properly repaired and removed (22). In DSS colitis, oxidative DNA damage was positively correlated with apoptosis in the small intestine but not the large intestine (41). This biologic difference may contribute to the relative susceptibility to cancer progression in the large intestine. While the mechanism of this differential induction of apoptosis is uncertain, genotoxic stress induces expression of ligands for the NKG2D receptor (42). This receptor is differentially expressed on resident CD8$^+$ T cells and natural killer cells of the small versus large intestine, and is a potent inducer of anti-epithelial cytotoxicity in this intestinal region (43). Finally, the possibility of reciprocal regulation of inflammation and DNA repair pathway elements is an emerging area of investigation (44).

In summary, intestinal inflammation is associated with systemic genotoxicity through single and double DNA strand breaks, oxidative DNA damage, protein nitration, and micronucleus formation. We propose that elements of the inflammatory response including ROS derived oxidative stress are responsible for the observed systemic genotoxicity. Previous studies have observed oxidative base damage, microsatellite instability, and gene mutations directly in the colonic mucosa of both human IBD and experimental murine colitis. Here, we highlight that systemic DNA damage accompanied by systemic inflammation is an early event involved in the promotion of genetic instability. Such systemic genotoxicity may be a biologically relevant and sensitive biomarker of one process contributing to inflammation-associated carcinogenesis.

REFERENCES CITED IN EXAMPLE 1

1. Loftus E V. Gastroenterology 2004; 126(6):1504-17.
2. Ekbom A, Helmick C, Zack M, Adami H O. N Engl J Med 1990; 323(18):1228-33.
3. Xie J, Itzkowitz S H. World J Gastroenterol 2008; 14(3):378-89.
4. Chu F F, et al. Cancer Res 2004; 64(3):962-8.
5. Maggio-Price L, et al. Am J Pathol 2005; 166(6):1793-806.
6. An G, Wei B, Xia B, et al. J Exp Med 2007; 204(6):1417-29.
7. Greten F R, et al. Cell 2004; 118(3):285-96.
8. Beatty P L, Plevy S E, Sepulveda A R, Finn O J. J Immunol 2007; 179(2):735-9.
9. Rudolph U, et al. Nat Genet. 1995; 10(2):143-50.
10. McPherson M, et al. Am J Physiol Gastrointest Liver Physiol 2008.
11. Nemetz N, et al. Int J Cancer 2008; 122(8):1803-9.
12. Popivanova B K, et al. J Clin Invest 2008; 118(2):560-70.
13. O'Mahony L, et al. Aliment Pharmacol Ther 2001; 15(8):1219-25.
14. Erdman S E, et al. Am J Pathol 2003; 162(2):691-702.
15. Takedatsu H, et al. Gastroenterology 2008.
16. Okayasu I, et al. Gastroenterology 1990; 98(3):694-702.
17. Cooper H S, et al. Carcinogenesis 2000; 21(4):757-68.
18. Lennard-Jones J E, et al. Gut 1990; 31(7):800-6.
19. Dieleman L A, et al. Gastroenterology 1994; 107(6):1643-52.
20. Dieleman L A, et al. Clin Exp Immunol 1998; 114(3):385.
21. Ohkusa T, et al. Digestion 1995; 56(2):159-64.
22. Meira L B, et al. J Clin Invest 2008; 118(7):2516.
23. Murthy S N, et al. Dig Dis Sci 1993; 38(9):1722-34.
24. Olive P L, Banath J P. Nat Protocols 2006; 1(1):23-9.
25. Smith C C, et al. Mutagenesis 2006; 21(3):185-90.
26. Goldstine J V, et al. DNA Repair 2006; 5(4):432-43.
27. Muslimovic A, et al. Nat Protocols 2008; 3(7):1187.
28. Schmid W. The micronucleus test for cytogenetic analysis. Chemical mutagens Principles and methods for their detection New York:Plenum 1976:31-53.
29. Hayashi M, et al. Mutat Res 1994; 312(3):293-304.
30. Lossos I S, et al. Leukemia; 17(4):789-95.
31. Bjoras M, et al. EMBO J. 1997; 16(20):6314-22.
32. Steinheider G, et al. Cell Biol Toxicol 1986; 2(1):197-211.
33. Pinlaor S, et al. Carcinogenesis 2004; 25(8):1535-42.
34. Liu J S, et al. Am J Pathol 2001; 158(6):2057.
35. Alex P, et al. Inflamm Bowel Dis 2009; 15(3):341-52.
36. Johansson M, et al. Immunol Rev 2008; 222(1):145-54.
37. Mori H, et al. Nutr Cancer 1984; 6(2):92-7.
38. Shintani N, et al. Scand J Immunol 1997; 46(6):581-6.
39. Kohonen-Corish M R J, et al. Cancer Res 2002; 62(7):2092-7.
40. Obe G, et al. Mutat Res 2002; 504(1-2):17-36.
41. Hong M Y, et al. Exp Biol Med 2005; 230(7):464-71.
42. Gasser S, et al. Nature 2005; 436(7054):1186-90.
43. Meresse B, et al. J Exp Med 2006; 203(5):1343.
44. Coscoy L, Raulet D H. Cell 2007; 131(5):836-8.

Example 2: Elevated DNA Damage and Persistent Immune Activation in Atm Deficient Mice with Dextran Sulfate Sodium-Induced Colitis This example describes the systemic DNA damage and immune response to induced experimental colitis in mice deficient in ATM, a DNA double-strand break recognition and response protein. To determine the effect of Atm deficiency in inflammation, we induced experimental colitis in Atm$^{-/-}$, Atm$^{+/-}$ and wildtype mice via dextran sulfate sodium (DSS) administration. Atm$^{-/-}$ mice had higher disease activity indices and rates of mortality compared to heterozygous and wildtype mice. Systemic DNA damage and the immune response were characterized in peripheral blood throughout and after three cycles of treatment. Atm$^{-/-}$ mice demonstrated increased sensitivity to levels of DNA strand breaks in peripheral leukocytes, as well as micronuclei formation in erythroblasts compared to heterozygous and wildtype mice, especially during remission periods and after the end of treatment. Markers of reactive oxygen and nitrogen species-mediated damage, including 8-oxoguanine and nitrotyrosine were present in both the distal colon and in peripheral leukocytes, with Atm$^{-/-}$ mice manifesting more 8-oxoguanine formation than wildtype mice. Atm$^{-/-}$ mice demonstrated greater upregulation of inflammatory cytokines, and significantly higher percentages of activated CD69$^+$ and CD44$^+$ T-cells in the peripheral blood throughout treatment. ATM therefore may be a critical immunoregulatory factor dampening the deleterious effects of chronic DSS-induced inflammation, necessary for systemic genomic stability and homeostasis of the gut epithelial barrier.

Methods

Animals.

Adult Atm$^{-/-}$ mice crossed into the parental C57BL/6J p$^{un}$/p$^{un}$ background as previously described (18), heterozygous (Atm$^{+/-}$ p$^{un}$/p$^{un}$), and wildtype control mice (Atm$^{+/+}$ p$^{un}$/p$^{un}$), 12 to 16 weeks old, were housed in a specific pathogen free facility fed a standard rodent chow diet, provided acidified drinking water, and 12:12 light:dark cycle. Food, bedding, and water were autoclaved. All experimental procedures were in accordance with the UCLA Animal Research Committee guidelines.

Induction of Experimental Colitis.

Acute and chronic experimental colitis was induced by administering 3% (w/v) DSS (MP Biomedicals, MW 40,000) dissolved in sterile acidified drinking water ad libitum for 3 cycles. One cycle of treatment consisted of 7 days of treated water followed by 14 days of normal drinking water. Water was changed daily and symptoms including weight loss, stool consistency, and gross bleeding were also recorded for calculation of the disease activity index (DAI), as described further elsewhere (19). Briefly, a score ranging from 0-4 was assigned for each measure (weight loss (0-15% loss), stool consistency (normal to diarrhea), and blood in stool (no blood to gross bleeding)), and the average of these scores was recorded as the DAI. Mice were monitored for 31 days after the end of treatment.

Blood Collection.

Peripheral blood was collected via the mandibular vein with a 5 mm lancet (Braintree Scientific, Braintree, Mass.) into EDTA coated tubes (Braintree Scientific). Blood was collected before and right after each seven day treatment of DSS, for three cycles and at two and four weeks after the end of the three cycles. For the comet assay, blood was immediately diluted 1:1 in RPMI/10% DMSO and immediately frozen at −80° C. until further analysis. Freshly collected blood was immediately processed for all other assays. Identical samples were used for genotoxicity endpoints as well as for cytokine expression or flow cytometry, allowing each animal to serve as its own control.

Alkaline Comet Assay.

To detect DNA strand breaks, as well as alkali labile sites, the alkaline comet assay was performed and analyzed as described elsewhere (1, 20). The olive tail moment, which represents both tail length and fraction of DNA in the tail, was used for data collection and analysis, in which apoptotic cells were excluded under previously proposed criteria (20).

Determination of Oxidative DNA Damage.

The enzyme hOgg1-modified comet assay was used and carried out identically as previously described (1).

Immunofluorescence.

Peripheral blood was incubated in Buffer EL (Qiagen, Valencia, Calif.) to remove erythrocytes. Samples were then processed on coverslips and stained with anti-phospho-Histone H2A.X S139(P), mouse anti-8-oxoguanine clone 413.5, or rabbit anti-nitrotyrosine (Millipore, Temecula, Calif.) as described previously (1, 21). At least 125 cells were counted and cells with greater than four distinct foci in the nucleus were considered positive for γ-H2AX (21). Apoptotic cells, distinguishable due to the presence of 10-fold the number of nuclear foci in damaged cells (22), were not included in analyses.

Paraffin sections (5 μm) of colons from $Atm^{-/-}$ and wildtype controls were microwaved in 10 mM citrate buffer (pH 6) for 10 min for antigen retrieval, blocked, then incubated with anti-8-oxoguanine or anti-nitrotyrosine followed by secondary antibodies identical to procedures described above. Images were captured with CytoVision® (Applied Imaging, UK) and staining was quantified using ImageJ software (23).

In Vivo Micronucleus Assay.

Micronuclei (MN) formation was determined in peripheral blood erythrocytes to assess chromosomal instability as previously described (1). At least 4000 mature erythrocytes were counted per animal, and the frequency of MN formation was calculated as the number of micronucleated erythrocytes per 1000 normochromatic erythrocytes.

RNA Isolation and Quantitative Real-Time PCR.

Total RNA was isolated using QiaAmp RNA Blood Mini Kit (Qiagen) according to manufacturer's instructions. 25 ng/μl of total RNA was used for reverse transcription using OligodT (Invitrogen) and Superscript III Reverse Transcriptase (Invitrogen). 10 ng/μl of cDNA was used for quantitative real time PCR using Taqman Gene Expression Assays (Applied Biosystems, Foster City, Calif.) for TBP (TATA box binding protein), TNF-α (tumor necrosis factor-alpha), MCP-1 (monocyte chemoattractant protein-1), IFN-γ (interferon-gamma), TGF-β (transforming growth factor-beta), IL-4 (interleukin-4), IL-10 (interleukin-10), IL-6 (interleukin-6), IL-17 (interleukin-17), IL-23 (interleukin-23), IL-12 (interleukin-12) according to manufacturer's instructions on the ABI Prism 7500 sequence detection system (ABI). TBP was chosen as the endogenous control due to its low variability and low to medium relative abundance in expression in blood (24). Each measurement was performed in triplicate and results were analyzed using SDS 2.2.1 software (ABI). Quantification of gene expression was determined using the relative standard curve method normalized to TBP expression.

Flow Cytometry.

T cell populations were characterized for activation status (CD69 and CD44) and CD4 or CD8α expression using flow cytometry. Erythrocytes were immediately lysed with BD PharmLyse Lysis Buffer (BD Biosciences, San Diego, Calif.). After washing with Stain Buffer with 0.2% BSA (BD), cells were stained with FITC conjugated Hamster Anti-Mouse CD69, FITC conjugated Rat Anti-Mouse/Human CD44, R-PE conjugated Rat Anti-Mouse CD4, PerCP Rat Anti-Mouse CD8α, or appropriate negative isotype controls (BD Biosciences) for 30 min at 4° C. Cells were then washed and analyzed using BD FACScan. Fluorescence intensity was normalized to each respective isotype control antibody and data were analyzed with CellQuest® (BD Biosciences). Dead cells were excluded by gating on forward/side scatter. Marker expression was recorded either as percent positive of the absolute count of total T cells, or by median fluorescence intensity if the control and marker populations overlapped.

Statistical Analyses.

Results (error bars) are expressed as mean±standard error of the mean (SEM) with n=10 mice per genotype. Statistical significance was determined by nonparametric one-way/two-way ANOVAs with Dunn's multiple comparison post test or paired Student's t-tests with log-transformed data for time point comparisons, defined as p<0.05. ANOVAs of linear regression models were used as appropriate. Genotoxicity assays and flow cytometry were repeated twice. Calculations were performed with GraphPad Instat 3.00 (Graph Pad Software, San Diego, Calif.) or R: a language and environment for statistical computing (Vienna, Austria) (25).

Results $Atm^{-/-}$ Mice Show Elevated Sensitivity to DSS Treatment.

Figure 7:
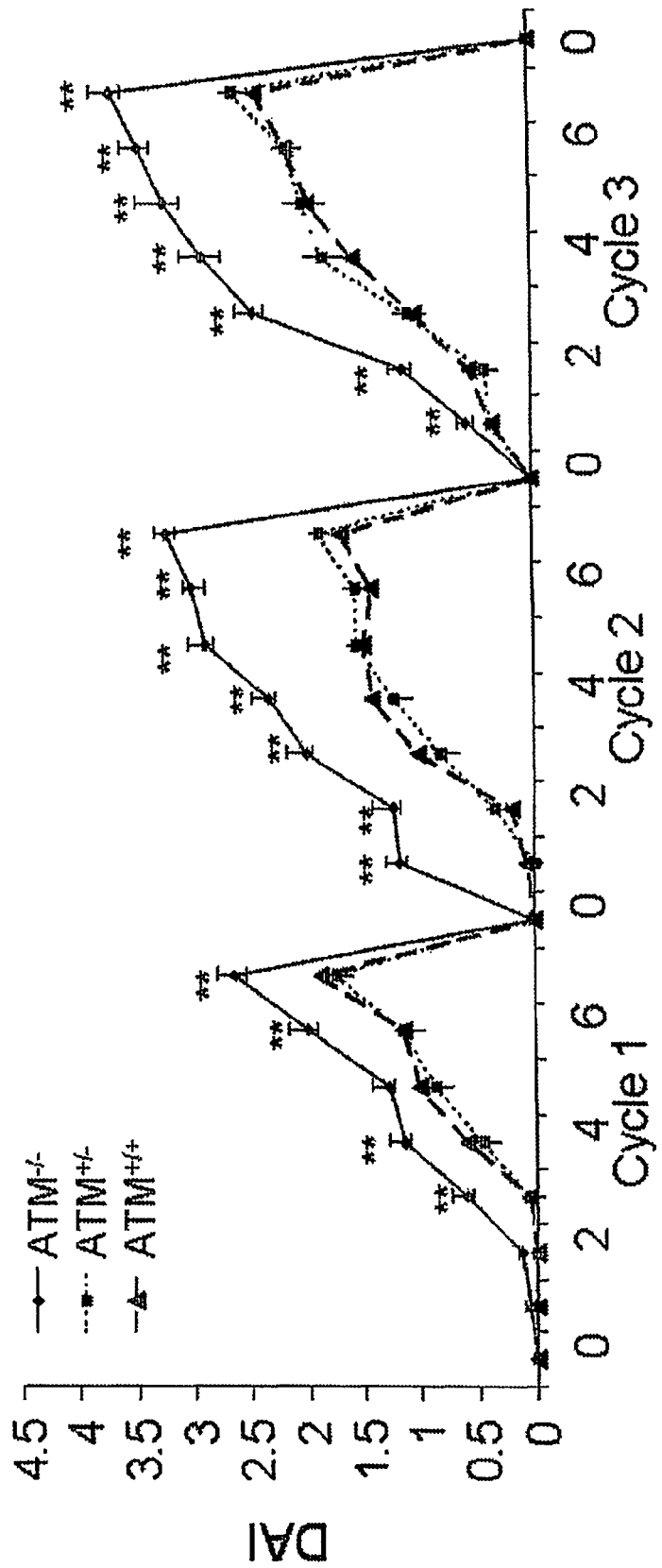
FIG. 7. Disease activity indices (DAIs) of Atm$^{-/-}$, Atm$^{+/-}$, and wildtype mice. Atm$^{-/-}$ mice exhibit higher DAIs (**: p<0.01) by Student's unpaired t-test compared to Atm$^{+/-}$ and wildtype mice. Two Atm$^{-/-}$ mice died; one at end of cycle 2, and one at end of cycle 3. Non-treated mice of all genotypes had DAIs of 0 throughout the entire study.

Mice were monitored daily for measurement of the disease activity index (DAI; an average score taking into account weight loss, stool consistency, and presence of blood in the stool, with a maximum score of 4. After an acute 7 day exposure to DSS, $Atm^{-/-}$ mice had a mildly higher disease activity index compared to wildtype and heterozygous mice (FIG. 7). Differences in symptom severity became more apparent towards the end of the second and third cycles (**: p<0.01), during chronic inflammation. Heterozygous and wildtype mice had similar DAIs throughout the study, indicating a lack of a gene dosage effect. In addition, $Atm^{-/-}$, $Atm^{+/-}$, and wildtype mice without DSS treatment had DAIs of 0 throughout the entire study, demonstrating no baseline clinical symptoms. Two out of ten $Atm^{-/-}$ mice died due to severe symptoms and rectal prolapse; one at the end of the second, and one at the end of the third cycle. All other mice survived the entire treatment. During remission periods, no signs of weight loss or persistent diarrhea were present in all genotypes. Surviving mice were also followed for four weeks after the end of the third cycle, however no symptoms were evident.

Elevated Systemic Genotoxicity in Atm$^{-/-}$ Mice.

Figure 8A:
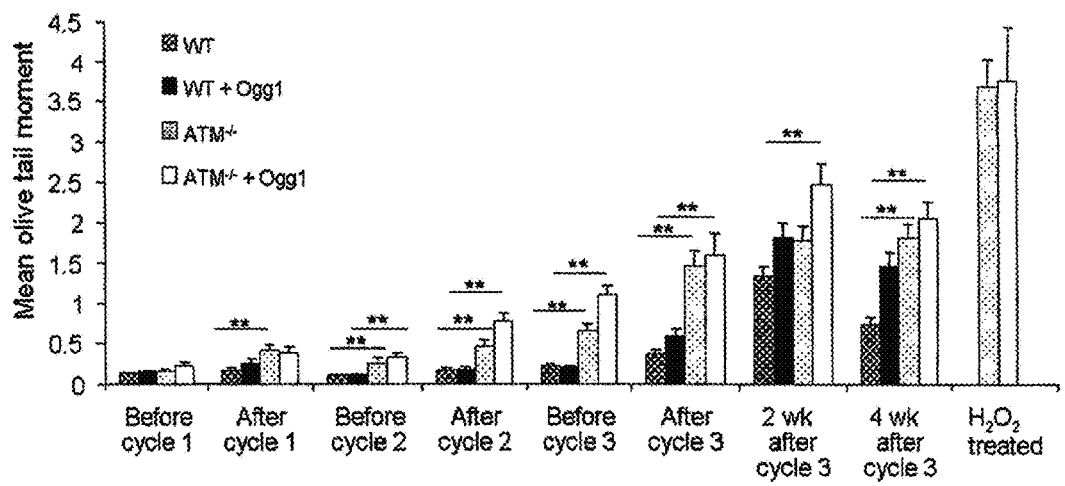
FIG. 8A. Mean olive tail moments of peripheral leukocytes with and without hOgg1 incubation. A portion of cells were treated with H$_2$O$_2$ for 20 min as a positive control. Two-way ANOVA with Dunn's multiple comparison test demonstrate significant (p<0.001) differences between genotypes.

Since Atm$^{-/-}$ mice are defective in DNA double strand break repair and have higher levels of cellular oxidative stress (26), we hypothesized that inflammation-induced DNA damage would be more pronounced. Sensitivity to treatment was therefore assessed in terms of genotoxicity to peripheral leukocytes, a systemic measure of DNA damage. DNA strand breaks as well as alkali-labile sites, represented by the olive tail moment, increased in wildtype mice after the first cycle (p<0.001) (FIG. 8A). Damage was repaired during the first remission period, and successively increased after the second cycle until 2 weeks after the last cycle of treatment, before repair of damage was seen again. Oxidative base damage, as measured by incubation with hOgg1, was not significant in wildtype mice until after the third cycle of treatment.

On the other hand, DNA strand breaks successively increased in Atm$^{-/-}$ mice with treatment, regardless of the remission periods. Olive tail moments were significantly higher in Atm$^{-/-}$ mice especially after the second and third cycles of treatment compared to wildtype mice (p<0.001). Oxidative base damage was also more apparent in Atm$^{-/-}$ mice, and more so after the end of the second cycle of treatment and up to 4 weeks after the end of the last treatment (p<0.001). Atm$^{-/-}$ mice therefore incur more DNA damage than wildtype mice, especially in chronic inflammation.

Figure 8B:
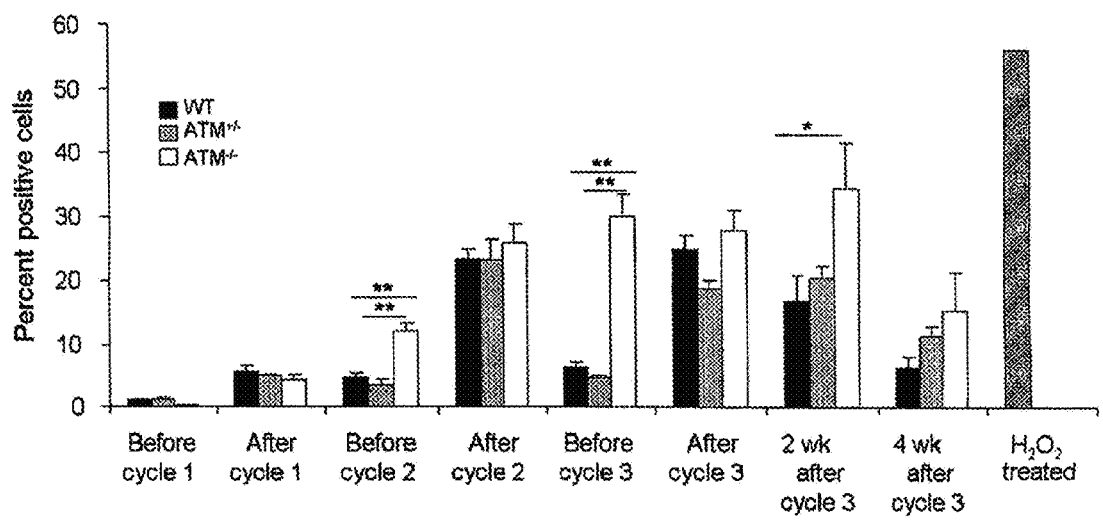
FIG. 8B. Percent positive cells for γH2AX in peripheral leukocytes of Atm$^{-/-}$, Atm$^{+/-}$, and wildtype mice. A portion of cells were treated with H$_2$O$_2$ for 20 min before staining as a positive control. Two-way ANOVA with Dunn's multiple comparison test demonstrated significant treatment effects. Genotype differences are shown *: p<0.05, **: p<0.01.

DNA double-stranded breaks alone were confirmed in peripheral leukocytes via immunofluorescence of γ-H2AX (FIG. 8B). Phosphorylation of histone 2AX, or γ-H2AX, occurs in response to double-stranded breaks, over a 2-Mbp region flanking the break site (22). ATM and other ATM-like kinases are responsible for this phosphorylation. Double-stranded breaks were generally more prevalent in lymphocytes than in other mononuclear cells types, and peaked after the second cycle and during the following remission period for all three genotypes. Atm$^{-/-}$ mice had significantly higher levels of double-stranded breaks during all three remission periods than wildtype mice (p<0.05), also seen with the comet assay. Lack of repair of double-stranded breaks was once again evident 2 and 4 weeks after the end of treatment in Atm$^{-/-}$ mice, possibly representing incomplete healing of the epithelial barrier, and prolonged effects of chronic inflammation. Heterozygous mice demonstrated similar patterns of γ-H2AX formation to wildtype mice throughout treatment and remission periods. A slight but non-significant increase in double-strand break formation, however, was seen over wildtype mice 2 weeks after the end of treatment.

Figure 9:
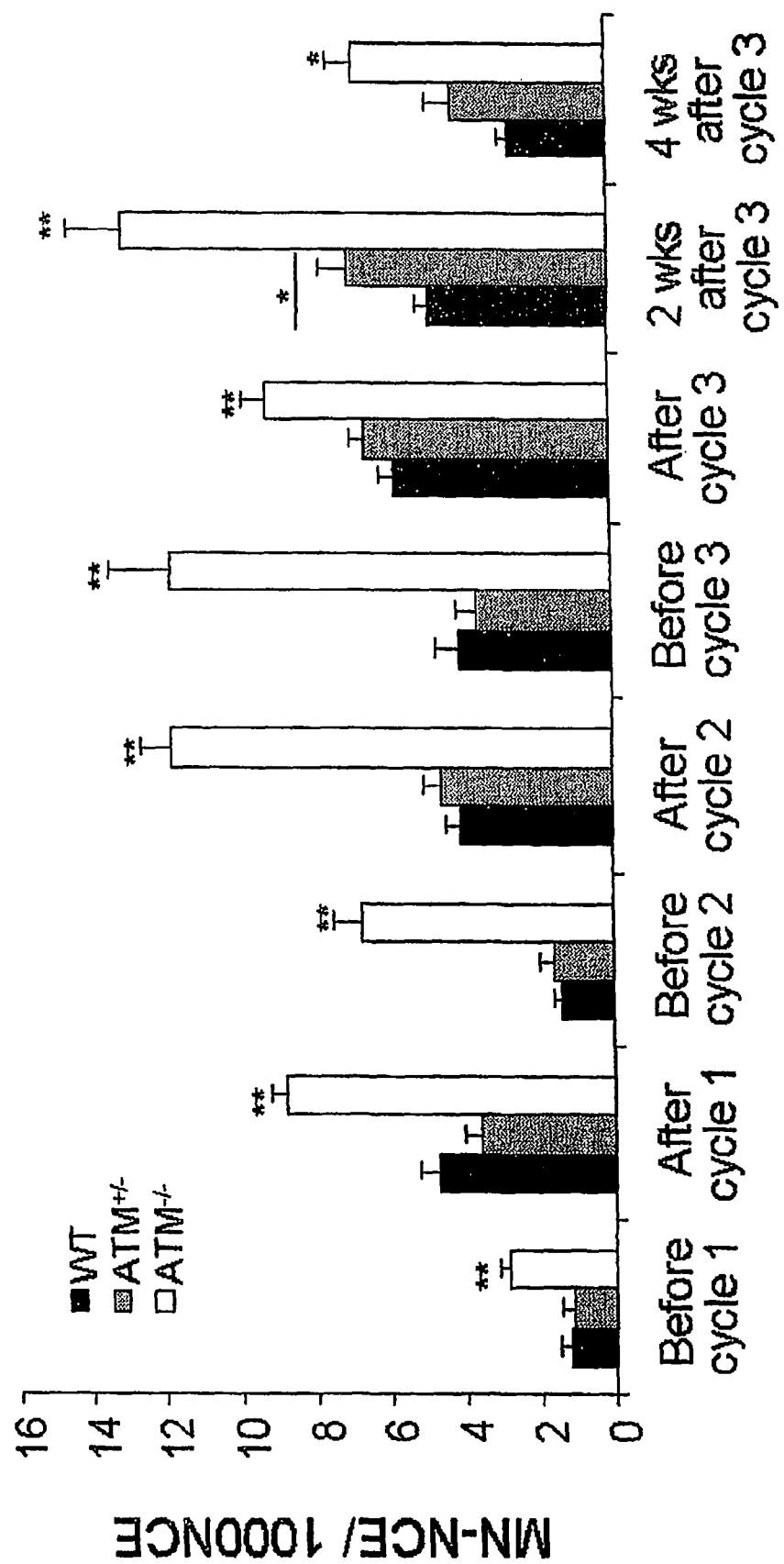
FIG. 9. Micronucleated normochromatic erythrocytes (MN-NCEs) per 1000 NCEs. ANOVA of a linear regression model for all three genotypes and treatment cycle effects were **: p<0.01, *: p<0.05 for Atm$^{-/-}$ versus Atm$^{+/-}$ and wildtype mice unless indicated otherwise.

Micronucleus formation in erythroblasts was measured as micronucleated mature erythrocytes in the peripheral blood. Toxicity of inflammation was evident as early as after the acute 7 day treatment of DSS, and more severely so in Atm$^{-/-}$ mice (FIG. 9). Micronucleus induction was significantly higher in Atm$^{-/-}$ mice at every point of blood collection throughout treatment, and up to 4 weeks afterwards compared to both wildtype and heterozygous mice. Similarly to γH2AX foci formation, heterozygous mice demonstrated higher levels of micronucleus formation only at 2 and 4 weeks after the end of treatment compared to wildtype mice, further indicating the importance of ATM during chronic inflammation. Increased sensitivity of Atm$^{-/-}$ mice to chromosomal aberrations in the bone marrow may be due to continual induction of damage to erythroblasts in the bone marrow, or a defect in clearance of micronucleated erythrocytes.

Increased 8-Oxoguanine Formation in Peripheral Blood and Colon Tissue.

Figure 10:
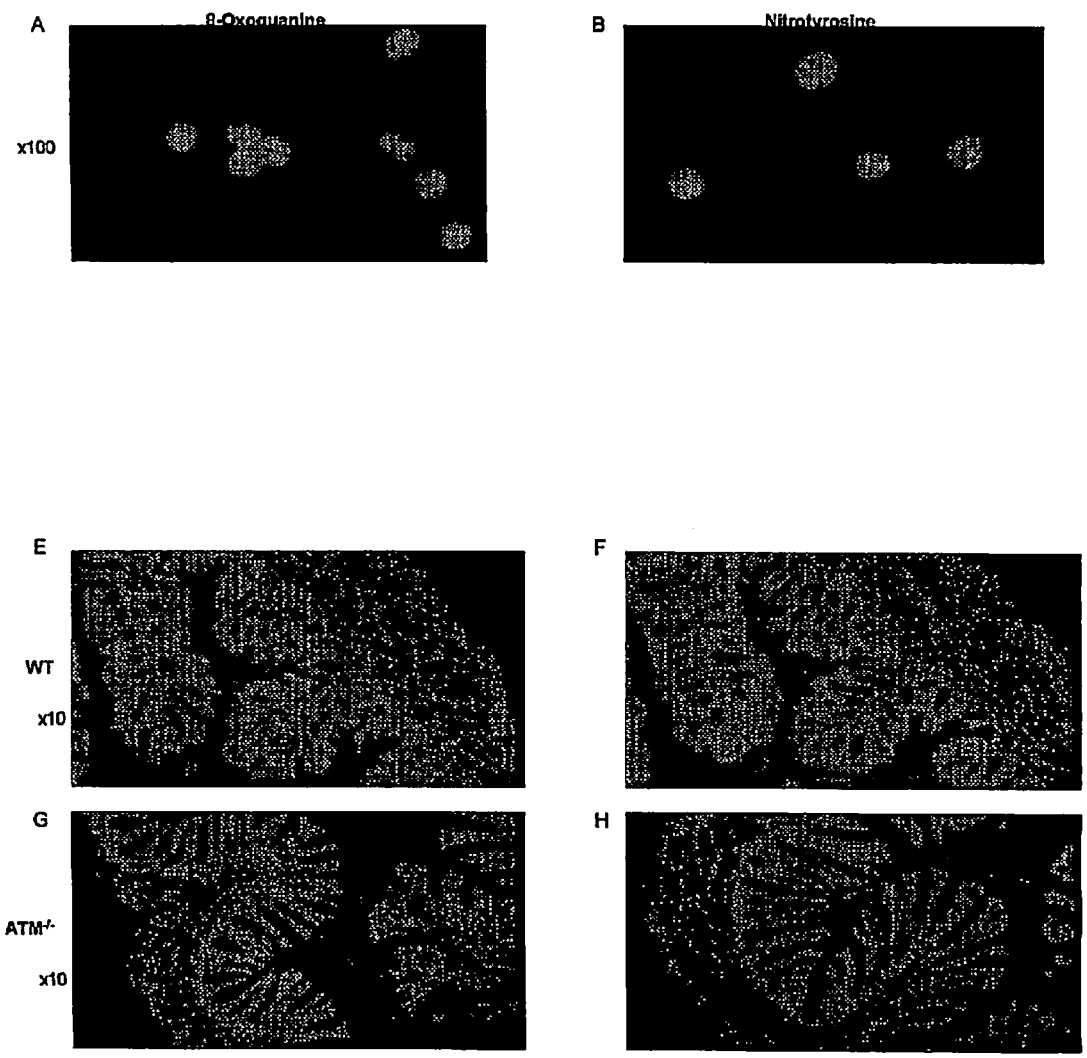
FIGS. 10A-10I. 8-oxoguanine and nitrotyrosine formation in peripheral leukocytes and the distal colon.

The presence of inflammation-derived reactive oxygen and nitrogen species potentially causative for the observed DNA strand breaks as well as micronucleus formation was measured in the form of 8-oxoguanine in DNA and nitrotyrosine in proteins of peripheral leukocytes and in the distal colon (FIG. 10). 8-oxoguanine is a DNA lesion caused by the reaction of oxidative reactive species such as hydroxyl radicals with DNA causing G:C to T:A transversions during replication (27), and nitrotyrosine is formed from NO-induced peroxynitrite reacting along with other reactive species to tyrosine residues of proteins (28). Wildtype mice alone demonstrated significant increases after an acute 7 day exposure to DSS in both 8-oxoguanine and nitrotyrosine formation in peripheral leukocytes (p<0.01). Atm$^{-/-}$ mice also demonstrated significant increases in 8-oxoguanine (p<0.05) and nitrotyrosine formation (p<0.05) after 7 days of DSS treatment, however, only 8-oxoguanine formation was significantly higher in Atm$^{-/-}$ compared to wildtype mice at the end of treatment (p<0.05). Both 8-oxoguanine and nitrotyrosine were also evident in surface epithelial cells proximal to and in the villous crypts closest to the intestinal lumen and in inflammatory cells of the distal colon (FIGS. 10E-10H). Staining for 8-oxoguanine localized in the nucleus while nitrotyrosine was evident in both the nucleus and cytoplasm of damaged cells. Staining for 8-oxoguanine was more prominent in the Atm$^{-/-}$ compared to wildtype mice (p<0.01), while nitrotyrosine levels were similar in both genotypes (FIG. 10I).

Persistent Immune Response in Atm$^{-/-}$ Mice.

As a possible explanation for the severe systemic genotoxicity displayed by Atm$^{-/-}$ mice, the immune response at each point of blood collection was characterized and compared to wildtype mice. Though the innate response primarily drives DSS-colitis and potentially the observed genotoxicity, we hypothesized the adaptive immune response would be also modulated and play a role in driving genotoxicity. Transcript levels of Th1, Th17/23, and Th2 cytokines in the peripheral blood, where genotoxicity was measured, were quantified via quantitative real-time PCR (FIG. 11). Atm$^{-/-}$ mice displayed greater upregulation of TNF-α (Tnf1) and MCP-1 (Ccl2) during the second remission period and after the third cycle of treatment (p<0.05) than wildtype mice, indicative of a chronically activated innate immune response. Levels of IL-6, IL-12, and IL-23 were also significantly upregulated in Atm$^{-/-}$ compared to wildtype mice after treatment cycles and during remission periods, indicative of T-cell mediated proinflammatory responses. Interestingly, IL-17 transcripts were not detected in both genotypes. Similarly, lower levels of IL-17, and increased levels of Th12/23 and Th1 cytokines have been previously observed in DSS treated C57BL/6 mice (29).

Although levels of IFN-γ (Ifng), also an indicator of a T-cell response, were modulated in Atm$^{-/-}$ mice, no significant differences were seen compared to wildtype mice. The Th2 response was more pronounced in Atm$^{-/-}$ mice in chronic phases of treatment, characterized by increased expression of IL-4 (Il4), IL-10 (Il10), and TGF-β (Tgfb). A defect in tolerance mechanisms associated with anti-inflammatory cytokines are therefore most likely not the cause of increased sensitivity of Atm$^{-/-}$ mice to chronic inflammation.

Figure 12C:
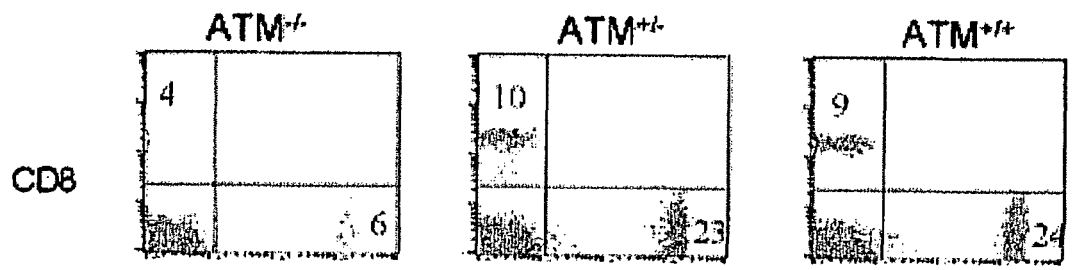
Figure 12D:
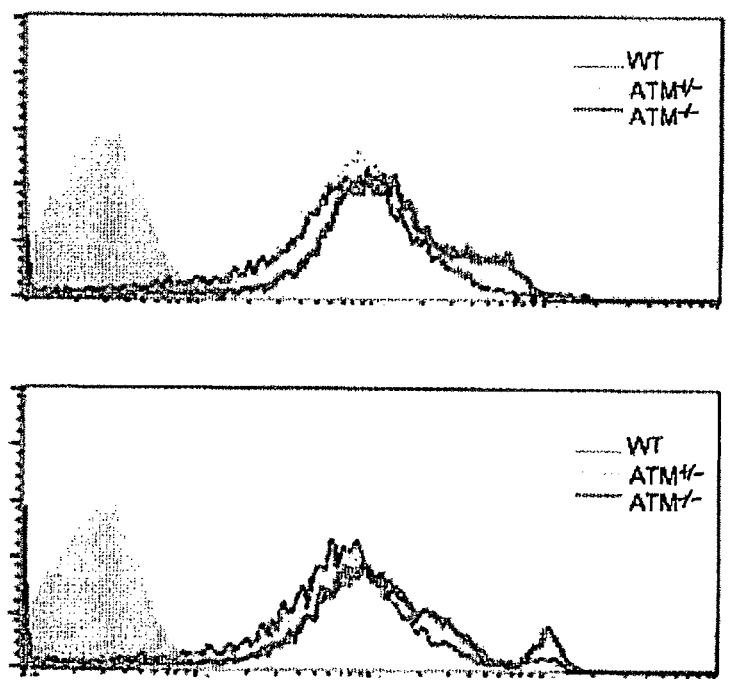

T-cell populations in the peripheral blood were also characterized by flow cytometry for CD4, CD8α, CD69, an early activation marker of all T-cells including NK-cells (30), and CD44, expressed on leukocytes and involved in recruitment, activation, and effector functions (31) (FIGS. 12A-D). Spontaneously, Atm$^{-/-}$ mice have significantly lower counts of mature CD4$^+$ T-cells than wildtype and heterozygous mice, in agreement with previous findings (FIG. 12C) (32-34). However, a significantly larger proportion of these T-cells are activated in response to DSS treatment compared to wildtype mice as shown by positive staining for CD69 and CD44 (FIGS. 12A and 12B). Heterozygous mice demonstrated similar levels of positive staining compared to wildtype mice (FIG. 12D). Numbers of CD4 and CD8α positive T-cells were also significantly modulated throughout treatment, most likely representing the dynamic influx and efflux of cells between the site of inflammation and the peripheral blood. Percent activated T-cells remained significantly elevated especially in remission periods in Atm$^{-/-}$ compared to wildtype mice until the end of the study, indicating a persistent immune response.

Discussion

Atm$^{-/-}$ mice have decreased numbers of circulating T-cells due to intrinsic defects in T-cell progenitors and consequential developmental abnormalities of single positive thymocytes (9, 32). However, though lower in number, mature T-cells from A-T patients have been shown to be functionally normal; demonstrating the capability of mounting a competent immune response (35). Atm$^{-/-}$ mice also do not develop spontaneous colitis or other inflammatory disorders of the gastrointestinal tract (36). However, when challenged with DSS causing a disruption in the integrity of the intestinal epithelial barrier, we demonstrated that Atm$^{-/-}$ mice exhibit greater severity of clinical symptoms and mortality rates, DNA damage to peripheral leukocytes and erythroblasts, and mount an even stronger immune response characterized by inflammatory cytokines and circulating activated T-cells compared to wildtype mice. A significant gene dosage effect was not seen in terms of disease activity or percent activated T-cells, though a small increase in genotoxicity over wildtype mice was seen after the third cycle; indicating potential compensatory mechanisms for heterozygosity of Atm. Similarly, Atm heterozygosity does not increase tumor susceptibility in mice after γ-irradiation compared to wildtype mice (37), though increased susceptibility to mammary tumorigenesis is seen in a Brca1 mutant background, compared to Atm sufficient mice (38).

The observed systemic DNA damage can be assumed to be inflammation mediated since DSS itself is not directly genotoxic (39, 40). Reactive species derived from inflammatory cells through oxidative burst may cause oxidative and nitrative damage both locally and systemically measured by 8-oxoguanine and nitrotyrosine formation. Localization of this damage to the villi, surrounding epithelial cells, and infiltrating inflammatory cells may be due to DSS-induced villous atrophy and extensive epithelial turnover. Though ATM does not manifest a protective role in terms of protein damage, 8-oxoguanine levels were found to be higher in Atm$^{-/-}$ mice, demonstrating lack of repair of oxidative DNA damage in addition to strand breaks. Interestingly, although DNA damage remained elevated, clinical symptoms of colitis were not present during remission periods and after the end of treatment, emphasizing the role of sub-clinical inflammation in the induction of DNA damage and the lack of repair of previously incurred damage. High levels of inflammation-associated oxidative stress, in addition to inherent deficiencies in repair of the resultant DNA damage, and partial suppression of DNA damage response-dependent apoptosis (41, 42) may explain the extreme sensitivity of the Atm$^{-/-}$ mice. An accumulation of DNA damage over the entire treatment period amidst slow DNA repair and cell turnover is therefore a probable explanation for increasing levels of DNA damage in Atm$^{-/-}$ mice, taking into account the relatively long lifespan of lymphocytes. Differentiation of naïve T cells into Th1 and Th17 effector cells could cause proliferation (43), in which accumulated DNA damage can lead to fixation of mutations.

Accumulation of double strand breaks can lead to chromosome breaks and micronuclei formation (44). Damage to erythroblasts in the bone marrow may be a humoral effect of inflammation-associated DNA damage, as with the peripheral leukocytes. Pro-inflammatory cytokines are preferentially released by cells that have migrated to the sites of inflammation rather than by resident macrophages (4). A recirculating pool of activated monocytes may recruit and activate effector cells, coming into contact with erythroblasts in the bone marrow, causing the observed clastogenicity.

The persistently activated immune response mounted by Atm$^{-/-}$ mice demonstrate a possible role of ATM in immunoregulation during DSS treatment. The recruitment of myeloid-derived cells to the site of inflammation, along with resident dendritic cells, allow for phagocytosis of DSS particles and activation of the adaptive response involving differentiation of naïve T-cells into activated effector cells (45). The prolonged presence of a larger percentage of activated T-cells in Atm$^{-/-}$ mice, which harbor much lower total counts of CD4$^+$ T cells, represents the capacity of these mice to mount a successful yet damaging immune response despite this deficiency. An increase in messenger levels of inflammatory cytokines especially during remission periods is in itself evidence for systemic distribution, which also corresponded to levels of activated T-cells and genotoxicity in the peripheral blood. This persistent activation of T-cells and upregulation of cytokines can result in increased activity of macrophages and oxidative bursts, which may be a potential explanation for the observed direct genotoxicity to peripheral leukocytes. Further mechanisms may be investigated by administration of enzymatic inhibitors or antiproliferative agents.

Recent evidence has pointed to the role of DNA damage response involving ATM in modulating an immune response. Genotoxic insult and activation of the ATM/ATR pathway was shown to upregulate ligands for the NKG2D receptor in mice and in humans, present on all NK cells, γδ-T cells, and activated CD8$^+$ T cells (46). This serves as a link between genotoxic stress and immune activation. Therefore, not only can the immune response potentially cause DNA damage via oxidative burst, but DNA damage itself can further activate NK-cells, potentially causing further damage if not properly repaired, as in Atm$^{-/-}$ mice. Nuclear ATM has also been shown to directly bind NF-κB essential modulator (NEMO), a modulator of NF-κB, leading to cytoplasmic translocation and activation of NF-κB, resulting in transcription of inflammatory and prosurvival response genes specifically in response to tolerable DNA damage (47). These varying modes of activation signify a coupling of stress response and cell survival.

The lack of ATM in these aspects could result in abnormal signaling in terms of response to genotoxic stress in the setting of chronic inflammation. Transcriptional repression of ATM has recently been found selectively in naïve T-cells of rheumatoid arthritis patients, in which there is increased DNA damage thought to be independent of inflammation; indicating alternative modes of increased DNA damage in cells deficient in ATM (48). Aside from ATM deficiency, FEN1 deficiency, a multifunctional endonuclease, leads to incomplete digestion of DNA in apoptotic cells and results in chronic inflammation and autoimmunity (49). Similarly, increased levels of DNA damage resultant from chronic inflammation, due to an inherent deficiency in double strand break repair in Atm$^{-/-}$ mice, may actually further promote inflammation and cause further DNA damage in a positive feedback loop. ATM may play therefore a protective role, not only as a DNA damage sensor, but also as an immunoregulator. The increased sensitivity to DSS treatment was not only present as clinical symptoms from localized inflammation in the colon, but manifested itself as a systemic insult characterized by genotoxicity and activation of immune responses.

In summary, Atm$^{-/-}$ mice are more sensitive to DSS-induced acute and chronic inflammation than heterozygous or wildtype mice, especially during remission and up to four weeks after the final round of treatment, demonstrating lack of repair of incurred damage. Increased sensitivity was characterized by higher incidence of mortality, clinical symptoms, systemic genotoxicity to peripheral leukocytes and erythroblasts, and an activated immune response including increased transcripts of inflammatory cytokines in the peripheral blood. Systemic genotoxic stress induced by byproducts of inflammation may be able to further promote inflammatory responses and pro-survival mechanisms, via the intricate involvement of ATM. The lack of this protein causes further DNA damage and genetic instability, along with a more potent immune response, possibly due to other pathways alerting and further activating the immune response, or by defects in resolution of activated effector cells. ATM therefore can be inferred to play a role in immunoregulation and maintenance of genetic stability during inflammation, and be considered as a potential target for not only chronic inflammatory diseases but also for cancer therapy and prevention.

REFERENCES CITED IN EXAMPLE 2

1. See Example 1.
2. Coussens L M, Werb Z. Inflammation and cancer. Nature 2002; 420: 860-7.
3. Eaden J A, et al. Gut 2001; 48: 526-35.
4. Sartor R B. et al. Nat Clin Pract Gastroenterol Hepatol 2006; 3: 390-407.
5. Bredemeyer A L, et al. Nature 2006; 442: 466-70.
6. Callén E, et al. Cell 2007; 130: 63-75.
7. Lavin M F, Shiloh Y. Annu Rev Immunol 1997; 15: 177-202.
8. Lavin M F. Nat Rev Mol Cell Biol 2008; 9: 759-69.
9. Bagley J, et al. Blood 2004; 104: 572-8.
10. Lumsden J M, et al. J Exp Med 2004; 200: 1111-21.
11. Meira L B, et al. J Clin Invest 2008; 118: 2516-25.
12. Hofseth L J, et al. Proc Natl Acad Sci 2003; 100: 143-8.
13. Okayasu I, et al. Gastroenterology 1990; 98: 694-702.
14. Dieleman L A, et al. Gastroenterology 1994; 107: 1643-52.
15. Tardieu D, et al. Cancer Lett 1998; 134: 1-5.
16. Liao J, et al. Mol Carcinog 2008; 47: 638-46.
17. Kohonen-Corish M R J, et al. Cancer Res 2002; 62: 2092-7.
18. Reliene R, et al. DNA Repair 2006; 5: 852-9.
19. Murthy S N, et al. Dig Dis Sci 1993; 38: 1722-34.
20. Olive P L, et al. Nat Protocols 2006; 1: 23-9.
21. Goldstine J V, et al. DNA Repair 2006; 5: 432-43.
22. Muslimovic A, et al. Nat Protocols 2008; 3: 1187-93.
23. Abramoff M, et al. J Biophotonics Int 2004; 11: 36-42.
24. Lossos I S, et al. Leukemia; 17: 789-95.
25. R Development Core Team. R: a language and environment for statistical computing. Vienna (Austria): R Foundation for Statistical Computing; 2007. ISBN 3-900051-07-0.
26. Barzilai A, et al. DNA Repair 2002; 1: 3-25.
27. Pinlaor S, et al. Carcinogenesis 2004; 25: 1535-42.
28. Liu J S, et al. Am J Pathol 2001; 158: 2057-66.
29. Melgar S, et al. Am J Physiol Gastrointest Liver Physiol 2005; 288:G1328-38.
30. Testi R, et al. Immunol Today 1994; 15: 479-83.
31. Puré E, Cuff C A. Trends Mol Med 2001; 7:213-21.
32. Vacchio M, et al. Proc Natl Acad Sci 2007; 104: 6323-8.
33. Paganelli R, et al. J Clin Immunol 1992; 12: 84-91.
34. Xu Y, et al. Genes Dev 1996; 10: 2411-22.
35. Giovannetti A, et al. Blood 2002; 100: 4082-9.
36. Barlow C, et al. Cell 1996; 86: 159-71.
37. Mao J H, et al. Oncogene 2008; 27:6596-600.
38. Bowen T J, et al. Cancer Res 2005; 65:8736-46.
39. Mori H, et al. Nutr Cancer 1984; 6: 92-7.
40. Nagoya T, et al. Pharmacometrics 1981; 22: 621-7.
41. Pusapati R, et al. Proc Natl Acad Sci 2006; 103: 1446-51.
42. Westphal C, et al. Nat Genetics 1997; 16: 397-401.
43. Sprent J, Tough D F. Science 1994; 265: 1395-400.
44. Obe G, et al. Mutat Res 2002; 504: 17-36.
45. Dieleman L A, et al. Clin Exp Immunol 1998; 114: 385-91.
46. Gasser S, et al. Nature 2005; 436: 1186-90.
47. Wu Z H, et al. Science 2006; 311: 1141-6.
48. Shao L, et al. J Exp Med 2009; 206: 1435-49.
49. Zheng L, et al. Nat Med 2007; 13: 812-9.

Example 3: Additional Data on Characterization of Systemic Genotoxicity and the Potential Mechanisms Involved In an effort to further characterize susceptible cell types to DNA damage, subpopulations of leukocytes in the peripheral blood as well as cells from distant lymphoid and non-lymphoid tissues were analyzed for DNA single- and double-stranded breaks. We also hypothesized that mediators of inflammation such as tumor necrosis factor-alpha (TNF-α) would be sufficient and necessary to induce the observed systemic genotoxicity in mice without preexisting inflammation. DNA damage was found in both lymphoid and non-lymphoid cell types, manifesting more damage to CD4 and CD8 T-cells versus other cell types. TNF-α was sufficient to induce systemic genotoxicity in wildtype mice. Examination of transcript levels as well as protein expression levels of the DNA double strand break recognition and repair protein ataxia telangiectasia mutated (ATM) in CD4 and CD8 T-cells revealed no differences in the IL-10$^{-/-}$ compared to wildtype mice.

Methods

Animals.

Gαi2$^{-/-}$ (B6/129Sv background, 3 months) (2) IL-10$^{-/-}$ (C3H/HeJBir background, 3 or 6 months) mice were housed in the UCLA Department of Laboratory and Animal Medicine under specific pathogen free conditions, autoclaved bedding and food, with standard rodent chow diet, acidified drinking water, and 12:12 light:dark cycle. All mice were bred at UCLA except IL-10$^{-/-}$ and C3H/HeJ which were purchased from Jackson Laboratory (Bar Harbor, Me.).

Blood/Tissue Collection.

Peripheral blood was collected via the facial/mandibular vein with a 5 mm lancet (Braintree Scientific, Braintree, Mass.) into EDTA coated collection tubes (Braintree Scientific). For magnetic bead separations, a terminal bleed utilizing 500 μL was used. For the comet assay, blood was immediately diluted 1:1 in RPMI/10% DMSO and immediately frozen at −80° C. until further analysis. Freshly collected blood was immediately processed for all other assays. Spleens, peripheral lymph nodes (PLN) including both axillary and inguinal lymph nodes (at least 5/mouse) and mesenteric lymph nodes (MLN) (at least 5/mouse) were harvested and processed into single cell suspensions in RPMI/10% FBS for further analysis. Isolation of intestinal epithelial/intraepithelial cells was done as described previously (3).

Assessment of DNA Damage

Alkaline Comet Assay.

To detect DNA strand breaks, as well as alkali labile sites in DNA, the alkaline comet assay was performed as described elsewhere (4). Frozen blood or single cell suspensions were thawed on ice and further diluted 1:15 in PBS before further sample preparation. After lysis and electrophoresis, gels were stained with SYBR Gold (Molecular Probes) and visualized under a fluorescent microscope (Olympus Ax70, Tokyo, Japan) at 10× magnification. Comet images were captured and analyzed with the CASP image analysis program (http://casp.sourceforge.net). The olive tail moment, which represents both tail length and fraction of DNA in the tail, was used for data collection and analysis, in which apoptotic cells were excluded under previously proposed criteria (4).

Determination of Oxidative DNA Damage.

For determination of oxidative DNA damage the enzyme hOgg1-modified comet assay was used (5). After lysis in the alkaline comet assay, samples were washed in an enzyme wash buffer (40 mM HEPES, 0.1M KCl, 0.5 mM EDTA, 0.2 mg/ml BSA, pH 8.0) then incubated at 37° C. for 10 min in either control (buffer with no hOGG1) or enzyme treated (buffer with hOGG1) solutions according to the manufacturer's recommendations (New England Biolabs, Ipswich, Mass.). Both control and enzyme treated gels were then placed in electrophoresis buffer and processed identically to the alkaline comet assay.

Immunofluorescence.

Peripheral blood and splenocytes were incubated in Buffer EL (Qiagen, Valencia, Calif.) on ice to remove erythrocytes. Other single cell suspensions did not require erythrocyte lysis. Samples were then processed on coverslips as described elsewhere (6). Briefly, after permeabilization and blocking, cells were incubated with mouse anti-phospho-Histone H2A.X S139(P) (Upstate, Temecula, Calif.) at 1:400 followed by FITC-conjugated anti-mouse IgG (Jackson ImmunoResearch, West Grove, Pa.) at 1:200. Coverslips were mounted with VECTASHIELD with 4,6-diamidino-2-phenylindole (Vector Laboratories, Burlingame, Calif.). Images were captured with FISH analysis software (Cyto-Vision, Applied Imaging Corporation, San Jose, Calif.) connected to a Zeiss automated FISH microscope. At least 125 cells were counted and cells with more than four distinct foci in the nucleus were considered positive (6). Apoptotic cells are easily distinguishable due to presence of 10-fold higher number of nuclear foci than highly damaged cells (7), and were not included in analyses.

In Vivo Micronucleus Assay.

Micronucleus formation was determined in normochromatic erythrocytes as micronucleated normochromatic erythrocytes per 1000 normochromatic erythrocytes as described previously (1, 8).

Magnetic Bead Isolation of Cells.

Individual subpopulations of cells in the peripheral blood were isolated by magnetic bead isolation. Leukocytes were separated from whole blood by density centrifugation with Histopaque-1119 (Sigma) according to manufacturer's instructions. Cells were then labeled with MicroBeads conjugated to monoclonal mouse antibodies (anti-CD4, anti-CD8, anti-CD19, anti-CD11c, or anti-CD3) and magnetically separated by positive selection on MS columns (Miltenyi Biotec, Bergisch Gladbach, Germany).

Injection of Cytokines.

Mouse TNF-α (Sigma) and/or mouse IL-1β (Sigma) were injected via the tail vein at 500 ng/mouse and 100 ng/mouse, respectively, dissolved in saline. Control animals received vehicle only. Peripheral blood was collected at 1 hr, 2 hrs, 4 hrs, and 24 hrs after injection for genotoxicity assays.

Gene and Protein Expression.

Gene expression was measured as mRNA transcript levels of ataxia telangiectasia mutated (ATM) and xeroderma pigmentosum group C(XPC) standardized to TATA box binding protein (TBP), the internal control gene in peripheral leukocytes by quantitative real time PCR as previously described (Westbrook et al) utilizing Taqman Gene Expression kits for ATM and TBP (ABI). Protein expression was measured as mean fluorescence intensity of anti-ATM protein kinase (pSer1981) by flow cytometry. Briefly, cells were stained for cell surface markers (PE-anti-CD4 or PerCP anti-CD8), and then processed for intracellular staining. Cells were fixed with 1.5% paraformaldehyde for 10 min at room temperature, permeabilized, and then stained with FITC-anti-pATM (Rockland Immunochecmicals, Inc) or the appropriate isotype control.

Statistical Analyses.

Results are expressed as mean±standard error of the mean. Statistical significance was determined by nonparametric one-way/two-way ANOVAs with Dunn's multiple comparison post test or paired Student's t-tests, defined as $p<0.05$. Calculations were performed with the statistical analysis software Graph Pad Instat version 3.00 (Graph Pad Software, San Diego, Calif.) or R: A language and environment for statistical computing. (R Development Core Team (2007). R foundation for Statistical Computing, Vienna, Austria. ISBN 3-900051-07-0, URL http://www.R-project.org).

Results

Differences in Susceptibility to DNA Damage in Peripheral Blood Subpopulations.

Figure 13B:
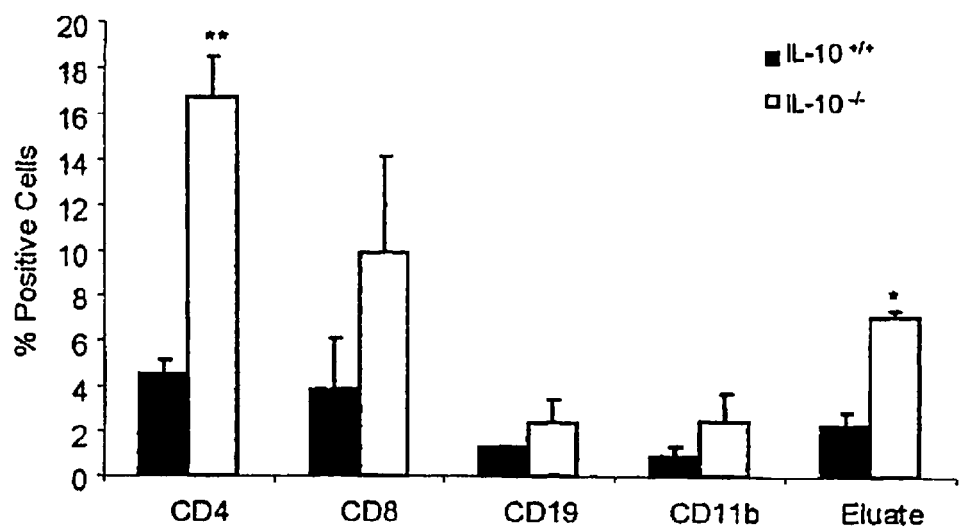

In order to determine leukocytes that may be more or less sensitive to inflammation-associated genotoxicity, subpopulations in the peripheral blood were isolated via magnetic bead separation and analyzed for DNA damage in Gαi2$^{−/−}$ and IL-10$^{−/−}$ mice. CD4$^+$ T-cells from IL-10$^{−/−}$ mice had significantly more DNA strand breaks as measured by the mean olive tail moment in the comet assay and as percent positive cells for γ-H2AX foci compared to wildtype littermates and to other cell types including CD19$^+$ B-cells and CD11b$^+$ macrophages (FIGS. 13A and 13B). The eluate, which contained cell types not positively selected for by magnetic beads, from IL-10$^{−/−}$ mice seemed to contain significantly higher percent positive cells for γ-H2AX foci compared to wildtype mice.

Figure 13D:
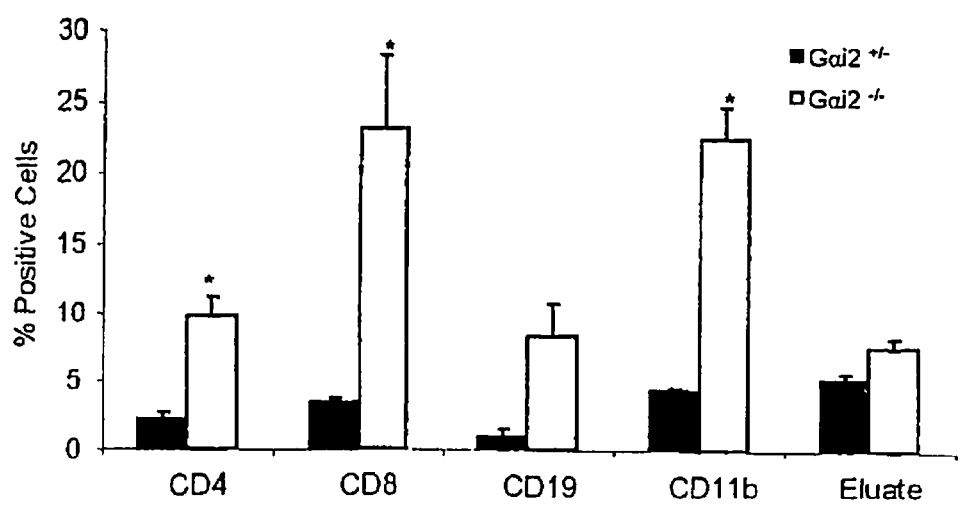

In Gαi2$^{−/−}$ mice, whose disease progression is faster and more severe than in IL-10$^{−/−}$ mice, DNA strand breaks were observed more frequently in multiple cell types including CD4$^+$ and CD8$^+$ T-cells, as well as in CD11b$^+$ macrophages compared to heterozygous littermates which do not develop colitis and to CD19$^+$ B-cells and cells in the eluate (FIGS. 13C and 13D). Results from the alkaline comet assay and γ-H2AX immunostaining correlated with each other, demonstrating a wider array of cell types damaged in the peripheral blood compared to the IL-10$^{-/-}$ mice. Clinical severity of inflammation therefore may correlate to a wider array of cell types affected.

Genotoxicity in Lymphoid Organs

Figure 14:
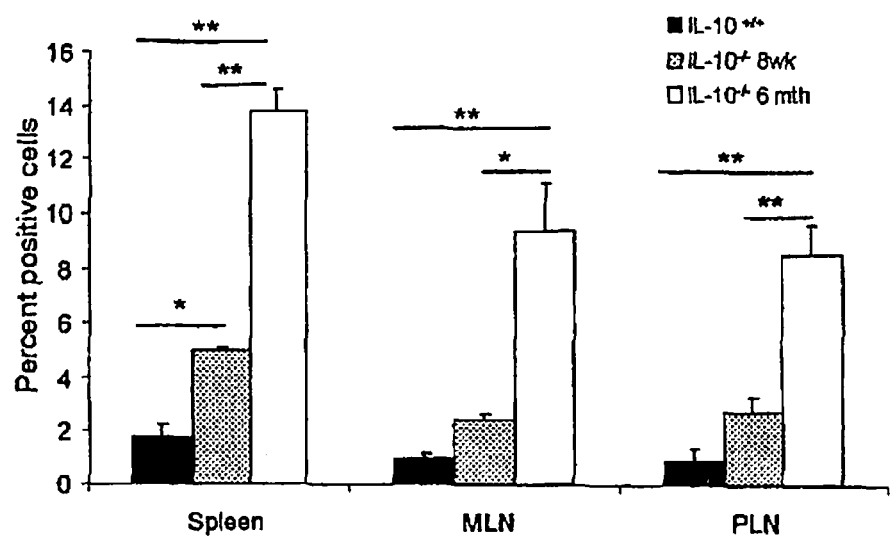
FIGS. 14A-14C. DNA damage to peripheral lymphoid organs, as determined by γH2AX immunostaining, alkaline comet assay without hOgg1 incubation, and alkaline comet assay with hOgg1 incubation, respectively, in IL-10$^{-/-}$ mice at 8 weeks of age and 6 months of age versus wildtype mice. *: p<0.05, **: p<0.01 by two way ANOVA with Dunn's multiple comparison test. Error bars represent SEM.
Figure 14B:
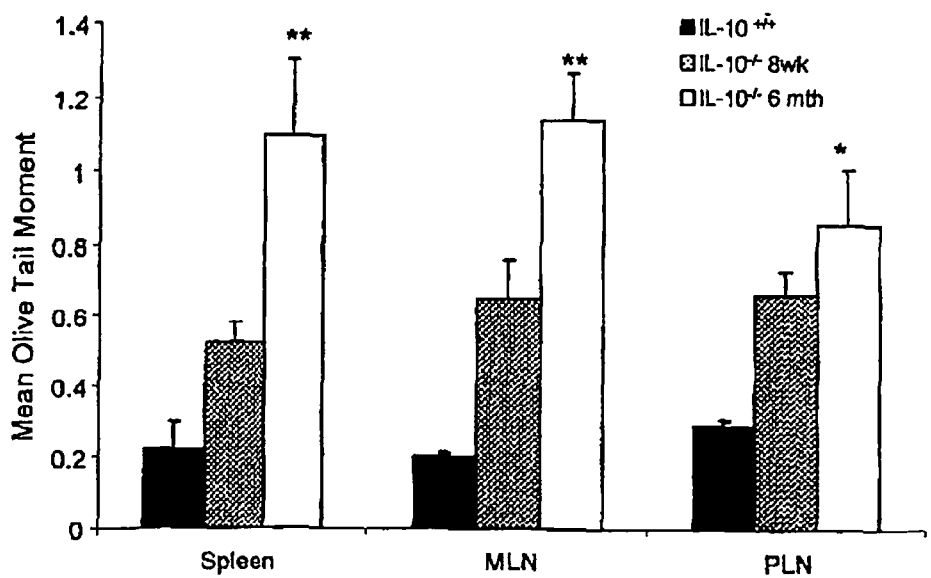
Figure 14C:
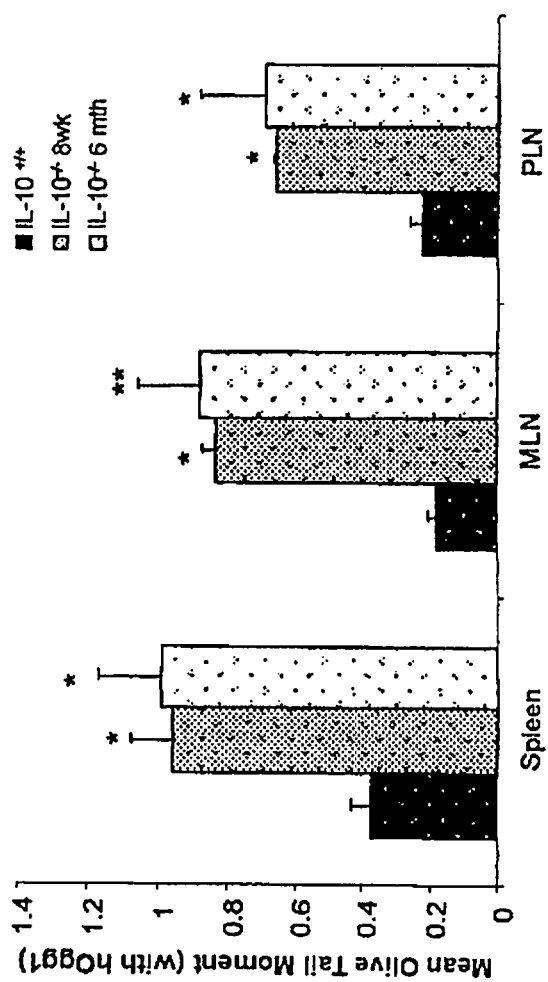

Lymphoid organs such as the spleen, mesenteric lymph nodes, and peripheral lymph nodes were isolated into single cell suspensions from IL-10$^{-/-}$ and wildtype mice, and analyzed for DNA damage. Surprisingly, all lymphoid tissues demonstrated significant genotoxicity compared to wildtype mice, characterized by DNA single- and double-stranded breaks, comparable to that seen in the peripheral leukocytes (FIGS. 14A-14C). Mesenteric lymph nodes, though physically in closest contact with the site of inflammation in the colon, demonstrated similar levels of DNA damage found in the peripheral lymph nodes, collected at distant sites relative to the site of inflammation. The spleen also showed similar levels of strand breaks, indicating systemic circulation of the components and cell types in the immune response involved in potentially causing the observed genotoxicity.

Previously, we have demonstrated DNA damage to correlate to disease activity in the peripheral blood of IL-10$^{-/-}$ mice (1). Similarly, utilizing younger IL-10$^{-/-}$ mice of 8 weeks of age with subclinical inflammation demonstrating lower clinical disease activity indices than those at 6 months of age, DNA damage in all the lymphoid organs was found to be lower compared to the older mice (FIGS. 14A-14C). Levels of oxidative base damage, measured by the alkaline comet assay with hOgg1 incubation, however were similar in the 8 week old mice compared to the 6 month old mice (FIG. 14C). Therefore, systemic DNA damage in the form of strand breaks correlates to disease activity in both the peripheral blood as previously demonstrated and the lymphoid organs of these mice.

Large and Small Intestinal Epithelial Cell Genotoxicity

Figure 15:
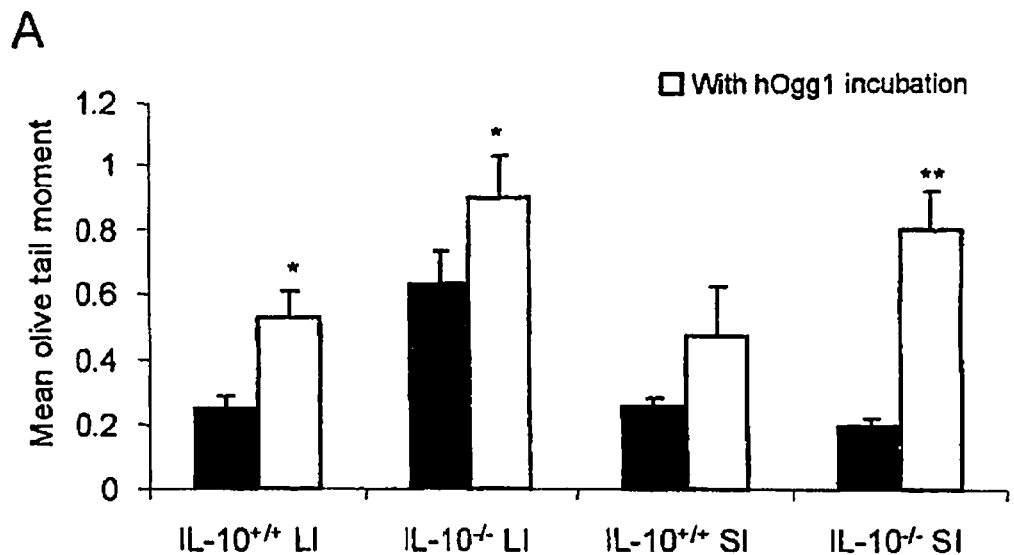
FIGS. 15A-15B. Genotoxicity to intestinal epithelial cells. DNA damage by alkaline comet assay with and without hOgg1 incubation and by γH2AX immunostaining, respectively, in IEC's from small and large intestine of IL-10$^{-/-}$ versus wildtype mice. *: p<0.05, **: p<0.01 by one way ANOVA with Dunn's multiple comparison test. Error bars represent SEM.
Figure 15B:
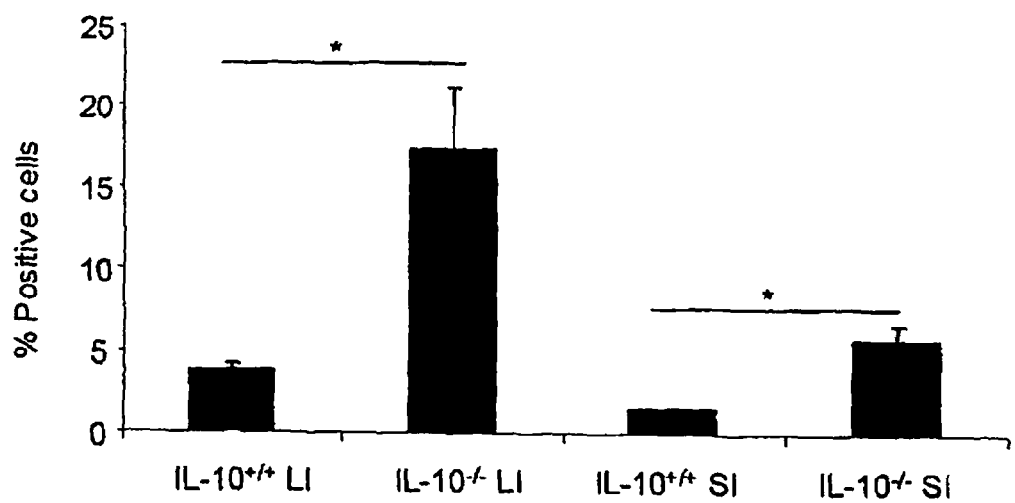
Figure 19B:
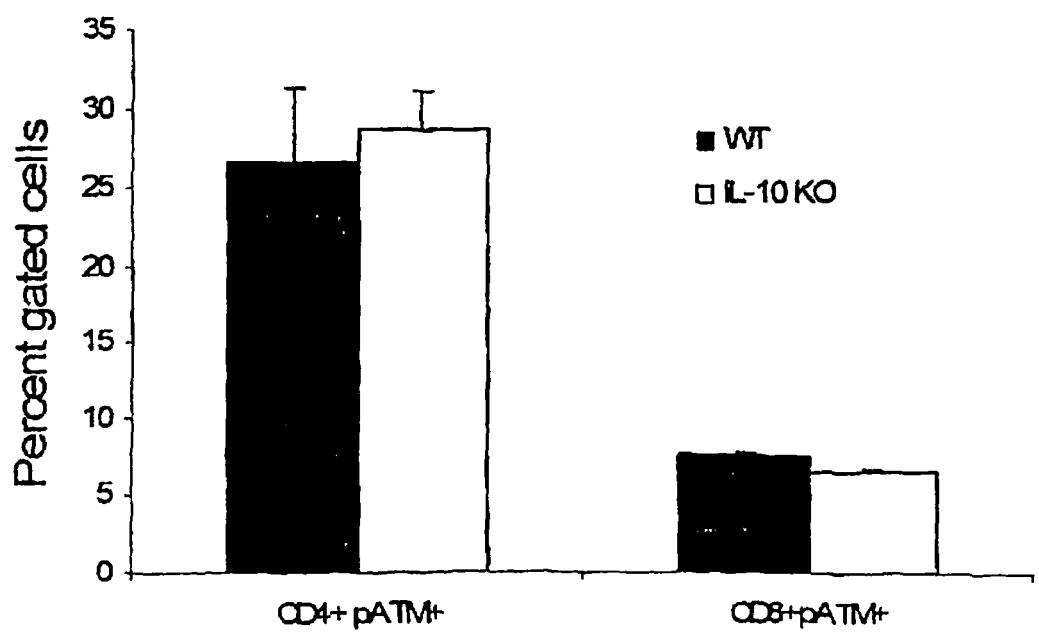

In addition to peripheral leukocytes and lymphoid organs, intestinal epithelial cells and intraepithelial cells were isolated from the large and small intestine of IL-10$^{-/-}$ (6 months of age) and wildtype mice. As expected from the sites of inflammatory activity, epithelial cells from the large intestine harbored greater genotoxicity than those from the small intestine, and IL-10$^{-/-}$ mice demonstrated greater genotoxicity to intestinal epithelial cells of both the small intestine and large intestine than wildtype mice (FIGS. 15A and 15B). Genotoxicity was characterized by presence of DNA single- and double-stranded breaks with oxidative base damage.

TNF-α is Sufficient to Induce DNA Damage

Figure 16B:
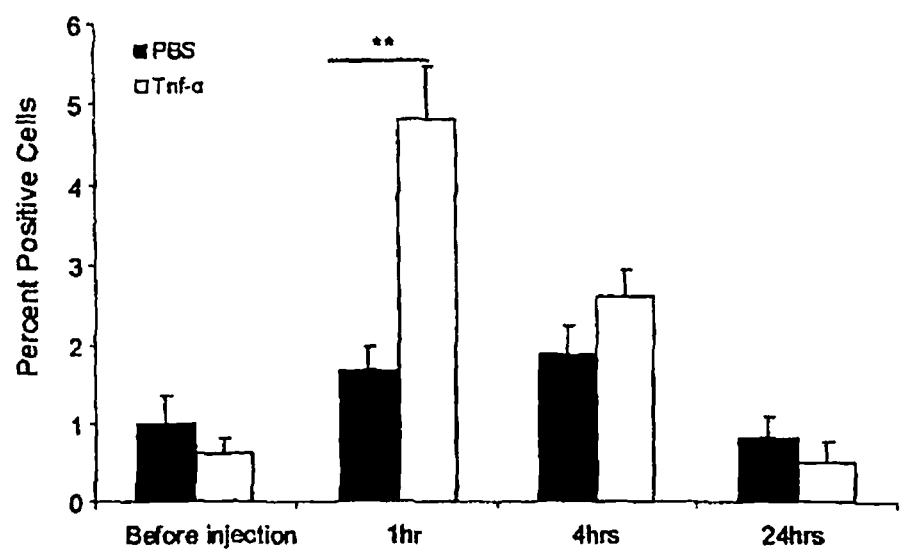

In order to determine sufficiency of a cytokine in inducing DNA damage, recombinant mouse TNF-α or saline was injected into the tail vein of wildtype mice (6-8 weeks of age) without any basal inflammatory activity. As soon as 1 hour post-injection, DNA damage to peripheral leukocytes was observed only in treated mice, which continued to remain elevated until approximately 4 hours post-injection, and then appeared to be repaired within 24 hours post-injection (FIGS. 16A and 16B). Damage was observed in both the alkaline comet assay and by formation of γ-H2AX foci. Micronuclei formation to erythroblasts measured in circulating normochromatic erythrocytes and indicative of clastogenicity, was minimally yet significantly elevated 48 hours post-injection compared to before injection (FIG. 16C).

In addition to the peripheral leukocytes, similar profiles of DNA damage were observed in the lymphoid organs such as in the spleen, mesenteric and peripheral lymph nodes 1.5 hours post-injection of the identical dose of recombinant TNF-α (FIGS. 17A-D). DNA strand breaks were once again most evident in CD4 and CD8 T-cells versus other cell types in the peripheral blood, as well as in the spleen and the peripheral lymph nodes. DNA damage was evident in the form of both single and double strand breaks accompanied by oxidative base damage as demonstrated by the mean olive tail moments and percent positive cells for γ-H2AX foci.

Figure 18B:
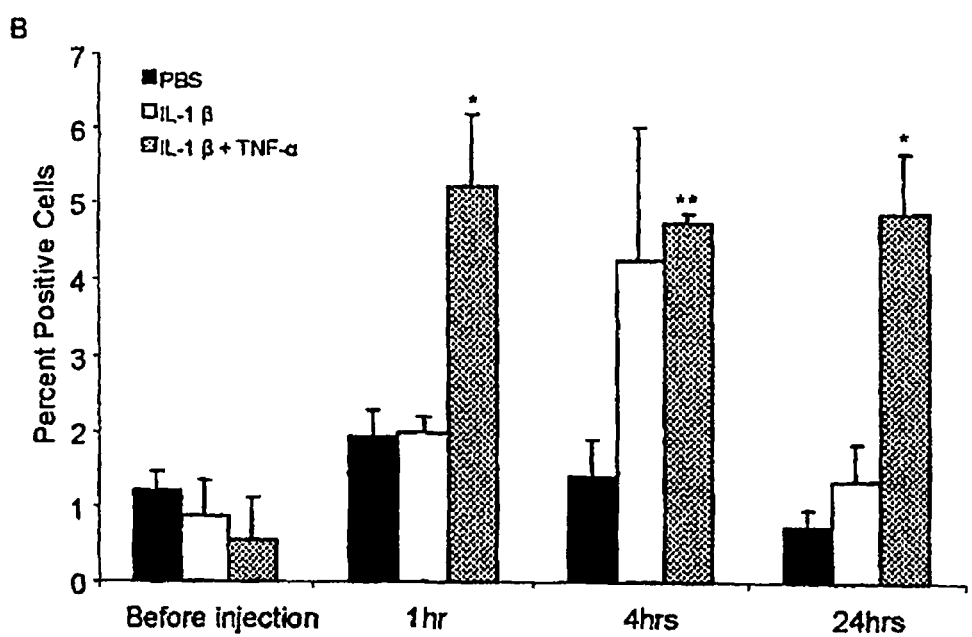

To determine whether or not a combinatorial administration of cytokines would yield a different genotoxicity profile than with TNF-α alone to peripheral leukocytes, recombinant mouse IL-β was injected via the tail vein at 100 ng per mouse alone or in combination with 500 ng of recombinant mouse TNF-α. Administration of IL-β alone resulted in maximum DNA damage to peripheral leukocytes occurring at 4 hours post-injection (versus 1 hour post-injection for TNF-α alone), followed by complete repair of damage by 24 hours post-injection (FIGS. 18A-C). However, when both cytokines were administered together, strand breaks and oxidative base damage measured by the alkaline comet assay increased dramatically at 4 hours post-injection and remained elevated even after 24 hours post-injection (FIG. 18A). DNA double strand breaks, specifically measured by γ-H2AX foci formation, however increased as soon as 1 hour post-injection, and then remained at the same levels until 24 hours post-injection indicating lack of DNA repair (FIG. 18B). Micronuclei formation was also elevated at 48 hours post-injection (FIG. 18C), indicating clastogenicity.

Figure 19:
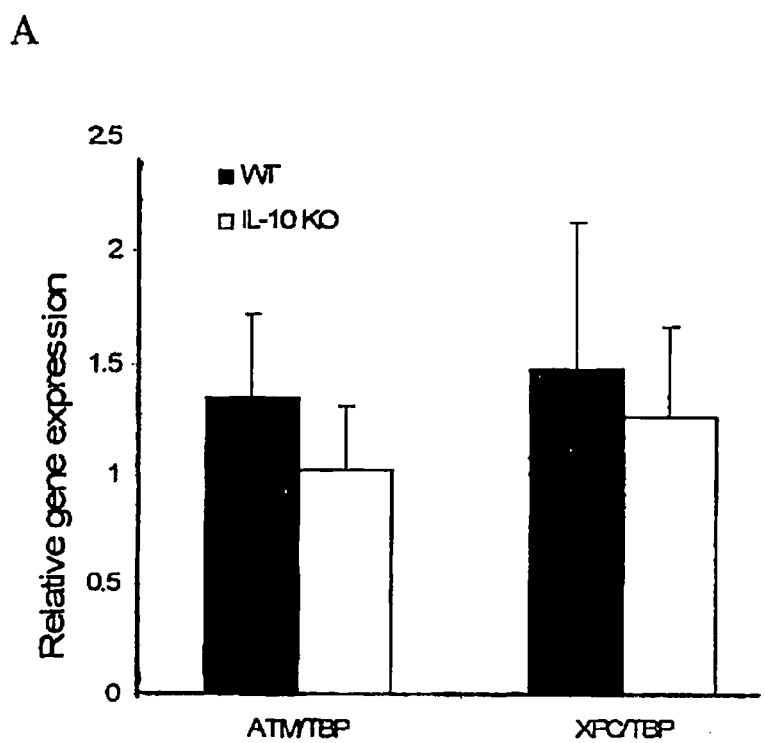
FIGS. 19A-19B. DNA repair capability in IL-10$^{-/-}$ mice.

Increased Genotoxicity in IL-10−/− Mice is not Due to Decreased Expression of ATM A recent study demonstrated that CD4 T-cells from rheumatoid arthritis patients selectively were deficient in transcript and protein levels of ATM, causing increased DNA strand breaks and rendering T-cells sensitive to apoptosis and premature immunosenescence (9). Levels of expression in terms of transcript levels and protein levels of ATM were therefore analyzed in order to see whether or not similar decreased DNA repair capabilities were a potential explanation for sustained systemic genotoxicity in the peripheral leukocytes of IL-10 mice with colitis. Transcript levels of ATM were almost identical in wildtype mice and IL-10 KO mice, as well as protein expression of activated pATM measured by flow cytometry (FIG. 19).

Discussion

Further characterization of intestinal inflammation-associated systemic genotoxicity as well as the determination of underlying mechanisms will give insight into the progression of associated diseases arising outside the intestinal tract such as lymphomas, effects on lymphocyte mediated immune responses, as well as illuminate potential areas of therapeutic utility. In addition to that of intestinal inflammation, mechanistic insights will carry much broader implications as patients with various other inflammatory diseases have recently been found to carry DNA damage to peripheral leukocytes or to specific subpopulations thereof. These include type 1 and 2 diabetes (10), rheumatoid arthritis (9), systemic lupus erythromatosus (11), liver cirrhosis (12), and pre-neoplastic conditions such as myelodysplastic syndrome (13).

DNA damage to CD4 and CD8 T-cells predominantly versus other cell types in the peripheral blood in IL-10$^{-/-}$ mice demonstrates that inflammation-induced DNA damage is not completely random, given that T-cells only represent 30-40% of total circulating leukocytes. In the more severe Gαi2$^{-/-}$ model, though the DNA of CD4 and CD8 T-cells may have been damaged first due their relative sensitivity, other cell types including the macrophages and to a lesser extent, B-cells were also damaged. This may indicate a correlation between severity of pathology and the inflammatory response with DNA damage to multiple cell types. In accordance with our data, others have also found relatively more damage to T-cells versus other cell types in the blood, such as in rheumatoid arthritis patients (9), and both basally and after treatment with hydrogen peroxide in isolated peripheral blood (14). Further basal differences have also been observed between naïve and memory T-cells in which the latter has been found to have greater DNA damage and thus a shorter lifespan than the naïve T-cells, which have a half life of 150-160 days (15). Longer lifespan, however could also lead to accumulation of DNA damage over time, despite having intact DNA repair capabilities, such as when comparing generally long-lived T-cells to short-lived B-cells, which depends on many factors including antigenic stimulation (14). The sensitivity of the CD4 and CD8 T-cell populations during inflammation may indicate excessive cellular stress, in which repair and cellular defense mechanisms cannot keep up with the oxidative environment of an inflammatory response. This can be supported by the fact that activated T-cells or T-cells infected with human immunodeficiency virus (HIV) contain elevated levels of mitochondrial superoxide and thus carry a reduction in the mitochondrial membrane potential (16). Other cell types, such as macrophages are selectively known to have defense mechanisms such as the constitutive expression of heme-oxygenase 1 (HO-1) to act as an "anti-inflammatory" agent which is further upregulated during acute inflammation by production of carbon monoxide and bilirubin (17), as well as a large number of strong antioxidant enzymes including superoxide dismutases, catalases, and glutathione peroxidases. Therefore, differing ROS scavenging and levels of antioxidant response enzymes, DNA repair capabilities, life span, and cellular permeability may explain the differences observed in sensitivity of cell types and in the context of the clinical severity of disease.

Genotoxicity to the lymphoid organs including the mesenteric lymph nodes, peripheral lymph nodes, and spleen, as well as to the intestinal epithelial cells in the IL-10$^{-/-}$ mice indicate both local as well as systemic damage that either may be indicative of circulating damaged leukocytes into and out of the peripheral lymphoid organs, or leukocytes that are damaged at these distant sites due to a systemic inflammatory response. Importantly, IL-10$^{-/-}$ mice demonstrate a correlation of DNA damage to severity of disease activity (which progresses with age) in the peripheral lymphoid organs. This disease activity correlation has previously been demonstrated in the peripheral leukocytes of chemically-induced colitis as well as in the IL-10$^{-/-}$ mice (1).

It is important to note that many models of intestinal inflammation including Gαi2$^{-/-}$, IL-10$^{-/-}$, and DSS-treated mice display systemic inflammation characterized by presence of activated T-cells and increased cytokine production such as TNF-α and IFN-γ, in not only the colon and lamina propria, but also in splenocytes and peripheral lymph nodes (18-20). Systemic inflammatory activation and immune hyper-responsiveness in these models observed in distant immune cells may therefore serve as a mechanism for the observed systemic genotoxicity.

We have found that a single injection of recombinant mouse TNF-α is sufficient to induce genotoxicity to peripheral leukocytes in healthy wildtype mice. Treatment for Crohn's disease as well as ulcerative colitis currently involves TNF-α blockers such as Remicade®, indicating the direct role of TNF-α in pathogenesis. It still remains to be explored whether or not the ligand binding to the TNF receptors itself, or downstream pathways involved in inflammatory activation of immune cells are responsible for the observed DNA damage. Interestingly, similar to what was seen in the models of chronic intestinal inflammation, CD4 and CD8 T-cells proved to be more sensitive than other cell types in the peripheral blood, and the peripheral lymphoid organs also manifested genotoxicity, albeit less than observed in the genetic models of colitis. High bioavailability of TNF-α in the peripheral lymphoid tissues may contribute to the observed DNA damage to these sites, since only a single bolus dose was administered. When combined with injection of IL-1β, another prominent cytokine found to be elevated in multiple models of chronic intestinal inflammation, DNA damage persisted for up to 24 hours without repair, indicating synergistic or delayed effects in the induction of genotoxicity. Circulating cytokines such as TNF-α and IL-1β in chronic intestinal inflammation therefore play a role in inducing systemic genotoxicity even without basal inflammatory activity. Further DNA damage, when persistent, may lead to genetic alterations which would be sufficient to create an inflammatory microenvironment, even if no previous inflammatory state is observed (21). The persistently elevated levels of large networks of cytokines/chemokines as well as their interactions, which better represent actual active intestinal inflammation, may therefore explain the chronically elevated levels of DNA damage observed systemically in multiple cell types.

In rheumatoid arthritis patients, expression of ATM, and DNA double strand break recognition and repair protein, was found to be downregulated selectively in CD4 T-cells explaining their susceptibility to increased DNA damage and higher turnover rates (9), and we have recently demonstrated increased susceptibility to chemically induced colitis in ATM deficient mice (8). Therefore, the DNA repair capability of leukocytes in terms of expression of ATM and XPC, a nucleotide excision repair protein, was analyzed in IL-10$^{-/-}$ mice with colitis. Transcript levels of ATM and XPC were identical to wildtype mice, and protein levels of pATM were also not significantly different in CD4 or CD8 T-cells between the two genotypes, indicating competent DNA repair capabilities. Other models such as the Gαi2$^{-/-}$ mice whose pathogenesis involves different mechanisms, may however show different DNA repair capabilities compared to wildtype mice.

In summary, the use of DNA damage assays to diagnose and monitor patients in chronic intestinal inflammation is feasible due to the strong correlation to disease activity in mouse models, and preliminary pilot data obtained from blood samples of IBD patients with or without active disease (see Example 4, below). Mechanisms and further implications of systemic genotoxicity are still being investigated, though susceptible cell types have been identified and cytokines such as TNF-α and IL-1β have been found to be sufficient to induce DNA damage. Further work is necessary to outline sufficiency and necessity of events downstream of cytokine administration such as with TNFR deficient mice or administration of enzymatic inhibitors and anti-proliferative agents.

REFERENCES CITED IN EXAMPLE 3

1. Westbrook A M, et al. Cancer Res 2009; 69(11):4827-34.
2. Rudolph U, et al. Nat Genet. 1995; 10(2):143-50.
3. Van der Heijden P J, Stok W. Journal Immunol Methods 1987; 103(2):161.
4. Olive P L, et al. Nat Protocols 2006; 1(1):23-9.
5. Smith C C, et al. Mutagenesis 2006; 21(3):185-90.

6. Goldstine J V, et al. DNA Repair 2006; 5(4):432-43.
7. Muslimovic A, et al. Nature Protocols 2008; 3(7):1187.
8. Westbrook A M, et al. Cancer Research 2010; 70(5):1875-84.
9. Shao L, et al. J Exp Med 2009; 206(6):1435-49.
10. Pitozzi V, et al. Mutation Research/Fundamental and Molecular Mechanisms of Mutagenesis 2003; 529(1-2):129-33.
11. McConnell J R, et al. Clinical and experimental rheumatology; 20(5):653.
12. Grossi S, et al. European Journal of Gastroenterology & Hepatology 2008; 20(1):22-5 10.1097/MEG.0b013e3282f163fe.
13. Watson D, et al. Leukemia Research 2009; 33(Supplement 1):S95-S6.
14. Weng H, et al. Mutation Research/Genetic Toxicology and Environmental Mutagenesis 2008; 652(1):46-53.
15. Scarpaci S, et al. Mechanisms of ageing and development 2003; 124(4):517-24.
16. Castedo M, et al. European Journal of Immunology 1995; 25(12):3277-84.
17. Yachie A, et al. Experimental Biology and Medicine 2003; 228(5):550-6.
18. Dieleman L A, et al. Clinical and Experimental Immunology 1998; 114(3):385.
19. Rennick D M, et al. J Leukoc Biol 1997; 61(4):389-96.
20. Huang T T, et al. Int Immunol 2003; 15(11):1359-67.
21. Mantovani A, et al. Cancer-related inflammation. Nature 2008; 454(7203):436-44.

Example 4: Peripheral Leukocytes from IBD Patients Demonstrate Genotoxicity

This example demonstrates presence of DNA damage, as detected via the alkaline comet assay and γ-H2AX foci formation, in an analysis of peripheral leukocytes of 19 inflammatory bowel disease (IBD) patients with active disease and in those in remission.

Figure 20A:
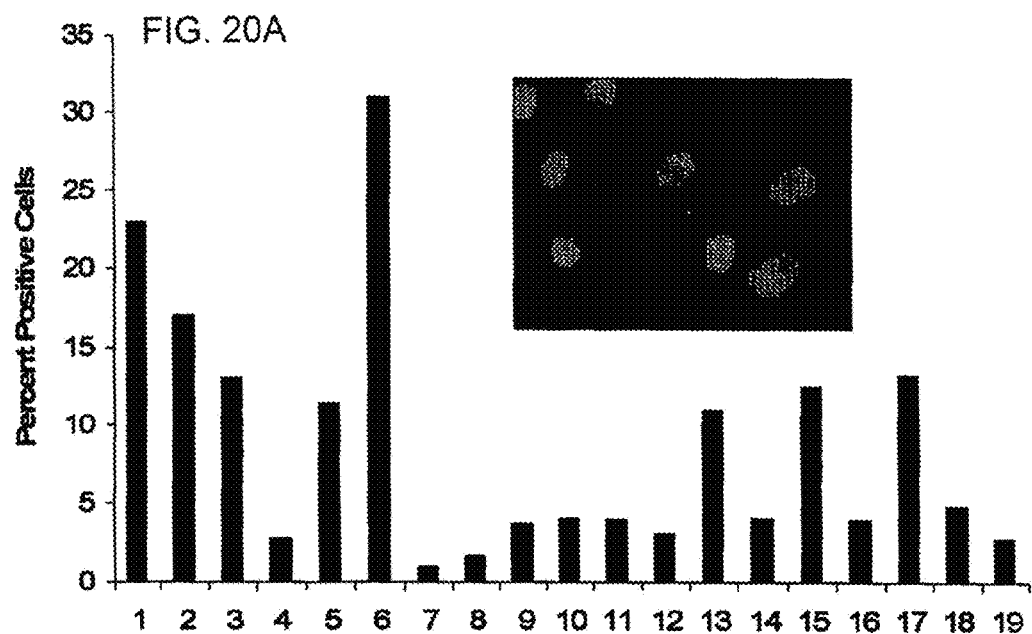
FIGS. 20A-20B. DNA damage in IBD patients. DNA damage to peripheral leukocytes as measured by γH2AX immunostaining and by alkaline comet assay with or without hOgg1 incubation in 19 patients with active disease or in remission.
Figure 20B:
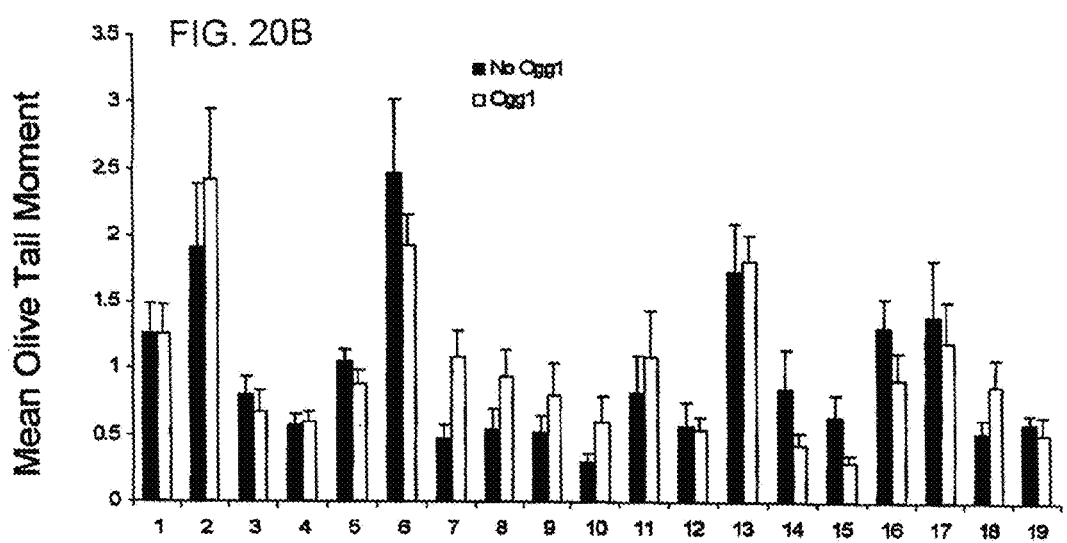

A pilot study utilizing 19 IBD patients from Mount Sinai Medical Center demonstrated significant genotoxicity to peripheral leukocytes in both the alkaline comet assay and in γ-H2AX foci formation. Patients with active disease as well as those in remission were analyzed (FIG. 20). Active Crohn's disease patients demonstrated severe DNA damage by both assays, while those in remission were relatively negative for DNA damage. A couple patients with other diseases including combined variable immunodeficiency disease and hypogammaglobulinemia demonstrated DNA damage as well. Further studies with more negative controls can be done for further validation.

| Disease | Total Number of Patients | Positive for DNA damage |
| --- | --- | --- |
| Active Crohn's disease | 2 | 2 |
| Remission Crohn's disease | 6 | 2 |
| Common variable immunodeficiency | 7 | 2 |
| Ulcerative colitis | 2 | 1 |
| Hypogammaglobulinemia | 1 | 0 |

Example 5: Systemic Genotoxicity in Peripheral Blood in a Mouse Model of Asthma This example demonstrates that IL-13 overexpression in mouse lungs, an animal model for asthma, triggers systemic genotoxicity that can be detected in peripheral blood. The results presented in this example demonstrate that IL-13 is associated with a systemic induction of genotoxic parameters such as oxidative DNA damage, single and double DNA strand breaks, micronucleus formation, and protein nitration. The inflammation induced genotoxicity found in asthma extends beyond the primary site of the lung to circulating leukocytes and erythroblasts in the bone marrow, eliciting systemic effects. Thus, markers of genotoxicity detected in peripheral blood serve as markers for detection and monitoring of asthma.

We used a genetically modified mouse model originally developed by the Elias lab (Ooi 2010) which allow for tetracycline activated conditional over-expression of IL-13 in the Clara Cells of the lungs. We then collected peripheral blood from these asthmatic mice and performed genotoxic assays throughout the progression of the disease.

Materials. & Methods:

Transgenic Mice.

The CC10-rtTA-IL13 transgenic (TG) mouse is a well-characterized model of asthma (Zheng 2000). Clara cell 10-kDa (CC10) gene promoter is used for conditionally expression of IL13 in the mouse lung inducible by doxycycline. CC10-rtTA-IL13 transgenic (TG) mice were generated in Dr. Talel Chatila's lab at the David Geffen School of Medicine University of California Los Angeles, USA. Mice were housed and bred in an institutional specific pathogen free animal facility under standard conditions with a 12 hr light/dark cycle and fed a standard diet according to Animal Research Committee regulations at the University of California, Los Angeles.

Doxycycline Treatment.

5 TG mice and 5 WT littermate control mice were maintained on normal water until one month of age. After one month of age doxycycline was administered to the drinking water 2 g/L in 4% sucrose and kept in aluminum foil covered bottles to prevent light-induced degradation of doxycycline for a 3 week time period. The IL13 transgene exhibits baseline leakiness in the absence of doxycycline allowing transgenic mice to exhibit minor elevation of IL13 expression and minor allergic airway inflammation (Zheng 2000). For this reasoning non-treated transgenic mice were not used as controls in our experiments. After the 3 week exposure to doxycycline all mice were euthanized and pathological assessments were conducted on the lungs.

Blood Collection.

Peripheral blood was collected by facial vein puncture using 5 mm sterile lancets (Medipoint Inc. Mineola, Ny) from experimental mice on specified days throughout the duration of treatment and on sacrifice day via terminal right ventricle cardiac puncture using a heparin-coated syringe (American Pharmaceutical Partners, Inc. Schaumburg, Ill.). Blood from each mouse was collected into EDTA-coated tubes (Sarstedt Aktiengesellschaft & Co., Numbrecht.

Immunofluorescence.

50 ul of whole peripheral blood was put into erythrocyte lysis buffer, cells were laid over poly-D-lysine-coated coverslips and fixed with 4% paraformaldehyde (Electron Microscopy Sciences) at room temperature as described previously (Goldstine 2006). Subsequently, cells were permeabilized with 0.5% Triton X-100 (Sigma), followed by 5 rinses in PBS. Blocking was done in aluminum-covered plates overnight at 4° C. in 10% FBS. Coverslips were then incubated for 1 hour at room temperature with mouse anti-phospho-Histone H2A.X (Upstate, Temecula, Calif.) at a dilution of 1:400, or Mouse anti-8-oxoguanine clone 483.15 (Upstate, Temecula, Calif.) at 1:250 respectively.

Coverslips were then rinsed with 0.1% Triton X-100. Following a second 10% FBS blocking, cells were stained with FITC-conjugated anti-mouse IgG (Jackson ImmunoResearch, West Grove, Pa.) at a dilution of 1:150 for samples with γH2AX primary and (1:200) for samples with 8-oxoguanine primary, respectively for 1 hour at room temperature. Coverslips were mounted onto slides using VECTASHIELD with DAPI (Vector Laboratories, Burlingame, Calif.). For both 8-oxoguanine and γH2AX assay analysis were done on a Zeiss automated microscope. At least 100 cells were counted per sample and cells with more than four distinct foci in the nucleus were considered positive for γH2AX (Westbrook 2009) and cells that exhibited elevated fluorescent intensity compared to background were considered positive for 8-oxoguanine respectively. Apoptotic cells, which have an approximate 10-fold increase in nuclear foci in damaged cells, were not included in analyses (Westbrook 2009; Muslimovic 2008). Statistical analyses were done using Poisson distribution 8-oxoguanine (STATA statistical analysis software) for γH2AX and using ANOVA and Tukey's post hoc test for 8-oxoguanine analysis (Graph Pad Prism).

Micronucleus Assay.

3 μl of whole blood were spread on a microscope slide and stained with Wright-Giemsa solution (Sigma-Aldrich, St. Louis, Mo.). At least 4000 erythrocytes were counted according to published recommendations (Hayashi 1994). MN were counted and scored with an Olympus Ax70 (Tokyo, Japan) at 100× magnification. Statistical analysis was done using repeated measures ANOVA followed by Tukey's post-tests (GraphPad Prism).

DNA Single Strand Breaks.

Oxidative DNA damage and DNA strand breaks were measured in peripheral blood cells using the alkaline comet assay. Peripheral blood was collected before doxycycline administration (day 0), and on days 3, 6, 9, 12, 15, 18 and 21 days of doxycycline treatment. Blood was diluted 1:1 with RPMI+20% DMSO, slowly frozen and stored at −80° C. until the assay was performed. The comet assay was done as described previously (Singh 1988). Briefly, cells were mixed with low melting-point agarose, and placed in triplicate onto normal agarose layed over gelbond (Lonza Inc. Rockland, Me.). The gel was immersed in lysis buffer (2.5 M NaCl, 0.1 M EDTA, 10 mM Tris, 1% Triton, and 10% DMSO), then alkaline electrophoresis buffer (0.3 M NaOH, 1 mM EDTA). After 20 minutes in the electrophoresis buffer at 4° C., the gel was run for 45 minutes at 300 mA, allowed to dry and then stained with SYBR Gold (Molecular Probes). Comet tail-moments were analyzed using CASP (Comet Assay Software Project, http://casp.sourceforge.net/). To measure oxidative DNA damage, the comet assay was modified to include an incubation step with hOGG1 (New England Biolabs, Ipswich, Mass.). As described previously, embedded cells were incubated with hOGG1 (1:300 in NEBuffer1 and BSA) at 37° C. for 30 minutes following the lysis step (Smith 2006). Tail-moments were normalized to a control to account for inter-experimental variability. Statistical analyses were done using ANOVA (GraphPad Prism).

ELISA Analysis.

Serum was separated from blood by centrifugation on all mice immediately before doxycycline administration (Day 0) and on days 3, 5, 7, 10, 13, 16, 18, and 21. After collection serum samples were aliquoted into micro-centrifuge tubes and kept at −20° C. until analysis. Sandwich ELISAs were conducted on samples that were diluted 1:10. Analysis of total Mouse IgE was done according to manufacturer's instructions (BD biosciences). Each sample was done in triplicate and analyzed using the relative standard curve method optical density vs. concentration. Statistical analysis was done using linear mixed model with repeated measurements nested within each mouse. (STATA statistical analysis software)

Gene Expression Analysis.

Lungs from WT and IL-13 mice at the end of the 3-week doxycycline exposure mice were perfused and lavaged before immersion into RNAlater (Qiagen). Lungs were kept at 4° C. for 24 hours then transferred to −80° C. until RNA was isolated using the RNeasy Mini kit according to manufacturer's instructions (Qiagen). cDNA was synthesized using SuperscriptIII (Invitrogen) according to manufacturer's recommendations. Quantitative real-time PCR was performed on an ABI Prism 7500 gene expression system (Applied Biosystems) using Taqman gene expression assays for H2AX, 8-oxoguanine, IL-13, IL-4, IL-5, CCL-11/Eotaxin, TGF-β, Tnfα, and Gapdh was used as an internal control. Each reaction was done in triplicate and analyzed using the relative standard curve method.

Bronchoalveolar Lavage (BAL).

The amount of lung inflammation caused by increased infiltration of immune-circulating cells was assessed by BAL. Briefly, mice were euthanized the trachea was isolated via blunt dissection and small caliber tubing was inserted and secured in the airway. A volume of 1 ml of 1×PBS was flushed and removed 3 times successively from the lungs of WT and IL-13 mice until 3 mL of BAL fluid was collected. BAL fluid was centrifuged at 1600 rpm at 4° C. for 10 minutes. After centrifugation cells were re-suspended in 200 ul of 1×PBS. A 1:1 ratio of cells to trypan blue was put into a hemocytometer and the number of viable cells was counted. After cell viability was assessed 200 ul of remaining cells were put into cytospin and spun at 400 RPM for 5 minutes. Slides were removed from cytospin and allowed to air dry. After drying the slides were stained using (Thermo Kwik Diff staining kit) using manufactures staining recommendation. Slides were allowed to air dry overnight and were mounted with paramount and a coverslip and allowed to dry. Finally at least 200 cells were differentiated by light microscopy based on conventional morphological criteria for each animal.

Immunohistochemistry.

γH2A.X, 8-Hydroxyguanosine, and Nitrotyrosine stains were done on lung tissue of (WT) and IL-13 mice. The slides were placed in xylene to remove paraffin, then a series of ethanol washes. After a wash in tap water, the slides were incubated in 3% Hydrogen peroxide/methanol solution for 10 minutes. The slides were then washed in distilled water, and incubated for 25 minutes in Citrate Buffer pH6 (Invitrogen Corporation) at 95 degrees Celsius using a vegetable steamer. Next, the slides were brought to room temperature, rinsed with PBST (Phosphate Buffered Saline containing 0.05% Tween-20), then incubated at room temperature for 1 hour with Anti-gamma H2A.X (phosphor S139) antibody (abcam, ab22551), 2 hours with anti-8-Hydroxyguanosine antibody (abcam, ab48508), or for 45 minutes with Nitrotyrosine (Millipore, 06-284) at the dilutions of 1:50 for γH2A.X, and 8-Hydroxyguanosine antibodies and at 1:200 for the Nitrotyrosine antibody, respectively. The slides were then rinsed with PBST, and were incubated with Dako EnVision+ System—HRP Labelled Polymer Anti-Mouse (Dako, K4001) at room temperature for 30 minutes. Subsequently after a rinse with PBST, the slides were incubated with DAB (3,3'-Diaminobenzidine) for visualization.

Finally, the slides were washed in tap water, counterstained with Harris' Hematoxylin, dehydrated in ethanol, and mounted with media.

Results

Serum IgE Levels are Induced in IL-13 Mice.

Figure 21:
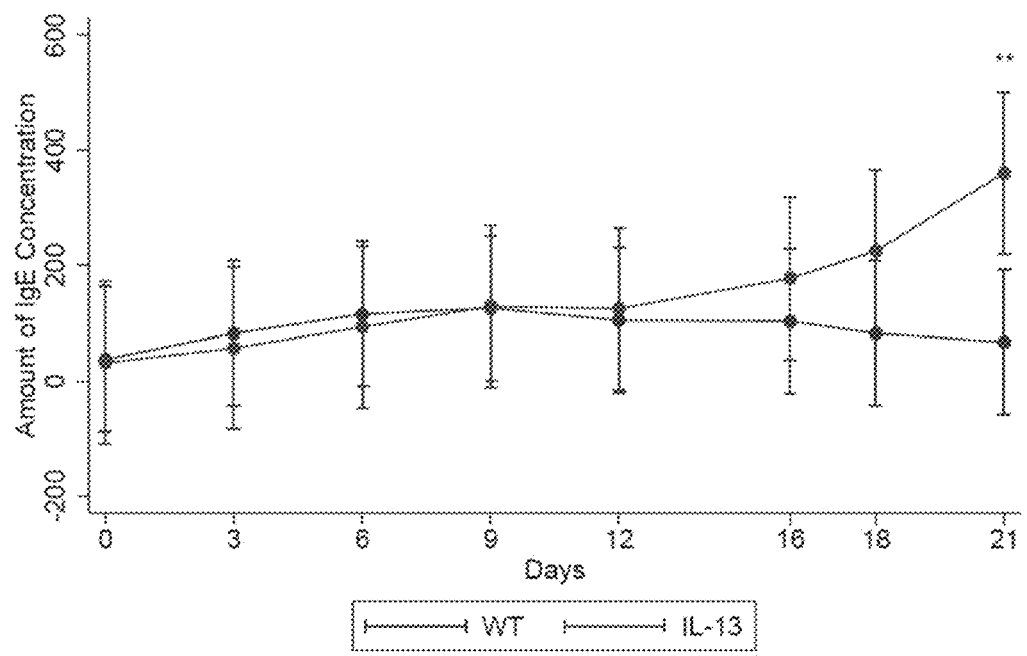
FIG. 21 Line graph showing IgE concentration assessed via sandwich ELISA. **indicates p<, 0.007 n=5 in both IL-13 (upper, lighter line) and WT animals (darker line).

Increased level of IgE is a major factor in the etiology of asthma and is found abundantly in the serum of both human and murine models of asthma (Hamelmann 1999; Mora 2009; Wang 2009). Therefore we assessed the levels of IgE in our transgenic IL-13 over-expression model. We observed that the levels of IgE were higher in the transgenic mice 12 days after IL-13 over-expression and were consistently higher throughout the experiment until terminal day 21 (FIG. 21). Although IL-13 mice exhibited higher IgE levels this induction was only significant at day 21 at **, $p<0.007$ IL-13 Mice Exhibit Increased Inflammation of the Lung.

Figure 22:
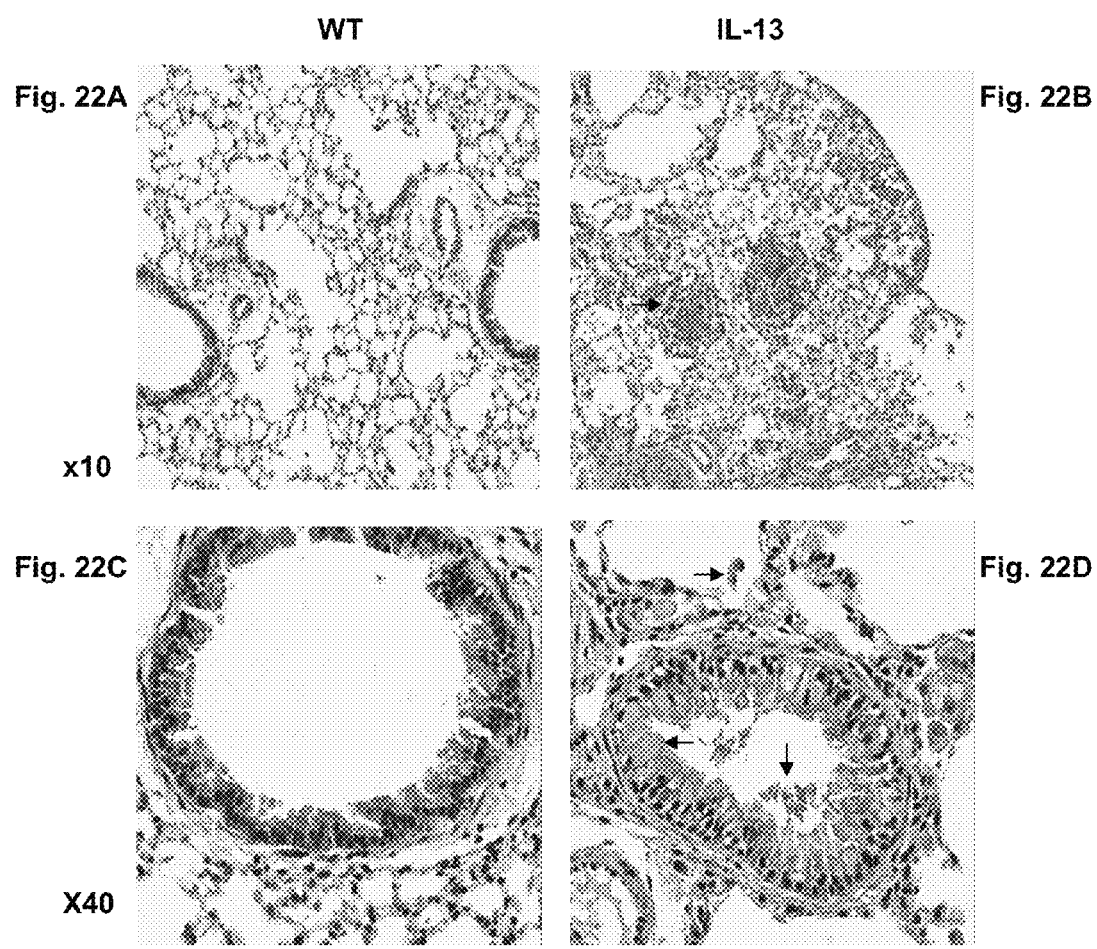
FIGS. 22A-22D IL-13 over-expression induces lung inflammation in asthmatic mice. Representative lung histology Hematoxylin & Eosin (H&E) staining at indicated magnifications. (22A) 10× image of Wild type (WT) lung and Interleukin 13 over expressed mice (22B), both at one month old. Arrows in (22B) 10× image indicate formation of granuloma metafoci surrounding eosinophilic crystals. 40× image of WT (22C) and (22D) 40× image of IL-13 mice. Arrows in (22D) indicate eosinophil migration, goblet cell metaplasia, and eosinophilic crystal formation in bronchial lumen. n=9 for WT and n=10 for IL-13

To understand the role IL-13 induced lung inflammation plays in the genotoxicity and progression of asthma we compared the lungs of WT and IL-13 animals. In (FIGS. 22A and 22C) WT animals exhibit no increase of inflammation.

In contrast IL-13 mice (FIGS. 22B and 22D) exhibit significant inflammation of the lung characterized in the airways bronchiolar lumen. IL-13 mice showed increased inflammatory cells migration in the bronchiolar epithelium, marked hyperplasia, goblet cell metaplasia, and eosinophilic intracytoplasmic inclusion bodies present in clara cells. Thus IL-13 increases inflammation via recruitment of inflammatory cells migrating into airway spaces.

IL-13 Mice Exhibit Increased Immune Cell Infiltration in BAL Fluid.

To delineate what immune cells may be implicated in the persistent inflammatory and genotoxic response present in the asthma mouse model we determined the cellular composition of the BAL fluid in both the WT and IL-13 mice. IL-13 animals had a near 5-fold increase in eosinophil presence in BAL fluid compared to WT animals at $p<0.04$ (FIG. 23). IL-13 mice also exhibited significantly more circulation of neutrophils in the BAL fluid at ***, $p<0.0004$ compared to WT littermates. IL-13 mice also exhibited an increase induction of lymphocytes although this observation was not significantly different from WT animals.

IL-13 Mice Exhibit Persistent Inflammation Induced Immune Response.

Figure 24A:
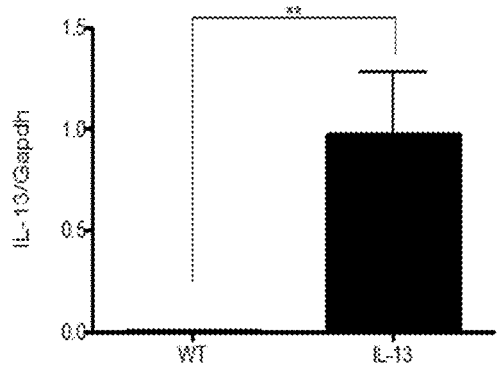
FIGS. 24A-24G Assessment of cytokine panel in lung mRNA measured by quantitative real-time PCR. Mean expression divided by Gapdh, the internal control gene. * indicates p<0.01, ** indicates p<0.001, analysis were conducted using two tailed Student's unpaired T-test. n=9 for WT animals and n=10 for IL-13 animals.
Figure 24B:
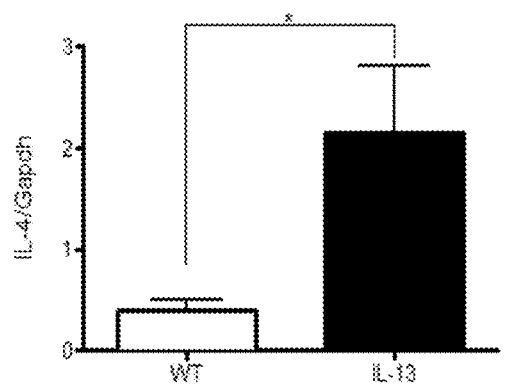
Figure 24C:
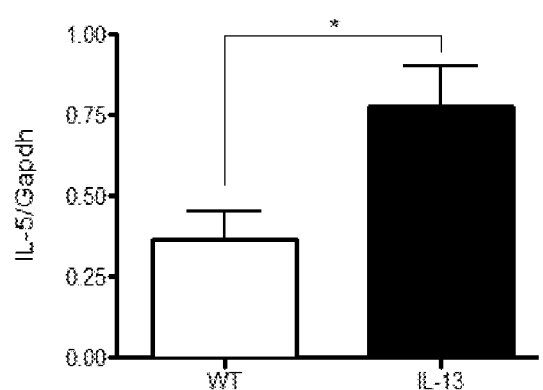
Figure 24D:
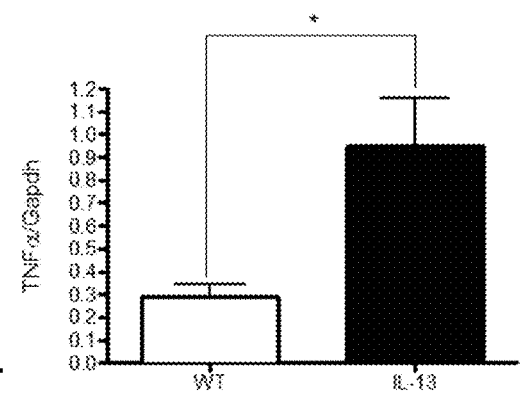
Figure 24E:
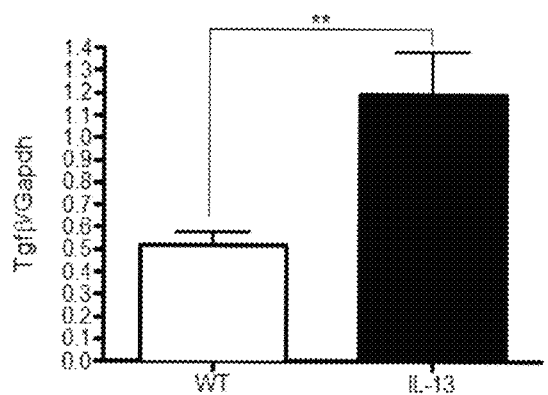
Figure 24F:
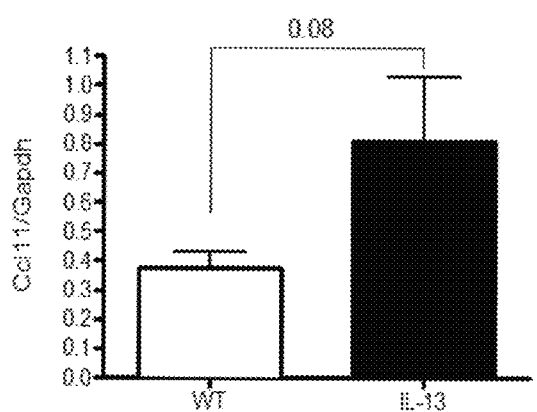
Figure 24G:
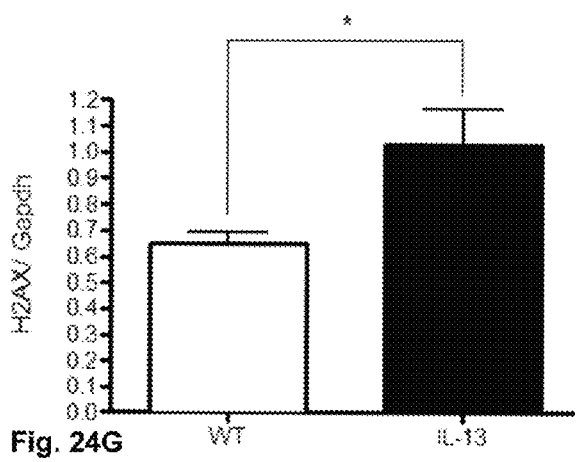

To elucidate the role IL-13 plays in up-regulation of inflammation in the lung we assessed key mediators of asthma FIGS. 24A-24C, inflammatory disease FIGS. 24D-24F, and genotoxicity FIG. 24G via quantitative real-time PCR. As a measurement of further efficacy of our tissue specific asthma model we measured IL-13 levels in the lungs of both groups of experimental mice. The asthma mouse model exhibited an expected significant increased gene expression of IL-13 at **, $p<0.001$ compared to WT animals. IL-4, TNF-$\alpha$, IL-5 were significantly up-regulated in IL-13 mice at *, $p<0.01$ compared to WT animals. IL-13 mice also displayed a marked increase of TGF-$\beta$ FIG. 21-6E at **, $p<0.001$ compared to WT mice. Coil transcript levels in IL-13 mice were slightly higher but did not show a significant increase compared to WT mice FIG. 21-6G These data are indicative of a chronically activated innate immune response present in IL-13 mice compared to WT mice.

IL-13 Mice have Increased Staining of Markers of Genotoxicity in Lung Tissue.

Figure 25:
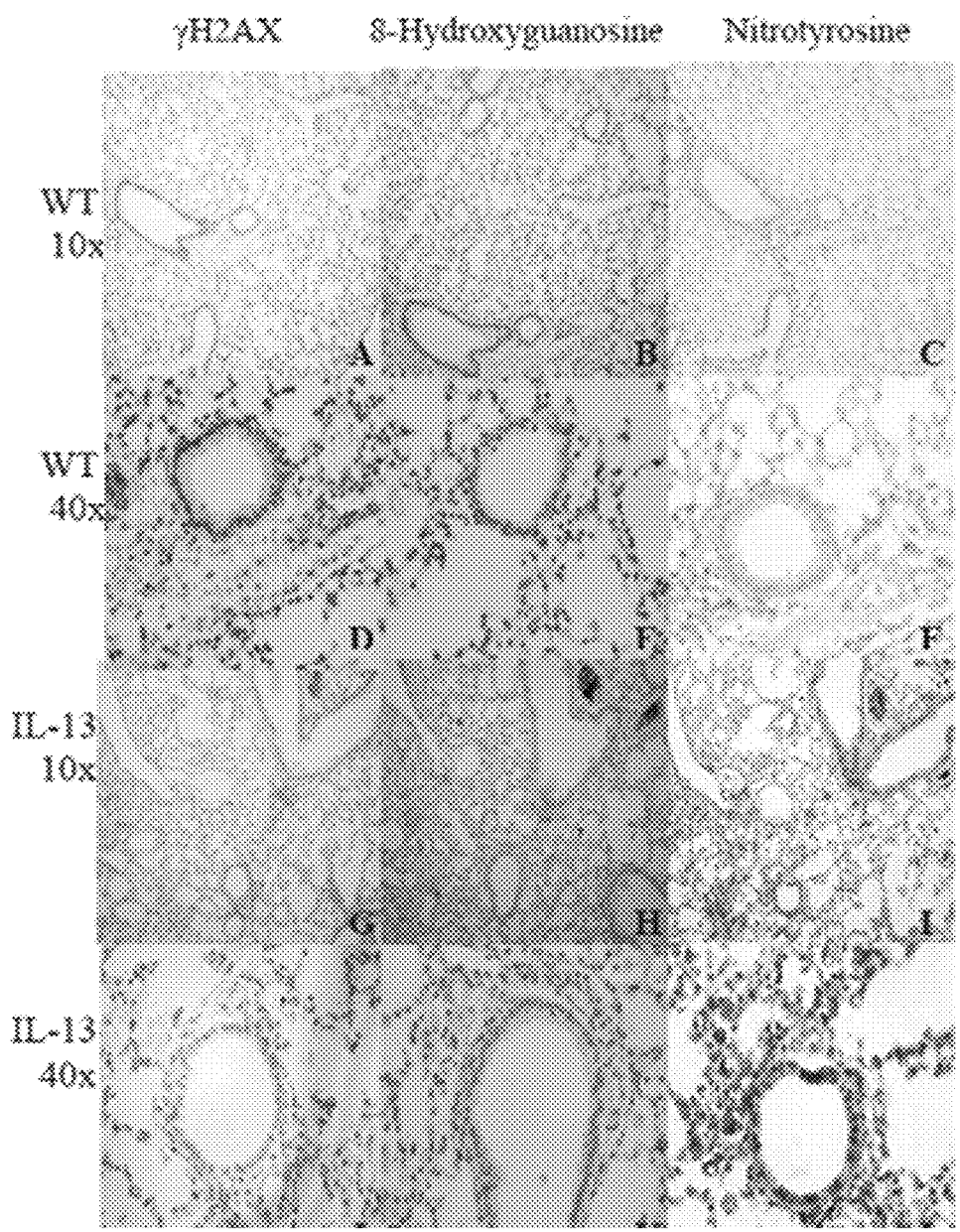
FIG. 25 Photomicrograph showing staining of markers of genotoxicity and oxidative protein damage in lung tissue as measured by immunohistochemistry. Markers of double stranded breaks (A-J), reactive oxygen species (B-K), and inflammation (C-L) induced genotoxicity were stained in WT and IL-13 mice. Lung tissue in IL-13 mice (G-L) exhibited increased staining in all genotoxic parameters in comparison to WT mice (A-F). n=9 for WT animals and n=10 for IL-13 animals.

To further assess asthma induced genotoxicity, the lungs of WT and IL-13 mice were stained with $\gamma$H2AX, anti-8-Hydroxyguanosine, and Nitrotyrosine antibodies. IL-13 mice exhibited increased staining with markers of genotoxicity in the lungs in comparison to WT animals (FIG. 25).

IL-13 Mice Show Systemically Elevated Reactive Oxygen Species Induced Genotoxicity and Double Stranded Breaks in Peripheral Blood.

Figure 26A:
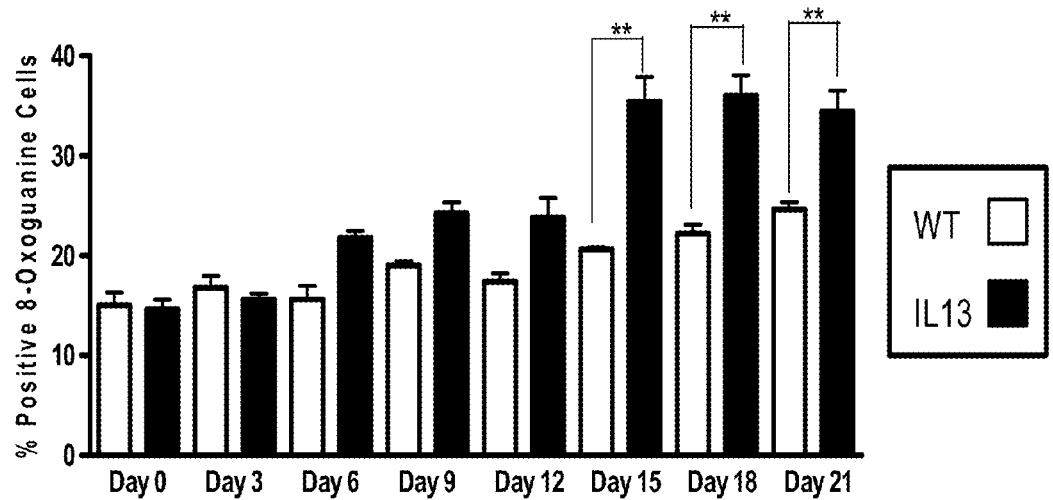
FIGS. 26A-26B Persistent genotoxicity measured via inflammation induced 8-oxoguanine and double stranded breaks measured via γH2AX in peripheral blood. A.) Percent positive cells for 8-oxoguanine induction in white blood cells. Presence of 8-oxoguanine was confirmed by immunofluorescence. Positive cells stain brightly green compared to no immunofluorescent staining for negative cells. White bars indicate Wild type (WT) animals and black bars indicate IL-13 animals. Data represent mean±SEM. Statistical analyses were done using ANOVA testing and Tukey's post hoc analysis. n=5 in all groups. ** indicates p<0.001. B Assessment of double strand breaks measured via γH2AX assay, were counted per cell using fluorescent microscopy before doxycycline administration at Day 0 and after doxycycline administration at days 3, 9, 12, 16, 18 and day 21 using a linear mixed model to determine genotoxic accumulation over time. * indicates p<0.02, ** indicates p<0.002 n=5 for WT and IL-13 animals.
Figure 26B:
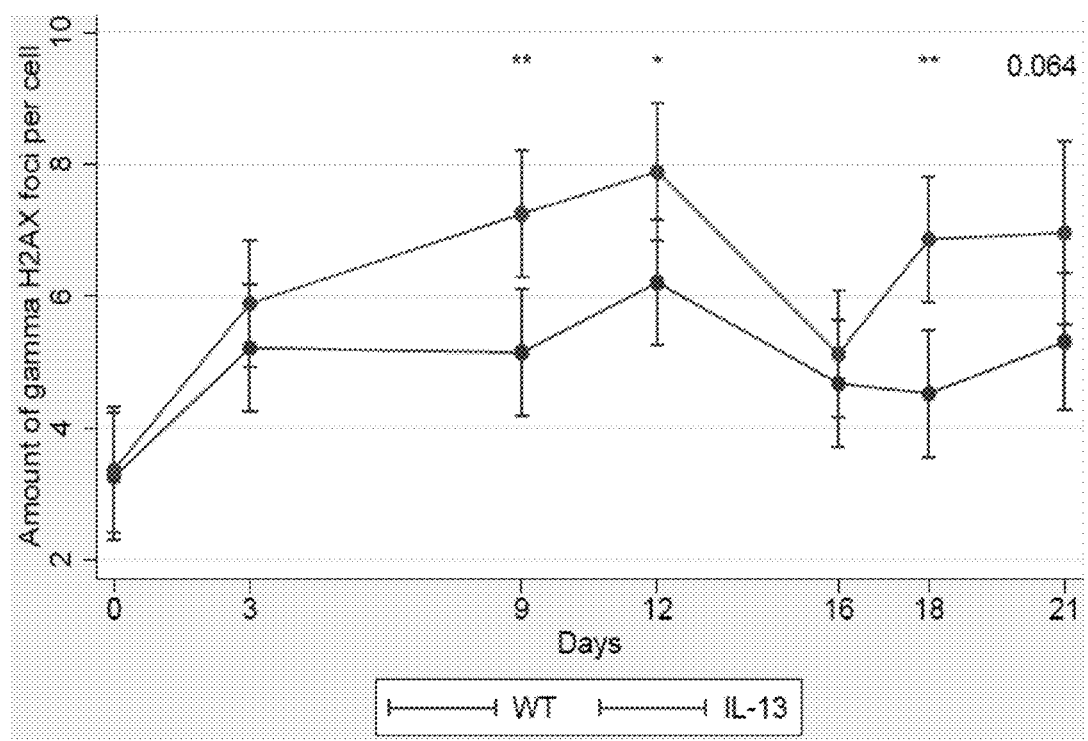

Because IL-13 is a major mediator of allergenic asthma and induces higher levels of inflammation in asthmatic mice (Elias 2003), we hypothesized that inflammation induced systemic DNA damage would be more prevalent in IL-13 compared to wild type (WT) mice. Increase of asthma induced genotoxicity was assessed in peripheral white blood cells as a systemic measurement of DNA damage. 8-oxoguanine is a mutagenic lesion caused by the interaction of a reactive oxygen species to DNA that causes G:C to T:A transversion mutations during replication (Westbrook 2010). Percent positive 8-oxoguanine staining in peripheral white blood cells was assessed using fluorescent microscopy. Blood was taken on day 0 as an assessment of baseline levels of 8-oxoguanine induction between both WT and IL-13 groups. After 6 days of doxycycline presence in drinking water IL-13 mice exhibited a slight increase of 8-oxoguanine immuno-staining compared to wild type mice this induction persisted and became statistically significant at , $p<0.001$ at day 15 and remained elevated throughout the 21 day exposure to doxycycline (FIG. 26A). As a measure of the amount of genotoxicity caused by an accumulation of DNA double strand breaks the $\gamma$H2AX assay was assessed in the WT and IL-13 animals. H2AX is a member of the histone H2A protein family and becomes rapidly phosphorylated in presence of a DNA damaging event (Bonner 2008). This rapid phosphorylation causes recruitment of DNA repair proteins to the site of the break and is detectable by specific antibodies to $\gamma$H2AX. In FIG. 26B we assessed the amount of double strand breaks present in the WT and IL-13 animals. Transgenic animals exhibited an increase in the amount of double strand breaks occurring at every time point after over-expression. This induction of $\gamma$H2AX was significant on day 9 at , $p<0.002$, at day 12 at *, $p<0.02$, and at day 18 day at **, $p<0.001$ respectively. A nearly significant induction of $\gamma$H2AX at $P=0.064$ on day 21 was also observed in the IL-13 mice.

IL-13 Mice have Systemic Single Strand Breaks and Persistent Systemic Genotoxicity that Induces Comet and Micronucleus Formation in Peripheral Blood Leukocytes Respectively.

Figure 27:
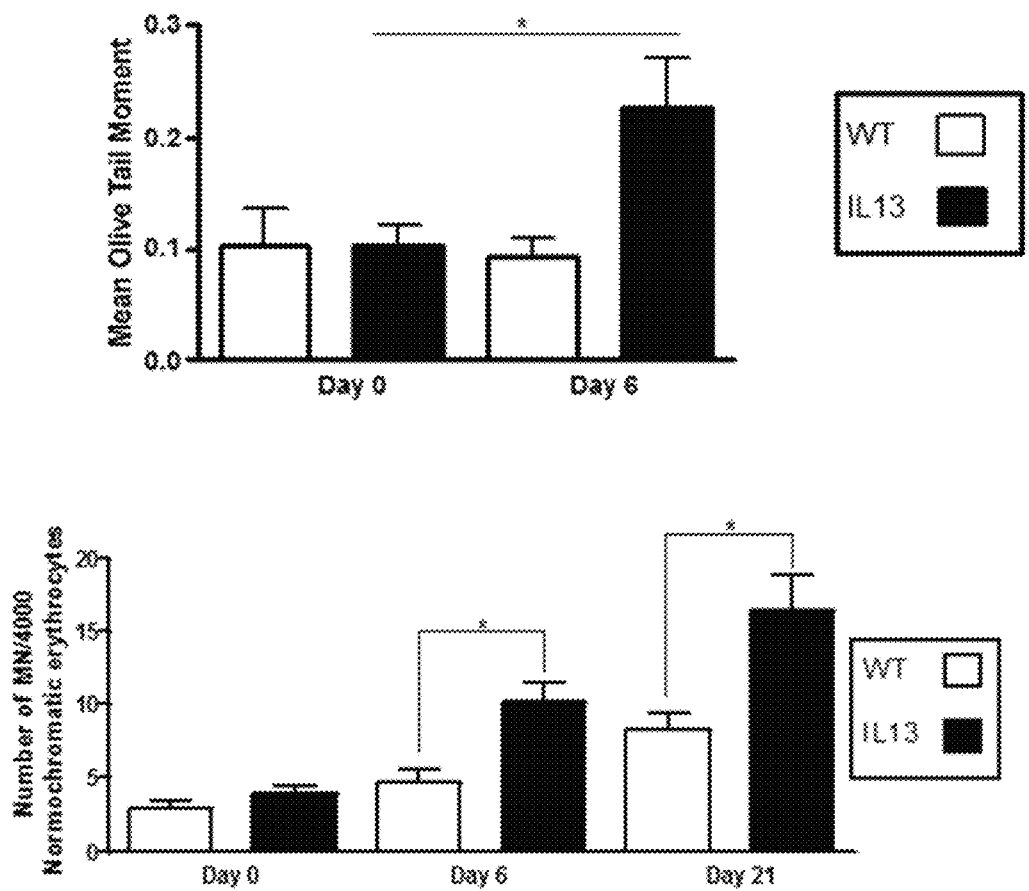
FIG. 27 IL-13 over-expression induced single stranded breaks and micronucleated cells in peripheral blood. Assessment of single strand breaks were measured via comet assay before doxycycline administration at Day 0 and after doxycycline administration at days 6 (upper panel bar graph). At least 100 olive tail moments were counted via fluorescent microscopy and assessed using CASP software. White bars indicate Wild type (WT) animals and black bars indicate IL-13 animals. Data represent mean±SEM. Statistical analyses were done using ANOVA testing and Tukey's post hoc analysis. * indicates p<0.05 n=5 for WT and IL-13 animals. Number of micronucleated cells per 4000 normorchromatic erythrocytes is plotted as a bar graph in the lower panel. Presence of micronuclei were confirmed by light microscope at 100×. White bars indicate Wild type (WT) animals and black bars indicate IL-13 animals. Data represent mean±SEM. Statistical analyses were done using ANOVA testing and Tukey's post hoc analysis. n=9 for WT and n=10 for IL-13.* indicates p<0.05.

The in vivo micronucleus assay was conducted in mature normochromatic erythrocytes circulating in the peripheral blood to determine chromosomal damage. Micronuclei in erythrocytes/erythroblasts from the peripheral blood or bone marrow have been induced in the presence of chromosome breaks, spindle abnormalities, or structurally abnormal chromosomes (Hayashi 1994, Westbrook 2010). Mature micronucleated normochromatic erythrocytes represent the final developmental stage of erythroblasts containing micronuclei stemming in the bone marrow, and permit the simultaneous study of the generation and elimination of micronucleated erythrocytes (Steinheider 1986, Westbrook 2010). Blood was taken on day 0 as an assessment of baseline levels of 8-oxoguanine induction between both WT and IL-13 groups. After 6 days of doxycycline presence in drinking water IL-13 mice exhibited a significant increase of micronuclei formation in peripheral blood compared to WT animals at *, $p<0.05$. This statistically significant induction at *, $p<0.05$ of micronuclei persisted until terminal date Day 21. (FIG. 27A)

The alkaline comet assay is a gel electrophoresis assay that allows the detection of single and double strand breaks, and alkali labile sites at the single cell level (Westbrook 2009). Asthma is an inflammatory disease that produces large amounts of reactive oxygen species (ROS) (Hasbal; Luzina). Interaction of ROS with DNA may result in mutagenic oxidative base modifications such as 8-hydroxydeoxyguanosine (8-oxo-dGuo) and induce DNA strand breaks (Hasbal). Transgenic animals exhibited an increase in the amount of single strand breaks occurring after 6 days of IL-13 over-expression compared to all other groups where no increase was observed. This induction of strand breaks was significant for indicated groups at *, $p<0.05$. (FIG. 27B)

Discussion

Asthma is a chronic obstructive lung disease characterized by chronic inflammation of the airways and recurrent bronchospasms ranging from mild to debilitating (Bosse 2009). It is well established that Interleukin-13 serves as a major mediator of the asthmatic process (Wills-Karp 1998). This study is the first to assess IL-13 role in genotoxicity concomitantly with the inflammatory asthmatic process. Our study also demonstrates for the first time that this genotoxicity extends beyond the primary site of the lung to circulating leukocytes and erythroblasts in the bone marrow eliciting systemic effect in peripheral blood driven by IL-13 overexpression in the lungs.

IL-13 mice exhibited an asthmatic phenotype consistent with previous data. We found a significant increase in IgE. IL-13 mice had sub-epithelial eosinophilic infiltration, peribronchiolar, and perivascular lymphoid infiltration, free floating eosinophilic crystals, many surrounded by aggregates of macrophages, giant cells and neutrophil PMNs (Wills-Karp 1998; Fireman 2003; Grunig 1998). IL-13 mice showed a significant influx of eosinophils, a cellular hallmark of asthma (Conroy 1997), a significant increase in neutrophils, and non-significant increase of lymphocytes in the bronchoalveolar lavage fluid. Transgenic mice had increased gene expression of IL-13, IL-4, IL-5, TNFα, Tgfβ, γH2AX, and Ccl11 produced in the lungs (Ma 2006; Elias2003; Wynn 2003; Vanoirbeek 2009). There was a significant increase in γH2AX levels in the lungs of the IL-13 mice and an induced yet non-significant increase in 8-oxoguanine. In IL-13 mice, we detected a significant increase of single and double stranded breaks in the peripheral blood and lung, a significant induction of micronucleus formation in the normochromatic erythrocytes present in the peripheral blood leukocytes, as well as increased staining of markers of genotoxicity in the lung (Westbrook 2010).

We utilized the well characterized inducible over-expression CC10-rtTA-IL13 transgenic (TG) mouse to elucidate the effect interleukin-13 may have in the genotoxicity of asthma. Recent work has shown that IL-13 signaling is mediated by the type-2 IL-4 receptor, which consists of the IL-4R alpha and IL-13R alpha 1 chains (Munitz 2008; Mentink-Kane 2004), yet IL-13 alone is necessary and sufficient to render the major pathophysiological effects of asthma (Wills-Karp 1998). IL-4 along with IL-13 is a key mediator of inflammation, has an overlapping biological function as IL-13, yet has a distinct role in asthma progression (Munitz 2008). IL-4 is best known for its role for defining the Th2 phenotype of lymphocytes in asthma, but also exacerbating the asthmatic phenotype by increasing airway hyperresponsiveness, eosinophil recruitment, and mucus over-production (Wills-Karp 1998; Grunig 1998). We next investigated mRNA levels of CCL-11/eotaxin. There was not a significant increase in CCL-11/eotaxin transcript present in the lung mRNA, however, we did observe a significant increase in IL-5 lung mRNA transcript.

A possible explanation to the induced yet non-significant increase in CCL11/eotaxin transcript may be found in the work of (Humbles 1997). These data suggest, in corroboration with (Conroy 1997), that migrating eosinophils in the bronchoalveolar lavage fluid may stimulate release of IL-5, but not CCL11/eotaxin.

With regards to the genotoxicity of IL-13 induced asthma we discovered an increase in the amount of γH2AX and 8-oxoguanine in the blood and lungs of these mice. Phosphorylation of histone H2A to form γH2AX in the presence of a DNA damaging event is used as a biomarker of cellular response to DSBs and has a potential for monitoring DNA damage and repair in human and mice (Valdiglesias 2013; Yamamoto 2008). 8-oxo-7,8-dihydroguanine (8oxoG) is an abundant ROS induced lesion that when accumulated has been associated with numerous diseases, including cancer (Westbrook 2009; Evans 2004; Fortini 2003). We did observe a slight increase of 8oxoG in the WT animals which most likely can be attributed to the repeated blood draws that caused a moderate increase in the production of stress related ROS-induced DNA damage similarly found in (Westbrook 2010). As a measure of ongoing DNA damage Westbrook, et. al (Westbrook 2010) show that an accumulation of double-strand breaks can lead to chromosome breaks and micronucleus formation. Perturbations to erythroblasts in the bone marrow may be a humoral effect of inflammation-associated DNA damage, as with the peripheral leukocytes. We suggest that increased inflammation in our experimental mice causes a significant induction of migratory cells that preferentially release pro-inflammatory cytokines at sites of inflammation. This re-circulating pool of activated cells may recruit more effector cells, which come into contact with erythroblasts in the bone marrow causing the observed clastogenicity.

To evaluate the inflammatory cell composition we determined the differential cell percentages. The increased prevalence of neutrophils over that of eosinophils in the bronchoalveolar lavage fluid may depict the presence of a more chronic asthmatic phenotype, an idea supported by (Kamath 2005). Moreover this significant influx of both neutrophils and eosinophils may help generate the enhanced systemic genotoxic response found in the blood. This observation of an induction of γH2AX mRNA levels further confirms increased genotoxicity in IL-13 mice and correlates with our hypothesis of systemic genotoxicity.

In conclusion, we proposed that the key asthmatic mediator interleukin-13, increases important elements of the inflammatory response including ROS derived oxidative stress causing an induction in genotoxicity that has wide reaching systemic genotoxic effects, such as oxidative DNA damage, single and double DNA strand breaks, micronucleus formation, and protein nitration in the peripheral blood. Two potential explanations for the local inflammation and systemic genotoxicity are described by Westbrook et al (Westbrook 2010). In the first model, innate immune cells activated by inflammation release reactive species that damage circulating leukocytes in the periphery. In the second model, inflammatory cytokines are responsible for systemic genotoxicity through cytokine receptor mediated production of free radicals that damage distant leukocytes. These models are not mutually exclusive. Making the second model more likely, it has been shown that injection of cytokines causes systemic genotoxicity in mice (Westbrook 2010). We further suggest increased immune cell infiltration and inflammation byproducts as a possible culprit to this genotoxic induction. The induction of systemic strand breaks which are prevalent in many types of cancer were found to be significantly increased in our IL-13 induced asthma model. Recent studies also point to the fact that asthmatic patients have higher cancer risk (Boffetta 2002; Brown 2006; Garcia Sanz 2011). Previous studies in human asthmatics also identified increased strand breaks produced during the direct interaction of ROS with DNA or during the repair process of damaged DNA (Hasbal; Zeyrek 2009). In summary, asthma is associated with systemic genotoxicity through single and double DNA strand breaks, oxidative DNA damage, protein nitration, and micronucleus formation. This study further implicates IL-13 as a potential therapeutic target for other pulmonary diseases involving carcinogenesis. In addition, systemic genotoxicity might be a convenient blood marker for the extent and severity of asthma.

REFERENCES CITED IN EXAMPLE 5

Akdis, M., et al., J Allergy Clin Immunol, 2011. 127(3): p. 701-21e1-70.
Akinbami, L. J., et al., Natl Health Stat Report, 2011(32): p. 1-14.
Boffetta, P., et al., Eur Respir J, 2002. 19(1): p. 127-33.
Brown, D. W., et al., Cancer Causes Control, 2006. 17(3): p. 349-50.
Bradley, B. L., et al., J Allergy Clin Immunol, 1991. 88(4): p. 661-74.
Bonner, W. M., et al., Nat Rev Cancer, 2008. 8(12): p. 957-67.
Bosse, Y., et al., Respir Res, 2009. 10: p. 98.
Chatila, T. A., Trends Mol Med, 2004. 10(10): p. 493-9.
Cohn, L., et al., Annu Rev Immunol, 2004. 22: p. 789-815.
Conroy, D. M., et al., Mem Inst Oswaldo Cruz, 1997. 92 Suppl 2: p. 183-91.
Elias, J. A., et al., Chest, 2003. 123(3 Suppl): p. 339S-45S
Evans, M. D., et al., Mutat Res, 2004. 567(1): p. 1-61.
Fireman, P., Allergy Asthma Proc, 2003. 24(2): p. 79-83.
Fortini, P., et al., Mutat Res, 2003. 531(1-2): p. 127-39.
Garcia Sanz, M. T., et al., Clin Transl Oncol, 2011. 13(10): p. 728-30.
Goldstine, J. V., et al., DNA Repair (Amst), 2006. 5(4): p. 432-43.
Grunig, G., et al., Science, 1998. 282(5397): p. 2261-3.
Hamelmann, E., et al., Allergy, 1999. 54(4): p. 297-305.
Hasbal, C., et al., Pediatr Allergy Immunol. 21(4 Pt 2): p. e674-8.
Harrington, L. E., et al., Nat Immunol, 2005. 6(11): p. 1123-32.
Hayashi, M., et al., Mutat Res, 1994. 312(3): p. 293-304.
Henderson, W. R., Jr., et al., J Exp Med, 1996. 184(4): p. 1483-94.
Humbles, A. A., et al., J Exp Med, 1997. 186(4): p. 601-12.
Hyde, D., et al., European Respiratory Review, 2006. 15(101): p. 122-135.
Jiang, H., et al., J Allergy Clin Immunol, 2000. 105(6 Pt 1): p. 1063-70.
Kamath, A., et al., Thorax, 2005. 60(7): p. 529-30.
Luzina, I. G., et al., J Leukoc Biol. 92(4): p. 753-64.
Ma, B., et al., J Immunol, 2006. 176(8): p. 4968-78.
Mattes, J., et al., J Exp Med, 2002. 195(11): p. 1433-44.
Medoff, B. D., et al., Annu Rev Immunol, 2008. 26: p. 205-32.
Mentink-Kane, M. M. and T. A. Wynn, Immunol Rev, 2004. 202: p. 191-202.
Miller, A. L., Alternative medicine review: a journal of clinical therapeutic, 2001. 6(1): p. 20.
Mora, J., et al., Clin Immunol, 2009. 132(1): p. 132-40.
Munitz, A., et al., Proc Natl Acad Sci USA, 2008. 105(20): p. 7240-5.
Muslimovic, A., et al., Nat Protoc, 2008. 3(7): p. 1187-93.
Ooi, A. T., et al., Am J Transl Res, 2012. 4(2): p. 219-28.
Romanet-Manent, S., et al., Allergy, 2002. 57(7): p. 607-13.
Singh, N. P., et al., Exp Cell Res, 1988. 175(1): p. 184-91.
Smith, C. C., et al., Mutagenesis, 2006. 21(3): p. 185-90.
Steinheider, G., et al., Cell Biol Toxicol, 1986. 2(1): p. 197-211.
Valdiglesias, V., et al., Mutat Res, 2013.
Vanoirbeek, J. A., et al., Scand J Immunol, 2009. 70(1): p. 25-33.
Wang, X. H., et al., Zhonghua Jie He He Hu Xi Za Zhi, 2009. 32(3): p. 161-4.
Westbrook, A. M., et al., Cancer Res, 2009. 69(11): p. 4827-34.
Westbrook, A. M., et al., Cancer Res, 2009. 69(11): p. 4827-34.
Westbrook, A. M. and R. H. Schiestl, 2010 Cancer Res. 70(5): p. 1875-84.
Wills-Karp, M., et al., Science, 1998. 282(5397): p. 2258-61.
Wynn, T. A., Annu Rev Immunol, 2003. 21: p. 425-56.
Yamamoto, M. L., et al., Mutat Res, 2008. 644(1-2): p. 11-6.
Zeyrek, D., et al., Pediatr Allergy Immunol, 2009. 20(4): p. 370-6.
Zheng, T., et al., J Clin Invest, 2000. 106(9): p. 1081-93.
Zimmermann, N., et al., J Clin Invest, 2003. 111(12): p. 1863-74.

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for detection and treatment of allergic inflammation, the method comprising:
    (a) contacting a test sample of peripheral leukocytes from a subject with reagents for assaying for a marker of DNA damage;
    (b) measuring the amount of marker present in the test sample as compared to a control sample; and
    (c) treating the subject for allergic inflammation if the measured amount of marker in the test sample is increased as compared to the control sample, wherein the treating for allergic inflammation comprises a treatment that targets IL-13.

2. The method of claim 1, wherein the marker of DNA damage is single- and/or double-stranded breaks in leukocytes.

3. The method of claim 2, wherein the measuring comprises an immunoassay for γ-H2AX and/or an alkaline comet assay.

4. The method of claim 1, wherein the marker of DNA damage is oxidative DNA damage in leukocytes.

5. The method of claim 4, wherein the measuring comprises an enzyme hOgg1-modified comet assay or an immunoassay for 8-oxoguanine.

6. The method of claim 1, wherein the peripheral leukocyte is a lymphocyte or a monocyte.

7. The method of claim 1, wherein the sample of peripheral leukocytes is obtained from peripheral blood, or fluid of a body cavity.

8. The method of claim 7, wherein the fluid of a body cavity is pleural, peritoneal, cerebrospinal, mediastinal, or synovial fluid.

9. The method of claim 1, wherein the allergic inflammation is allergic asthma.

10. A method for treating allergic inflammation in a subject, the method comprising:
    (a) contacting a test sample of peripheral blood leukocytes obtained from a subject at a first time point with reagents for assaying for a marker of DNA damage;
    (b) contacting a test sample of peripheral leukocytes obtained from the subject at a second time point with reagents for assaying for a marker of DNA damage, wherein the subject has been treated for inflammatory disease prior to the second time point;
    (c) measuring the amount of marker present in the test samples obtained at the first and second time points;
    (d) determining whether a decreased amount of marker is present in the test sample obtained at the second time point compared to the test sample obtained at the first time point, which decreased amount of marker is indicative of reduced DNA damage; and
    (e) modifying the treatment for inflammatory disease if a decreased amount of marker is not present at the second time point compared to the first time point, wherein the treatment for allergic inflammation comprises a treatment that targets IL-13.

11. The method of claim 10, wherein the marker of DNA damage is single- and/or double-stranded breaks in leukocytes.

12. The method of claim 11, wherein the measuring comprises an immunoassay for $\gamma$-H2AX and/or an alkaline comet assay.

13. The method of claim 10, wherein the marker of DNA damage is oxidative DNA damage in leukocytes.

14. The method of claim 13, wherein the measuring comprises an enzyme hOgg1-modified comet assay or an immunoassay for 8-oxoguanine.

15. The method of claim 10, wherein the allergic inflammation is allergic asthma.

16. The method of claim 1, wherein the increase in measured amount of marker in the test sample as compared to the control sample is a statistically significant increase.

17. The method of claim 10, wherein the modifying comprises increasing the treatment dose or changing to a different therapeutic agent.

* * * * *